US010208053B2

(12) United States Patent
Strohbach et al.

(10) Patent No.: US 10,208,053 B2
(45) Date of Patent: Feb. 19, 2019

(54) BICYCLIC HETEROARYL DERIVATIVES AS CFTR POTENTIATORS

(71) Applicant: CYSTIC FIBROSIS FOUNDATION THERAPEUTICS, INC., Bethesda, MD (US)

(72) Inventors: Joseph Walter Strohbach, Wentzville, MO (US); David Christopher Limburg, Salem, CT (US); John Paul Mathias, Concord, MA (US); Atli Thorarensen, Stow, MA (US); John James Mousseau, Norwich, CT (US); Rajiah Aldrin Denny, Sharon, MA (US); Christoph Wolfgang Zapf, Oakland, CA (US); Ivan Viktorovich Efremov, Chestnut, MA (US)

(73) Assignee: CYSTIC FIBROSIS FOUNDATION THERAPEUTICS, INC., Bethesda, MD (US)

(*) Notice: Subject to any disclaimer, the term of this patent is extended or adjusted under 35 U.S.C. 154(b) by 0 days.

(21) Appl. No.: 16/132,894

(22) Filed: Sep. 17, 2018

(65) Prior Publication Data

US 2019/0016727 A1    Jan. 17, 2019

Related U.S. Application Data

(62) Division of application No. 15/841,902, filed on Dec. 14, 2017, now Pat. No. 10,131,670.

(60) Provisional application No. 62/435,253, filed on Dec. 16, 2016.

(51) Int. Cl.
    *C07D 487/04* (2006.01)
    *A61P 11/00* (2006.01)

(52) U.S. Cl.
    CPC ............ *C07D 487/04* (2013.01); *A61P 11/00* (2018.01)

(58) Field of Classification Search
    CPC .................................................. C07D 487/04

USPC ........................................................ 514/243
See application file for complete search history.

(56) References Cited

U.S. PATENT DOCUMENTS

| | | |
|---|---|---|
| 2005/0085472 A1 | 4/2005 | Tanaka et al. |
| 2009/0170853 A1 | 7/2009 | Bhide et al. |
| 2010/0179125 A1 | 7/2010 | Dixon et al. |
| 2013/0035340 A1 | 2/2013 | Sandner et al. |
| 2013/0158000 A1 | 6/2013 | Brohm et al. |

FOREIGN PATENT DOCUMENTS

WO    WO2007/114926 A2    10/2007

OTHER PUBLICATIONS

Pubchem 61889372 deposited on Oct. 22, 2012, pp. 1-9.
Pubchem 70315227 deposited on Dec. 1, 2012, pp. 1-9.
Patent Cooperation Treaty, International Search Report for PCT/US17/66317, dated Mar. 5, 2018, pp. 1-3.

*Primary Examiner* — Kahsay Habte
(74) *Attorney, Agent, or Firm* — Pillsbury Winthrop Shaw Pittman

(57) ABSTRACT

The present invention relates to 1,3-disubstituted-1H-pyrazolo[3,4-d]pyrimidin-4-amine derivatives and pharmaceutically acceptable salts thereof. The compounds are potentiators of Cystic Fibrosis Transmembrane conductance Regulator (CFTR). The invention also discloses pharmaceutical compositions comprising the compounds, optionally in combination with additional therapeutic agents, and methods of potentiating, in mammals, including humans, CFTR by administration of the compounds. These compounds are useful for the treatment of cystic fibrosis (CF), asthma, bronchiectasis, chronic obstructive pulmonary disease (COPD), constipation, Diabetes mellitus, dry eye disease, pancreatitis, rhinosinusitis, Sjögren's Syndrome, and other CFTR associated disorders.

19 Claims, No Drawings

BICYCLIC HETEROARYL DERIVATIVES AS CFTR POTENTIATORS

CROSS-REFERENCE TO RELATED APPLICATIONS

This application is a divisional of U.S. application Ser. No. 15/841,902 filed Dec. 14, 2017, which claims priority to U.S. Provisional application 62/435,253, filed Dec. 16, 2016, the contents of which are incorporated herein by reference in their entirety.

FIELD OF THE INVENTION

The present invention relates to small molecule potentiators of Cystic Fibrosis Transmembrane conductance Regulator (CFTR). This invention also relates to pharmaceutical compositions comprising the potentiators, optionally in combination with additional therapeutic agents, and methods of potentiating, in mammals, including humans, CFTR by administration of the small molecule CFTR potentiators. The present invention also relates to the treatment of cystic fibrosis and other disorders in mammals, including humans, with the CFTR potentiators. More particularly, this invention relates to 1,3-disubstituted-1H-pyrazolo[3,4-d]pyrimidin-4-amine, 5,7-disubstituted-pyrrolo[2,1-f][1,2,4]triazin-4-amine or 5,7-disubstituted-imidazo[5,1-f][1,2,4]triazine-4-amine derivatives useful for the treatment of cystic fibrosis (CF), asthma, bronchiectasis, chronic obstructive pulmonary disease (COPD), constipation, Diabetes mellitus, dry eye disease, pancreatitis, rhinosinusitis, Sjögren's Syndrome, and other CFTR associated disorders.

BACKGROUND OF THE INVENTION

Cystic fibrosis (CF) is the most common lethal genetic disease affecting Caucasians. CF is an autosomal recessive disease with an incidence of between 1 in 2000 and 1 in 3000 live births (Cutting, G. R., Accurso, F., Ramsey, B. W., and Welsh, M. J., Online Metabolic & Molecular Bases of Inherited Disease, McGraw-Hill, 2013). There are over 70,000 people affected worldwide, of which approximately 33,000 are in the United States (www.cff.org/What-is-CF/About-Cystic-Fibrosis/). The hallmarks of CF are excessive mucus secretion and defective mucus clearance resulting in obstruction, infection and inflammation in the airways; pancreatic insufficiency; and elevated sweat chloride concentration. CF is a multisystem disease affecting the lungs, pancreas, and gastrointestinal, hepatobiliary, and reproductive tracts (R. D. Coakley et al., in Cystic Fibrosis, Eds. Hodson, M., Geddes, D., and Bush, A., Edward Arnold, Third Ed., 2007, pp. 59-68).

For most patients, there is a high burden of care for supportive therapies that do not address the root cause of the disease. Supportive therapies include physical airway clearance techniques, inhaled medications (mucolytics, antibiotics, and hypertonic saline), oral anti-inflammatory drugs, pancreatic enzyme replacements, and nutritional supplements (Cystic Fibrosis Foundation Patient Registry 2011 Annual Data Report to the Center Directors, Cystic Fibrosis Foundation, Bethesda, Md., 2012). The median age of survival for patients with cystic fibrosis is into the fourth decade of life.

Cystic fibrosis is caused by mutations in the gene for CFTR (Cystic Fibrosis Transmembrane conductance Regulator), an ion channel found in epithelia as well as other tissues. CFTR is found at the apical membrane of epithelial cells in the airways, intestine, pancreas, and sweat glands (G. R. Cutting, Accurso, F., Ramsey, B. W., and Welsh, M. J., Online Metabolic & Molecular Bases of Inherited Disease, McGraw-Hill, 2013). Mutations in CFTR have been classified into six types (Welsh, M. J., and Smith, A. E., Cell, 1993, 73, 1251-1254 and Sloane, P. A., and Rowe, S. M., Curr. Opin. Pulm. Med., 2010, 16, 591-597): 1) premature termination due to deletion, nonsense, or frameshift mutations, 2) defective trafficking out of the endoplasmic reticulum due to improper folding, 3) improper gating, 4) reduced conductance due to changes in the channel pore, 5) reduced production of channel due to altered splicing, and 6) increased endocytosis from the plasma membrane.

Nearly 2,000 different mutations in CFTR are known to cause CF. Deletion of Phe508 of CFTR (F508del) occurs in approximately 70% of CFTR alleles (Bobadilla, J. L. et al., Human Mutation, 2002, 19, 575-606). Approximately 50% of patients are F508del homozygotes and ca. 40% are heterozygotes so that at least one copy of F508del is present in about 90% of patients. G551 D is the third most common mutation and is present in about 4% of patients (Cystic Fibrosis Foundation Patient Registry 2011 Annual Data Report to the Center Directors, Cystic Fibrosis Foundation, Bethesda, Md., 2012).

The F508del mutation causes loss of CFTR function due to both reduced channel density and impaired channel gating. Channel density at the apical membrane is reduced due to protein misfolding. Misfolded CFTR is recognized by cellular quality control mechanisms and degraded (Ward, C. L. and Kopito, R. R., J. Biol. Chem., 1994, 269, 25710-25718). F508del function is further reduced because it has a significantly reduced channel open probability (gating defect) (Dalemans, W. et al., Nature, 1991, 354, 526-528). The G551 D mutation results in a protein with normal folding but impaired gating (Illek, B. et al., Am. J. Physiol., 1999, 277, C833-C839).

Small molecules called 'correctors' have been shown to reverse the folding/trafficking defect of F508del CFTR and increase the density of CFTR channels at the plasma membrane (Pedemonte, N. et al., J. Clin. Invest., 2005, 115, 2564-2571, Van Goor, F. et al., Am. J. Physiol. Lung Cell. Mol. Physiol., 2006, 290, L1117-1130, Van Goor, F. et al., Proc. Nat. Acad. Sci. USA, 2011, 108, 18843-18848). 'Potentiators' are small molecules that increase the channel open probability of mutant CFTR, reversing the gating defect. Pharmacological repair of F508del is thought to require at least a corrector and a potentiator to address the folding and gating defects while G551 D may see benefit from a potentiator only.

Kalydeco® (ivacaftor, VX-770) is a marketed potentiator that improves the gating characteristics of G551 D. In G551 D patients, it substantially improved lung function (percent predicted $FEV_1$ increased 10-13%), allowed weight gain, and reduced the frequency of pulmonary exacerbations (Ramsey, B. W. et al., New Eng. J. Med., 2011, 365, 1663-1672, Davies, J. C. et al., Am. J. Resp. Crit. Care Med., 2013, 187, 1219-1225). Kalydeco® is also approved for people with G1244E, G1349D, G178R, G551S, S1251N, S1255P, S549N, and S549R mutations and application to other mutations including those with partial function is being investigated.

While monotherapy with Kalydeco® did not lead to any appreciable improvement in F508del homozygote patients (Flume, P. A. et al., Chest, 2012, 142, 718-724), a combination of a corrector (VX-809, lumacaftor or VX-661, tezacaftor) with Kalydeco® resulted in a modest improvement in lung function (percent predicted $FEV_1$ increased 3-4%) (Wainwright, C. E. et al., N. Engl. J. Med., 2015, 373, 220-231, Pilewski, J. M. et al., J. Cystic Fibrosis, 2015, 14, Suppl. 1, S1). The VX-809 plus Kalydeco® combination (called Orkambi®) is a marketed therapy for F508del homozygote patients.

For both the G551D and the F508del patient populations, improved therapies are expected to provide further benefit to patients. Most G551 D patients are G551D/F508del compound heterozygotes and treatment with the combination of the corrector VX-661 plus Kalydeco® resulted in a further increase in lung function over Kalydeco® alone (Pilewski, J. M. et al., J. Cystic Fibrosis, 2015, 14, Suppl. 1, S1).

Mutations in CFTR that are associated with moderate CFTR dysfunction are also evident in patients with conditions that share certain disease manifestations with cystic fibrosis but do not meet the diagnostic criteria for cystic fibrosis. In these patients, CFTR dysfunction at epithelial cell layers can occur and give rise to abnormal mucus and endocrine secretions that are similar to those that characterize cystic fibrosis. CFTR dysfunction may also be acquired. Chronic inhalation of particulate irritants, including cigarette smoke, pollution, and dust can result in reduced CFTR ion-channel activity.

Modulation of CFTR activity may also be beneficial for other diseases not directly caused by mutations in CFTR, such as secretory diseases and other protein folding diseases mediated by CFTR. CFTR regulates chloride and bicarbonate flux across the epithelia of many cells to control fluid movement, protein solubilization, mucus viscosity and enzyme activity. Defects in CFTR can cause blockage of the airway or ducts in many organs, including the liver and pancreas. Potentiators are compounds that enhance the gating activity of CFTR present in the cell membrane. Any disease which involves thickening of the mucus, impaired fluid regulation, impaired mucus clearance or blocked ducts leading to inflammation and tissue destruction could be a candidate for potentiators. Therefore, there exists a significant therapeutic need for novel small molecules that act as potentiators of CFTR.

In addition to cystic fibrosis, CFTR-related diseases or other diseases which may benefit from modulation of CFTR activity include, but are not limited to, asthma, bronchiectasis, chronic obstructive pulmonary disease (COPD), constipation, diabetes mellitus, dry eye disease, pancreatitis, rhinosinusitis and Sjögren's Syndrome.

SUMMARY OF THE INVENTION

A first embodiment of a first aspect of the present invention is a compound of Formula I

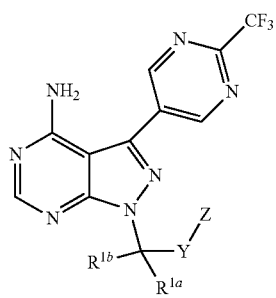

I or a pharmaceutically acceptable salt thereof; wherein Y is a five membered heteroaryl comprising one to four heteroatoms each of which is independently selected from the group consisting of N, O and $S(O)_n$; wherein the heteroaryl is optionally substituted with one to three substituents each of which is independently selected from the group consisting of halo, $C_1$-$C_6$alkyl and $C_1$-$C_6$haloalkyl; Z is phenyl, optionally substituted with one to three halo; $R^{1a}$ and $R^{1b}$ are each independently selected from the group consisting of —H, —OH, halo, $C_1$-$C_6$alkyl optionally substituted with one to three substituents each of which is independently selected from the group consisting of halo, —OH, $C_1$-$C_3$alkoxy, $C_3$-$C_7$cycloalkyl and a four to seven membered heterocycloalkyl comprising one to three heteroatoms each of which is independently selected from the group consisting of N, O and $S(O)_n$, $C_3$-$C_7$cycloalkyl optionally substituted with one to three substituents each of which is independently selected from the group consisting of —OH, halo and $C_1$-$C_6$alkyl, and four to seven membered heterocycloalkyl comprising one to three heteroatoms each of which is independently selected from the group consisting of N, O and $S(O)_n$; and wherein the four to seven membered heterocycloalkyl is optionally substituted with one to three substituents each of which is independently selected from the group consisting of —OH, halo and $C_1$-$C_6$alkyl; or $R^{1a}$ and $R^{1b}$ taken together with the carbon to which they are attached form a $C_3$-$C_7$cycloalkyl or a four to seven membered heterocycloalkyl comprising one to three heteroatoms each of which is independently selected from the group consisting of N, O and $S(O)_n$; and wherein the $C_3$-$C_7$cycloalkyl or four to seven membered heterocycloalkyl are optionally substituted with one to three substituents each of which is independently selected from the group consisting of —OH, halo and $C_1$-$C_6$alkyl; and n at each occurrence is independently 0, 1 or 2.

A second embodiment of the first aspect of the present invention is the compound of the first embodiment, wherein one of $R^{1a}$ and $R^{1b}$ is $C_1$-$C_6$alkyl and the other is —H; or a pharmaceutically acceptable salt thereof.

A third embodiment of the first aspect of the present invention is the compound of the second embodiment, wherein the moiety Y—Z is selected from the group consisting of

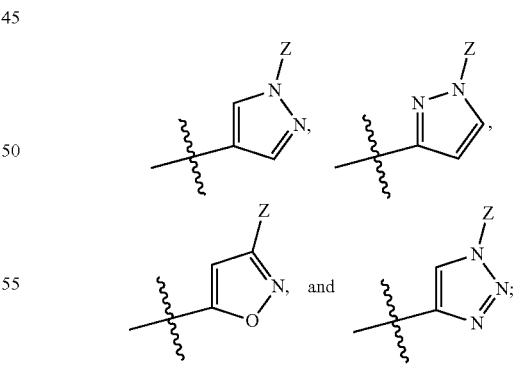

or a pharmaceutically acceptable salt thereof.

A fourth embodiment of the first aspect of the present invention is the compound of the third embodiment wherein Z is phenyl optionally substituted with one or two fluoro or chloro; or a pharmaceutically acceptable salt thereof.

A first embodiment of a second aspect of the present invention is a compound of Formula II <br>

II

<br> or a pharmaceutically acceptable salt thereof; wherein W is a five to six membered heteroaryl comprising one to three heteroatoms each of which is independently selected from the group consisting of N, O and $S(O)_n$; and wherein the heteroaryl is optionally substituted with one to three $R^3$; Y is a five membered heteroaryl comprising one to four heteroatoms each of which is independently selected from the group consisting of N, O and $S(O)_n$; wherein the heteroaryl is optionally substituted with one to three substituents each of which is independently selected from the group consisting of halo, $C_1$-$C_6$alkyl and $C_1$-$C_6$haloalkyl; Z is $C_1$-$C_6$alkyl or phenyl; wherein the phenyl is optionally substituted with one to three halo; $R^{1a}$ and $R^{1b}$ are each independently selected from the group consisting of —H, —OH, halo, $C_1$-$C_6$alkyl optionally substituted with one to three substituents each of which is independently selected from the group consisting of halo, —OH, $C_1$-$C_3$alkyoxy, $C_3$-$C_7$cycloalkyl and a four to seven membered heterocycloalkyl comprising one to three heteroatoms each independently selected from the group consisting of N, O and $S(O)_n$, $C_3$-$C_7$cycloalkyl optionally substituted with one to three substituents each of which is independently selected from the group consisting of —OH, halo and $C_1$-$C_6$alkyl; and four to seven membered heterocycloalkyl optionally substituted with one to three substituents each of which is independently selected from the group consisting of —OH, halo and $C_1$-$C_6$alkyl; or $R^{1a}$ and $R^{1b}$ taken together with the carbon to which they are attached form a $C_3$-$C_7$cycloalkyl or a four to seven membered heterocycloalkyl comprising one to three heteroatoms each of which is independently selected from the group consisting of N, O and $S(O)_n$; and wherein the $C_3$-$C_7$cycloalkyl or four to seven membered heterocycloalkyl are optionally substituted with one to three substituents each of which is independently selected from the group consisting of —OH, halo and $C_1$-$C_6$alkyl; $R^2$ is selected from the group consisting of —H, —CN, halo and $C_1$-$C_3$alkyl; $R^3$ at each occurrence is independently selected from the group consisting of $C_1$-$C_6$alkyl, $C_1$-$C_6$alkoxy, halo and $C_1$-$C_6$haloalkyl; and n at each occurrence is independently 0, 1 or 2.

A second embodiment of the second aspect of the present invention is a compound of the first embodiment of the second aspect of the invention wherein W is pyrimidinyl or pyrazinyl, and wherein the pyrimidinyl or pyrazinyl is optionally substituted with one, two or three $R^3$.

A third embodiment of the second aspect of the present invention is a compound of the first embodiment of the second aspect of the invention wherein the moiety Y—Z is selected from the group consisting of <br>

-continued

<br> or a pharmaceutically acceptable salt thereof.

A first embodiment of a third aspect of the present invention is a compound of Formula III <br>

III

<br> or a pharmaceutically acceptable salt thereof; wherein W is selected from the group consisting of phenyl and a five to six membered heteroaryl comprising one to three heteroatoms each of which is independently selected from the group consisting of N, O and $S(O)_n$; wherein the phenyl and heteroaryl are optionally substituted with one to three $R^3$; Y is a five membered heteroaryl comprising one to four heteroatoms each of which is independently selected from the group consisting of N, O and $S(O)_n$; wherein the heteroaryl is optionally substituted with one to three substituents each of which is independently selected from the group consisting of halo, $C_1$-$C_6$alkyl and $C_1$-$C_6$haloalkyl; Z is $C_1$-$C_6$alkyl or phenyl; wherein the phenyl is optionally substituted with one to three halo; $R^{1a}$ and $R^{1b}$ are each independently selected from the group consisting of —H, —OH, halo, $C_1$-$C_6$alkyl optionally substituted with one to three substituents each of which is independently selected from the group consisting of halo, —OH, $C_1$-$C_3$alkyoxy, $C_3$-$C_7$cycloalkyl and a four to seven membered heterocycloalkyl comprising one to three heteroatoms each of which is independently selected from the group consisting of N, O and $S(O)_n$, $C_3$-$C_7$cycloalkyl optionally substituted with one to three substituents each of which is independently selected from the group consisting of —OH, halo and $C_1$-$C_6$alkyl, and four to seven membered heterocycloalkyl optionally substituted with one to three substituents each of which is independently selected from the group consisting of —OH, halo and $C_1$-$C_6$alkyl; or $R^{1a}$ and $R^{1b}$ taken together with the carbon to which they are attached form a $C_3$-$C_7$cycloalkyl or a four to seven membered heterocycloalkyl comprising one to three heteroatoms each of which is independently selected from the group consisting of N, O and $S(O)_n$; and wherein the $C_3$-$C_7$cycloalkyl or four to seven membered heterocycloalkyl are optionally substituted with one to three substituents each of which is independently selected from the group consisting of —OH, halo and $C_1$-$C_6$alkyl; $R^3$ at each occurrence is independently selected from the group consisting of $C_1$-$C_6$alkyl, $C_1$-$C_6$alkoxy, halo and $C_1$-$C_6$haloalkyl; and n at each occurrence is independently 0, 1 or 2.

A second embodiment of the third aspect of the present invention is a compound of the first embodiment of the third aspect of the present invention wherein W is phenyl which is optionally substituted with one or two halo; or a pharmaceutically acceptable salt thereof.

A third embodiment of the third aspect of the present invention is a compound of the second embodiment of the third aspect of the present invention wherein the compound is 5-(4-chlorophenyl)-7-{[1-(2-fluorophenyl)-1H-1,2,3-triazol-4-yl]methyl}imidazo[5,1-f][1,2,4]triazin-4-amine; or a pharmaceutically acceptable salt thereof.

A fifth embodiment of the first aspect of the present invention is a compound of the first embodiment of the first aspect of the present invention, wherein the compound is selected from the group consisting of 1-{(1S)-1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine;

1-{(1R)-1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine; and 1-{(1S)-1-[1-(2-fluorophenyl)-1H-1,2,3-triazol-4-yl]propyl}-3-[2-(trifluoromethyl)pyrimidin-5-yl]-1H-pyrazolo[3,4-d]pyrimidin-4-amine;

or a pharmaceutically acceptable salt thereof.

A fourth embodiment of the second aspect of the present invention is a compound of the first embodiment of the second aspect of the invention wherein the compound is selected from the group consisting of 7-{(1R)-1-[1-(2-fluorophenyl)-1H-1,2,3-triazol-4-yl]propyl}-5-(4-methoxypyrimidin-5-yl)pyrrolo[2,1-f][1,2,4]triazin-4-amine;

7-{(1R)-1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine;

7-{(1S)-1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine;

4-amino-7-{[1-(2-fluorophenyl)-1H-1,2,3-triazol-4-yl]methyl}-5-[2-(trifluoromethyl) pyrimidin-5-yl]pyrrolo[2,1-f][1,2,4]triazine-6-carbonitrile;

4-amino-7-{(1S)-1-[1-(2-fluorophenyl)-1H-1,2,3-triazol-4-yl]propyl}-5-[2-(trifluoromethyl) pyrimidin-5-yl]pyrrolo[2,1-f][1,2,4]triazine-6-carbonitrile;

4-amino-7-{(1R)-1-[1-(2-fluorophenyl)-1H-1,2,3-triazol-4-yl]propyl}-5-[2-(trifluoromethyl) pyrimidin-5-yl]pyrrolo[2,1-f][1,2,4]triazine-6-carbonitrile;

7-{(1R)-1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine;

4-amino-7-{(1S)-1-[1-(2-fluorophenyl)-1H-1,2,3-triazol-4-yl]ethyl}-5-[2-(trifluoromethyl) pyrimidin-5-yl]pyrrolo[2,1-f][1,2,4]triazine-6-carbonitrile;

4-amino-7-{(1R)-1-[1-(2-fluorophenyl)-1H-1,2,3-triazol-4-yl]ethyl}-5-[2-(trifluoromethyl) pyrimidin-5-yl]pyrrolo[2,1-f][1,2,4]triazine-6-carbonitrile;

7-{(1R)-1-[1-(2,4-difluorophenyl)-1H-1,2,3-triazol-4-yl]propyl}-5-[2-(trifluoromethyl) pyrimidin-5-yl]pyrrolo[2,1-f][1,2,4]triazin-4-amine;

7-{(1R)-1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine;

7-{(1S)-1-[1-(3,4-difluorophenyl)-1H-1,2,3-triazol-4-yl]propyl}-5-[2-(trifluoromethyl) pyrimidin-5-yl]pyrrolo[2,1-f][1,2,4]triazin-4-amine;

4-amino-7-{[1-(2-fluorophenyl)-1H-pyrazol-4-yl]methyl}-5-[2-(trifluoromethyl)pyrimidin-5-yl]pyrrolo[2,1-f][1,2,4]triazine-6-carbonitrile;

4-amino-7-{(1R)-1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile;

4-amino-7-{(1R)-1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1S)-1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(2-fluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1S)-1-[1-(2-fluorophenyl)-1H-pyrazol-4-yl]ethyl}-5-[2-(trifluoromethyl) pyrimidin-5-yl]pyrrolo[2,1-f][1,2,4]triazine-6-carbonitrile;

7-{(1R)-1-[1-(2,4-difluorophenyl)-1H-1,2,3-triazol-4-yl]ethyl}-5-[2-(trifluoromethyl) pyrimidin-5-yl]pyrrolo[2,1-f][1,2,4]triazin-4-amine;

4-amino-7-{(1S)-1-[3-(2-fluorophenyl)-1,2-oxazol-5-yl]ethyl}-5-[2-(trifluoromethyl) pyrimidin-5-yl]pyrrolo[2,1-f][1,2,4]triazine-6-carbonitrile;

4-amino-7-{(1R)-1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile;

4-amino-5-[2-(difluoromethyl)pyrimidin-5-yl]-7-{[1-(2-fluorophenyl)-1H-pyrazol-4-yl]methyl}pyrrolo[2,1-f][1,2,4]triazine-6-carbonitrile;

4-amino-7-{[3-(2-fluorophenyl)-1,2-oxazol-5-yl]methyl}-5-[2-(trifluoromethyl)pyrimidin-5-yl]pyrrolo[2,1-f][1,2,4]triazine-6-carbonitrile;

4-amino-7-{(1R)-1-[1-(propan-2-yl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1S)-1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(2-fluorophenyl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1S)-1-[1-(2-fluorophenyl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1R)-1-[1-(2,4-difluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1S)-1-[1-(2,4-difluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1R)-1-[1-(2,4-difluorophenyl)-1H-pyrazol-4-yl]propyl}-5-[2-(trifluoromethyl) pyrimidin-5-yl]pyrrolo[2,1-f][1,2,4]triazine-6-carbonitrile; and 4-amino-7-{(1S)-1-[1-(2,4-difluorophenyl)-1H-pyrazol-4-yl]propyl}-5-[2-(trifluoromethyl) pyrimidin-5-yl]pyrrolo[2,1-f][1,2,4]triazine-6-carbonitrile;

or a pharmaceutically acceptable salt thereof.

A fifth embodiment of the second aspect of the present invention is a compound of the first embodiment of the second aspect of the invention wherein the compound is selected from the group consisting of 7-{(1R)-1-[1-(2-fluorophenyl)-1H-1,2,3-triazol-4-yl]propyl}-5-(4-methoxypyrimidin-5-yl)pyrrolo[2,1-f][1,2,4]triazin-4-amine;

7-{(1R)-1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine;

4-amino-7-{(1R)-1-[1-(2-fluorophenyl)-1H-1,2,3-triazol-4-yl]propyl}-5-[2-(trifluoromethyl) pyrimidin-5-yl]pyrrolo[2,1-f][1,2,4]triazine-6-carbonitrile;

7-{(1R)-1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine;

4-amino-7-{(1R)-1-[1-(2-fluorophenyl)-1H-1,2,3-triazol-4-yl]ethyl}-5-[2-(trifluoromethyl) pyrimidin-5-yl]pyrrolo[2,1-f][1,2,4]triazine-6-carbonitrile;

7-{(1R)-1-[1-(2,4-difluorophenyl)-1H-1,2,3-triazol-4-yl]propyl}-5-[2-(trifluoromethyl) pyrimidin-5-yl]pyrrolo[2,1-f][1,2,4]triazin-4-amine;

7-{(1R)-1-[1-(2,5-difluorophenyl)-1H-1,2,3-triazol-4-yl]propyl}-5-[2-(trifluoromethyl) pyrimidin-5-yl]pyrrolo[2,1-f][1,2,4]triazin-4-amine;

7-{(1S)-1-[1-(3,4-difluorophenyl)-1H-1,2,3-triazol-4-yl]propyl}-5-[2-(trifluoromethyl) pyrimidin-5-yl]pyrrolo[2,1-f][1,2,4]triazin-4-amine;

4-amino-7-{[1-(2-fluorophenyl)-1H-pyrazol-4-yl]methyl}-5-[2-(trifluoromethyl)pyrimidin-5-yl]pyrrolo[2,1-f][1,2,4]triazine-6-carbonitrile;

4-amino-7-{(1R)-1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile;

4-amino-7-{(1R)-1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile;

4-amino-7-{(1R)-1-[1-(2-fluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1S)-1-[1-(2-fluorophenyl)-1H-pyrazol-4-yl]ethyl}-5-[2-(trifluoromethyl) pyrimidin-5-yl]pyrrolo[2,1-f][1,2,4]triazine-6-carbonitrile;

7-{(1R)-1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine;

4-amino-7-{(1S)-1-[3-(2-fluorophenyl)-1,2-oxazol-5-yl]ethyl}-5-[2-(trifluoromethyl) pyrimidin-5-yl]pyrrolo[2,1-f][1,2,4]triazine-6-carbonitrile;

4-amino-7-{(1R)-1-[3-(2-fluorophenyl)-1,2-oxazol-5-yl]ethyl}-5-[2-(trifluoromethyl) pyrimidin-5-yl]pyrrolo[2,1-f][1,2,4]triazine-6-carbonitrile;

4-amino-5-[2-(difluoromethyl)pyrimidin-5-yl]-7-{[1-(2-fluorophenyl)-1H-pyrazol-4-yl]methyl}pyrrolo[2,1-f][1,2,4]triazine-6-carbonitrile;

4-amino-7-{[3-(2-fluorophenyl)-1,2-oxazol-5-yl]methyl}-5-[2-(trifluoromethyl)pyrimidin-5-yl]pyrrolo[2,1-f][1,2,4]triazine-6-carbonitrile;

4-amino-7-{(1S)-1-[1-(propan-2-yl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1R)-1-[1-(2-fluorophenyl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1S)-1-[1-(2-fluorophenyl)-1H-pyrazol-4-yl]propyl}-5-[2-(trifluoromethyl) pyrimidin-5-yl]pyrrolo[2,1-f][1,2,4]triazine-6-carbonitrile;

4-amino-7-{(1R)-1-[1-(2,4-difluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1S)-1-[1-(2,4-difluorophenyl)-1H-pyrazol-4-yl]ethyl}-5-[2-(trifluoromethyl) pyrimidin-5-yl]pyrrolo[2,1-f][1,2,4]triazine-6-carbonitrile;

4-amino-7-{(1R)-1-[1-(2,4-difluorophenyl)-1H-pyrazol-4-yl]propyl}-5-[2-(trifluoromethyl) pyrimidin-5-yl]pyrrolo[2,1-f][1,2,4]triazine-6-carbonitrile; and 4-amino-7-{(1S)-1-[1-(2,4-difluorophenyl)-1H-pyrazol-4-yl]propyl}-5-[2-(trifluoromethyl) pyrimidin-5-yl]pyrrolo[2,1-f][1,2,4]triazine-6-carbonitrile;

or a pharmaceutically acceptable salt thereof.

A sixth embodiment of the first aspect of the present invention is the compound 1-{(1S)-1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine or a pharmaceutically acceptable salt thereof.

A sixth embodiment of the second aspect of the present invention is the compound 4-amino-5-[2-(difluoromethyl)pyrimidin-5-yl]-7-{[1-(2-fluorophenyl)-1H-pyrazol-4-yl]methyl}pyrrolo[2,1-f][1,2,4]triazine-6-carbonitrile or a pharmaceutically acceptable salt thereof.

A seventh embodiment of the second aspect of the present invention is the compound 4-amino-7-{(1S)-1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile or a pharmaceutically acceptable salt thereof.

An eighth embodiment of the second aspect of the present invention is the compound 4-amino-7-{(1S)-1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile or a pharmaceutically acceptable salt thereof.

A ninth embodiment of the second aspect of the present invention is the compound 4-amino-7-{[1-(2-fluorophenyl)-1H-pyrazol-4-yl]methyl}-5-[2-(trifluoromethyl)pyrimidin-5-yl]pyrrolo[2,1-f][1,2,4]triazine-6-carbonitrile or a pharmaceutically acceptable salt thereof.

A first embodiment of a fourth aspect of the present invention is a method of treating cystic fibrosis, asthma, bronchiectasis, chronic obstructive pulmonary disease (COPD), constipation, Diabetes mellitus, dry eye disease, pancreatitis, rhinosinusitis, or Sjögren's Syndrome in a patient in need of treatment thereof, the method comprising administering a therapeutically effective amount of a compound, or pharmaceutically acceptable salt of said compound, according to any one of the first through sixth embodiments of the first aspect, or any one of the first through ninth embodiments of the second aspect, or any one of the first through third embodiments of the third aspect, to a patient in need of treatment thereof.

A second embodiment of the fourth aspect of the present invention is a method for treating cystic fibrosis in a patient in need of treatment thereof, the method comprising administering a therapeutically effective amount of a compound, or pharmaceutically acceptable salt of said compound, according to any one of the first through sixth embodiments of the first aspect, or any one of the first through ninth embodiments of the second aspect, or any one of the first through third embodiments of the third aspect, to a patient in need of treatment thereof.

A first embodiment of a fifth aspect of the present invention is the compound or pharmaceutically acceptable salt thereof according to any one of the first through sixth embodiments of the first aspect, or any one of the first through ninth embodiments of the second aspect, or any one of the first through third embodiments of the third aspect, for use in the treatment of cystic fibrosis.

A first embodiment of a sixth aspect of the present invention is a pharmaceutical composition comprising a therapeutically effective amount of a compound according to any one the first through sixth embodiments of the first aspect, or any one of the first through ninth embodiments of the second aspect, or any one of the first through third embodiments of the third aspect, or a pharmaceutically acceptable salt thereof together with a pharmaceutically acceptable carrier.

A second embodiment of the sixth aspect of the present invention is the pharmaceutical composition of the first embodiment of the sixth aspect, further comprising one or more additional therapeutic agents.

A third embodiment of the sixth aspect of the present invention is the pharmaceutical composition of the second embodiment of the sixth aspect; wherein the one or more additional therapeutic agents are selected from the group consisting of a CFTR potentiator, a CFTR corrector, an epithelial sodium channel (ENaC) inhibitor, a CFTR amplifier, a CFTR stabilizer, a read-through agent, an oligonucleotide patch, an autophagy inducer, and a proteostasis modulator.

A fourth embodiment of the sixth aspect of the present invention is a pharmaceutical composition of the third embodiment of the sixth aspect; wherein the CFTR potentiator at each occurrence is selected from the group consisting of VX-770 (Ivacaftor), GLPG-1837, GLPG-2451, QBW-251, FDL-176, FDL-129, CTP656, and PTI-P271.

A fifth embodiment of the sixth aspect of the present invention is a pharmaceutical composition of the third embodiment of the sixth aspect; wherein the CFTR corrector at each occurrence is selected from the group consisting of VX809 (lumacaftor), VX-661 (tezacaftor), VX-983, VX-152, VX-440, VX-659, GLPG2737, P247-A, GLPG-2222, GLPG-2665, GLPG-2851, FDL-169, and PTIC1811.

A sixth embodiment of the sixth aspect of the present invention is a pharmaceutical composition of the third embodiment of the sixth aspect; wherein the epithelial sodium channel (ENaC) inhibitor at each occurrence is selected from the group consisting of SPX-101, QBW-276 and VX-371.

A seventh embodiment of the sixth aspect of the present invention is a pharmaceutical composition of the third embodiment of the sixth aspect; wherein the CFTR amplifier at each occurrence is selected from the group consisting of PTI428 and PTI-130.

An eighth embodiment of the sixth aspect of the present invention is a pharmaceutical composition of the third embodiment of the sixth aspect; wherein the CFTR stabilizer is N-91115 (Cavosonstat).

A ninth embodiment of the sixth aspect of the present invention is a pharmaceutical composition of the third embodiment of the sixth aspect; wherein the read-through agent is ataluren (PTC124).

A tenth embodiment of the sixth aspect of the present invention is a pharmaceutical composition of the third embodiment of the sixth aspect; wherein the autophagy inducer at each occurrence is selected from the group consisting of CX-4945 and the combination of cysteamine and epigallocatechin gallate (EGCG).

A first embodiment of a seventh aspect of the present invention is a method for treating cystic fibrosis in a patient in need of treatment thereof, the method comprising administering the pharmaceutical composition according to any one of the first through tenth embodiments of the sixth aspect to the patient in need of treatment thereof.

A first embodiment of an eighth aspect of the present invention is the pharmaceutical composition according to any one of the first through tenth embodiments of the sixth aspect for use in the treatment of cystic fibrosis.

DEFINITIONS

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "haloalkyl" refers to an alkyl in which at least one hydrogen on the alkyl is replaced with a halogen atom. The term "$C_1$-$C_6$ haloalkyl" refers to a $C_1$-$C_6$ alkyl group, as defined herein, in which one, two, three, four, five, or six hydrogen atoms are replaced by halogen. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. Examples of haloakyls include: chloromethyl, fluoromethyl, difluoromethyl, trifluoromethyl, 1,1-difluoroethyl, 2-fluoroethyl, 2,2-difluoroethyl, 2-chloro-3-fluoropentyl, and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen atom from a saturated carbocyclic molecule and having the specified number of carbon atoms. In one embodiment, a cycloalkyl substituent has three to seven carbon atoms (i.e., $C_3$-$C_7$cycloalkyl). Examples of cycloalkyl include cyclopropyl, cyclobutyl, cyclopentyl, cyclohexyl and cycloheptyl. The term "cycloalkyl" includes mono-, bi- and tricyclic saturated carbocycles, as well as bridged and fused ring carbocycles, as well as spiro-fused ring systems.

As used herein, the term "heterocycloalkyl" refers to a monocyclic ring system containing the heteroatoms N, O or $S(O)_n$ as specified. The term "heterocycloalkyl" refers to a substituent obtained by removing a hydrogen from a saturated or partially saturated ring structure containing the specified number of ring atoms; wherein at least one of the ring atoms is a heteroatom (i.e. oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. In some instances, the number of atoms in a cyclic substituent containing one or more heteroatoms (i.e., heteroaryl or heterocycloalkyl) is indicated by the prefix "x to y membered"; wherein x is the minimum and y is the maximum number of atoms forming the cyclic moiety of the substituent. Thus, for example, "four to seven membered heterocycloalkyl" refers to a heterocycloalkyl containing from four to seven atoms, including one or more heteroatoms, in the cyclic moiety of the heterocycloalkyl. Examples of single-ring heterocycloalkyls include azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, and diazepinyl.

The term "heteroaryl" refers to an aromatic ring structure containing the specified number of ring atoms in which at least one of the ring atoms is a heteroatom (i.e. oxygen, nitrogen, or sulfur), with the remaining ring atoms being independently selected from the group consisting of carbon, oxygen, nitrogen, and sulfur. A five to six membered heteroaryl is an aromatic ring system which has five or six ring atoms with at least one of the ring atoms being N, O or $S(O)_n$.

Examples of heteroaryl substituents include six membered ring substituents such as pyridinyl, pyrazinyl, pyrimidinyl, and pyridazinyl; five membered ring substituents such as pyrrolyl, theinyl, furanyl, triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridinyl N-oxides and groups containing a pyridine N-oxide ring. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

The term "halo" or "halogen" refers to fluoro (which may be depicted as —F), chloro (which may be depicted as —Cl), bromo (which may be depicted as —Br), or iodo (which may be depicted as —I).

The term "hydrogen" refers to a hydrogen substituent, and may be depicted as —H.

The term "hydroxy" or "hydroxyl" refers to —OH. Compounds bearing a carbon to which one or more hydroxyl substituents are attached include, for example, alcohols, enols and phenol.

The term "phenyl" refers to an aromatic ring having the radical —$C_6H_5$, derived from benzene by removal of a hydrogen atom. Phenyl, if so specified, may be optionally fused with a five or six membered cycloalkyl or heterocycloalkyl ring to form bicyclic compounds. Examples of these bicyclic compounds include 1,2,3,4-tetrahydronaphthalene, 2,3-dihydrobenzo[1,4]oxazine, 2,3-dihydro-1H-indene, isoindoline, and 2,3-dihydrobenzo[1,4]dioxine.

If substituents are described as being "independently selected" from a group, each instance of a substituent is selected independent of the other. Each substituent therefore may be identical to or different from the other substituent(s).

As used herein, the term "formula I", "formula (I)", "Formula (I)", or "Formula I"; "formula II", "formula (II)", "Formula (II)", or "Formula II"; or "formula III", "formula (III)", "Formula (III)", or "Formula III" may be referred to as a "compound(s) of the invention". Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288, Haleblian, J. K. (August 1975).

The compounds of the invention may have asymmetric carbon atoms. The carbon-carbon bonds of the compounds of the invention may be depicted herein using a solid line ( —— ), a solid wedge ( —■ ), or a dotted wedge ( ⋯⋯ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formulae I, II, or III may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formulae I, II, or III can exist as enantiomers and diastereomers or as racemates and mixtures thereof. The use of a solid line to depict bonds to one or more asymmetric carbon atoms in a compound of Formulae I, II, or III and the use of a solid or dotted wedge to depict bonds to other asymmetric carbon atoms in the same compound is meant to indicate that a mixture of diastereomers is present.

Stereoisomers of Formulae I, II, or III include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

Examples of types of potential tautomerisms shown by the compounds of the invention include hydroxypyridine ⇔ pyridone; amide ⇔ hydroxyl-imine and keto ⇔ enol tautomersims:

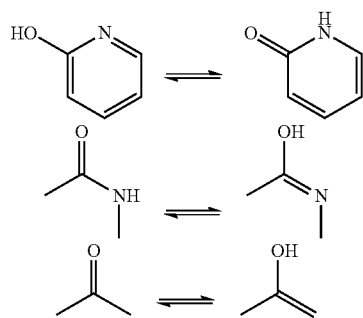

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound. Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formulae I, II, or III with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts". Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, P-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N, N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g. methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs". Further information on the use of prodrugs may be found in "Pro-drugs as Novel Delivery Systems", Vol. 14, ACS Symposium Series (T. Higuchi and V. Stella, Eds.), American Chemical Society, 1975 Washington, D.C. and "Bioreversible Carriers in Drug Design", Pergamon Press, 1987 (E. B. Roche, Ed.) American Pharmaceutical Association. Prodrugs in accordance with the invention can, for example, be produced by replacing appropriate functionalities present in the compounds of any of Formulae I, II, or III with certain moieties known to those skilled in the art as "pro-moieties" as described, for example, in Bundgaard, H. 1985. Design of Prodrugs. New York: Elsevier.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively.

Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formulae I, II, or III of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention.

In another embodiment, the oral administration may be in a powder or granule form. In another embodiment, the oral administration may be in a spray-dried dispersion. In another embodiment, the oral dose form is sub-lingual, such as, for example, a lozenge. In such solid dosage forms, the compounds of Formulae I, II, or III are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing or wetting agents and suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety.

Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and nonbiodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray, delivered from a pressurized container or a nebulizer with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Lieberman et al., Eds., Pharmaceutical Dosage Forms, Marcel Dekker, New York, N.Y., 1980; and Kibbe et al., Eds., Handbook of Pharmaceutical Excipients (3rd ed.), American Pharmaceutical Association, Washington, 2000.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration", "co-administration", "simultaneous administration," and "administered simultaneously" mean that the compounds are administered in combination.

The present invention includes the use of a combination of a CFTR potentiator compound as provided in Formulae I, II, or III and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formulae I, II, or III or a pharmaceutically acceptable salt of the compound; (b) a second pharmaceutically active agent; (c) optionally a third pharmaceutically active agent; and (d) a pharmaceutically acceptable carrier, vehicle or diluent.

Various pharmaceutically active agents may be selected for use in conjunction with the compounds of Formulae I, II, or III, depending on the disease, disorder, or condition to be treated. For example, a pharmaceutical composition for use in treating Cystic Fibrosis may comprise a compound of Formulae I, II, or III or a pharmaceutically acceptable salt thereof, together with one or more agents such as a CFTR modulator, for example another CFTR potentiator, a CFTR corrector, including a CAL (CFTR-associated ligand) inhibitor, a CFTR Production corrector or read-through agent, a CFTR stabilizer, including a CFTR-Dab2 (Disabled homolog 2) inhibitor, or a CFTR amplifier; an epithelial sodium channel (ENaC) inhibitor/blocker;

an oligonucleotide patch; an autophagy inducer; a proteostasis modulator, including a histone deacetylase (HDAC) inhibitor; or supportive therapies such as a mucolytic agent, a bronchodilator, an antibiotic, an anti-infective agent, an anti-inflammatory agent, an anticholinergic, a mast cell stabilizer, a corticosteroid, a nutritional agent, or an enzyme replacement.

A combination can include more than one agent from a particular class of agents; for example, a combination of a compound of Formulae I, II, or III with two or more CFTR correctors. Pharmaceutically active agents that may be used in combination with the compounds of Formulae I, II, or III and compositions thereof include, without limitation:

(i) CFTR potentiators, such as VX-770 (ivacaftor), GLPG-1837, GLPG-2451, QBW-251, GLPG-3067, FDL-129, CTP-656, FDL-176, PTI-P271, and CTP-656;
(ii) CFTR correctors, such as VX-809 (lumacaftor), VX-661 (tezacaftor), VX-983 VX-152, VX-440, VX-659, GLPG-2737, P247-A, FDL-169, FDL-304, GLPG-2222, GLPG-2665, GLPG-2851, PTI-C1811, NU-001, and NU-002
(iii) CFTR amplifiers, such as PTI-428 and PTI-130
(iv) Read-through agents, such as ataluren
(v) CFTR stabilizers, such as N91115 (cavosonstat, an S-nitrosoglutathione reductase "GSNOR" inhibitor)
(vi) Epithelial sodium channel (ENaC) inhibitors, such as SPX-101, QBW-276 and VX-371;
(vii) Oligonucleotide patches, such as QR-010
(viii) Autophagy inducers, such as CX-4945, the combination of cysteamine and epigallocatechin gallate (EGCG), cystamine, and rapamycin
(ix) Proteostasis modulators, such as histone deacetylase (HDAC) inhibitors including 4-phenylbutyrate (4-PBA)
(x) Supportive therapies, such as albuterol, salmeterol, ciprofloxacin, fluticasone, prednisone, ipratropium bromide, lipase, protease, and amylase The present invention further comprises kits that are suitable for use in performing the methods of treatment described above. In one embodiment, the kit contains a first dosage form comprising one or more of the compounds of the present invention optionally in combination with one or more additional therapeutic agents and a container for the dosage, in quantities sufficient to carry out the methods of the present invention. In another embodiment, the kit of the present invention comprises one or more compounds of the invention optionally with one or more additional therapeutic agents.

General Synthetic Schemes

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I). It will be further appreciated that it may be necessary or desirable to carry out the transformations in a different order from that described in the schemes, or to modify one or more of the transformations, to provide the desired compound of the invention.

All of the derivatives of Formulae I, II, and III can be prepared by the procedures described in the general methods presented below or by routine modifications thereof. The present invention also encompasses any one or more of these processes for preparing the derivatives of Formulae I, II, and III, in addition to any novel intermediates used therein. The person skilled in the art will appreciate that the following reactions may be heated thermally or under microwave irradiation.

The routes below, including those mentioned in the Examples and Preparations, illustrate methods of synthesising compounds of Formulae I, II, and III. The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in a conventional manner. See, for example, those described in 'Greene's Protective Groups in Organic Synthesis' by Theodora W Greene and Peter G M Wuts, fifth edition, (John Wiley and Sons, 2014), incorporated herein by reference, which also describes methods for the removal of such groups.

In the general synthetic methods below, unless otherwise specified, the substituents are as defined above with reference to the compounds of Formula (I) above. Where ratios of solvents are given, the ratios are by volume unless otherwise specified.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula I.

The following general methods depict the preparation of the compounds of Formulae (I) and (II) and (III) as shown below.

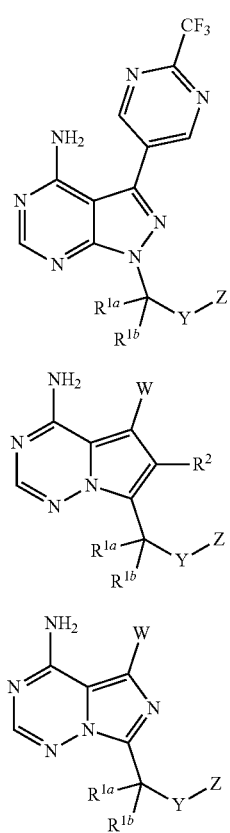

According to a first process, compounds of formula (IIC), (a compound of Formula II wherein $R^2$ is CN) may be prepared from compounds of formulae (IIA) and (IIB, a compound of Formula II wherein $R^2$ is Hal) as illustrated by Scheme 1 wherein Hal is chloro, bromo or iodo, preferably bromo.

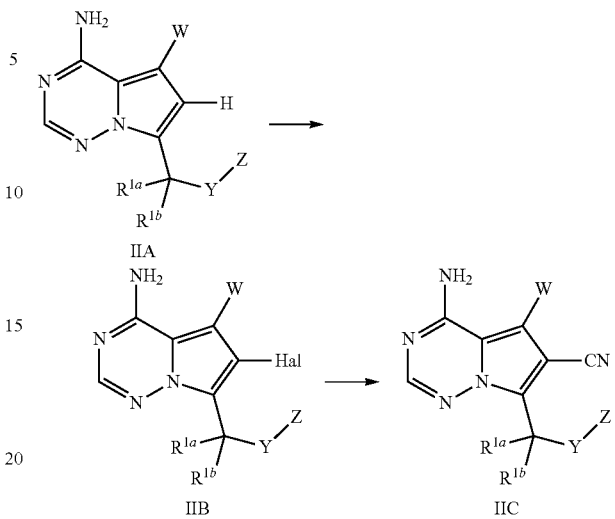

In Scheme 1, compound of the formula (IIA) is converted to a compound of formula (IIB) by treatment with a suitable halogenating agent such as N-(Hal)succinimide, preferably NBS (where Hal is bromo), in a suitable solvent, such as DCM or DMF at an appropriate temperature such as 0° C. A skilled person also knows that alternative methods for specifically introducing a suitable halogen group such as Br are achievable using alternative reagents, solvents and temperatures. A compound of formula (IIB) is converted into a compound of formula (IIC) by treatment with a suitable organometallic source of cyanide such as $Zn(CN)_2$ or CuCN in the presence of a suitable catalyst, such as $Pd(dppf)Cl_2$ (or $Pd_2(dba)_3$ plus dppf) in a suitable solvent, such as DMF or NMP at a suitable temperature. A skilled person also knows that alternative organometallic coupling strategies can be used involving alternative coupling partners, metals and solvent combinations. It is well understood by a skilled person that a compound of the formula (IIB) is prepared and isolated as described above or prepared in situ without isolation in a sequential reaction strategy leading to a compound of formula (IIC).

According to a second process, compounds of Formula (II) may be prepared from compounds of Formulae (IID), (IIE) and (V) as illustrated by Scheme 2 wherein Hal is chloro, bromo or iodo.

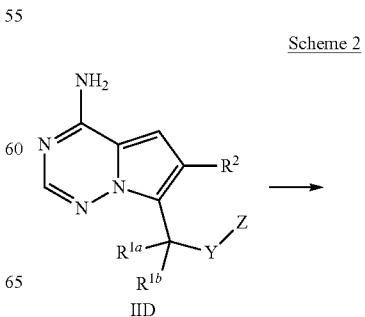

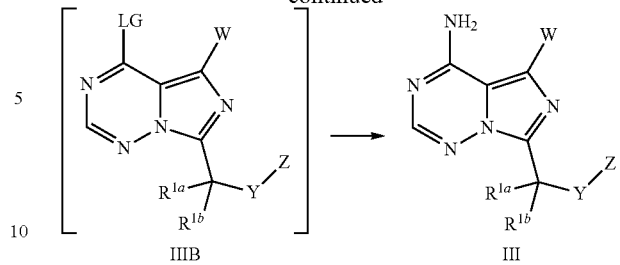

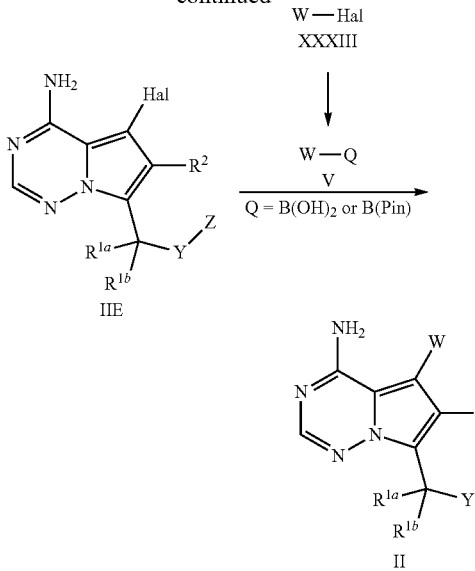

In Scheme 2, compounds of Formula (II) may be prepared from compounds of Formulae (IIE) and (V) using a suitable organometallic cross-coupling reaction such as Suzuki cross-coupling reaction preceded if necessary by a boronic acid or ester formation. Typical Suzuki cross-coupling conditions comprise a palladium catalyst containing suitable phosphine ligands, in the presence of an inorganic base, in aqueous dioxane, at elevated temperatures either thermally or under microwave irradiation. Preferred conditions comprise $Pd(OAc)_2$, $Pd(dppf)Cl_2$ or $Pd(PPh_3)_4$ with either sodium, cesium or potassium carbonate in aqueous dioxane or methanol at from room temperature to 120° C. If necessary compounds of Formula (V) may be prepared using typical boronic ester formation conditions comprising $Pd(dppf)Cl_2$ and potassium acetate with bispinacolatodiboron with compounds of Formula (XXXIII) (wherein Hal is Cl, Br, or I) in dioxane at reflux. Compounds of Formula (IIE) may be prepared from compounds of Formula (IID) using a suitable halogenation reaction such as NBS (when Hal is bromo) in a suitable solvent such as DCM at a suitable temperature such as 0° C. to room temperature. Compounds of Formula (V) may be obtained commercially or by analogy with the methods described herein.

According to a third process, compounds of Formula (III) may be prepared from compounds of Formula (IIIA) as illustrated by Scheme 3 wherein LG is a suitable leaving group such as OH or Hal (wherein Hal is chloro, bromo or iodo).

Scheme 3

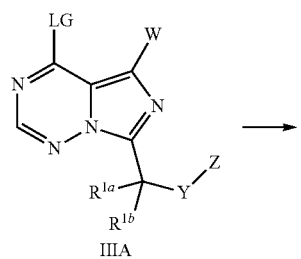

In Scheme 3, compounds of Formula (III) may be prepared from compounds of Formula (IIIA) (where LG is OH) using a suitable functional group inter-conversion reaction such as a two-step process using a suitable halogenation reaction followed by a suitable amination reaction. Preferable chlorination conditions comprise treating a compound of Formula (IIIA) with triazole, phosphorus oxychloride and a suitable base such as $Et_3N$ in a suitable solvent such as DCM at a suitable temperature from 0° C. to 70° C., preferably in DCM at 70° C. in a sealed tube. The intermediate compounds of Formula (IIIB) (where LG=Hal) may be converted into compounds of Formula (III) by treatment with ammonia in dioxane and/or aqueous ammonium hydroxide solution in a suitable solvent at a suitable temperature such as 120° C. for an appropriate time such as 1-18 hours in a sealed tube in the presence or absence of microwave irradiation. The reaction steps depicted in Scheme 3 may be carried out either individually or combined into a single preparation.

According to a fourth process, compounds of Formula (I) may be prepared from compounds of Formulae (IA), (IB), and (IX) and as illustrated by Scheme 4 wherein Hal is chloro, bromo or iodo.

Scheme 4

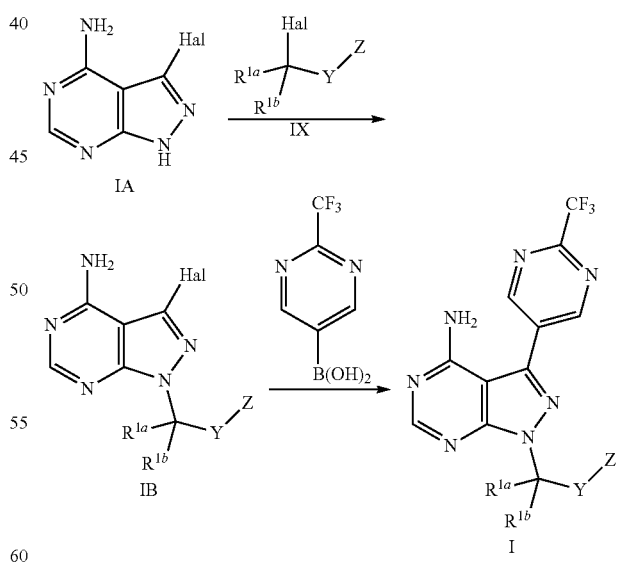

In Scheme 4, compounds of Formula (I) may be prepared from compounds of Formula (IB) and the 2-trifluoromethylpyrimidinyl boronate shown using a suitable organometallic cross-coupling reaction such as Suzuki cross-coupling reaction. Typical Suzuki cross-coupling conditions comprise a palladium catalyst containing suitable phosphine ligands, in the presence of an inorganic base, in aqueous dioxane, at elevated temperatures either thermally or under microwave irradiation. Preferred conditions comprise Pd(OAc)$_2$, Pd(dppf)Cl$_2$ or Pd(PPh$_3$)$_4$ with either sodium, cesium or potassium carbonate in aqueous dioxane or methanol at from room temperature to 120° C. The compounds of Formula (IB) may be prepared by a suitable alkylation reaction using compounds of Formula (IA) and (IX) in the presence of a suitable base such as Cs$_2$CO$_3$ in a suitable solvent such as DMF at a suitable temperature from room temperature to 100° C. Compounds of Formula (IA) may be obtained commercially or by analogy with the methods described herein.

According to a fifth process, compounds of Formula (IIA') may be prepared from compounds of Formulae (IIG), (IIF), (IID"), (IID'), (IIE'), (V) and (XII) and as illustrated by Scheme 5 wherein Hal is chloro, bromo or iodo.

using a suitable organometallic reagent such as a Grignard reagent such as isopropylmagnesium chloride lithium chloride complex in a suitable solvent such as THF at a suitable temperature from −30° C. to room temperature followed by addition of a suitable carbonyl compound of Formula (XII). Compounds of Formula (IIF) may be prepared from compounds of Formula (IIG) and excess dimethylformamide dimethylacetal at a suitable temperature such as 90° C. for a suitable time such as 2-18 hours. Compounds of Formula (IIG) may be obtained commercially or by analogy with the methods described herein.

According to a sixth process, compounds of Formula (IXA) and (XII) may be prepared from compounds of Formulae (XIII) and (XIV) and as illustrated by Scheme 6.

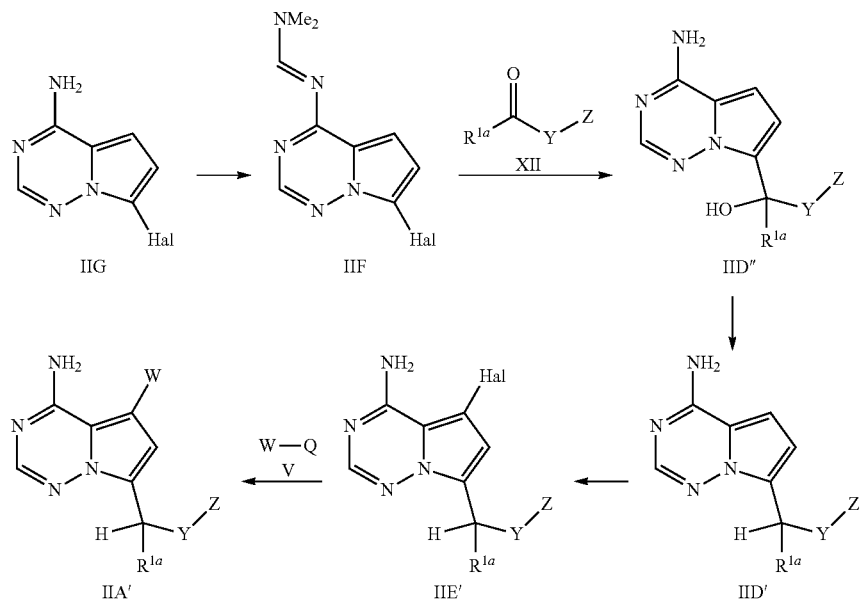

In Scheme 5, compounds of Formula (IIA') may be prepared from compounds of Formulae (IID'), (IIE') and (V) using a suitable halogenation and organometallic cross-coupling reaction such as Suzuki cross-coupling reaction preceded if necessary by a boronic acid or ester formation in an analogous fashion to that described in Scheme 2. Compounds of Formula (IID') may be prepared from compounds of Formula (IID") using a suitable reagent such as a Et$_3$SiH in the presence of TFA in a suitable solvent such as DCM at a suitable temperature such as 0° C. to room temperature for an appropriate time of 1-18 hours. Alternatively, compounds of Formula (IID") may be prepared from compounds of Formula (IIF) and a suitable aldehyde (XII) (where R$^{1a}$=H). Compounds of Formula (IID") may be prepared from a compound of Formula (XI) and an aldehyde of (XII) using a suitable alkylation reaction. Compounds of Formula (IIF) may undergo a suitable halogen-metal exchange reaction

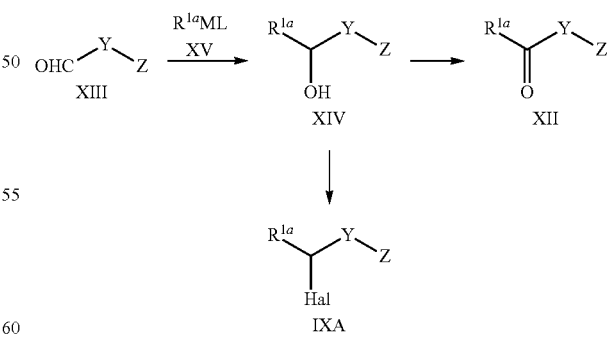

In Scheme 6, compounds of Formula (XIV) may be prepared from compounds of Formulae (XIII) using a suitable nucleophilic-carbon compound of Formula (XV) such as a suitable Grignard reagent (where M is Mg, L is Hal) in a suitable solvent such as THF at a suitable temperature such as 0° C. to room temperature. Compounds of Formula (XII)

may be prepared from compounds of Formula (XIV) by oxidation using a suitable reagent such as MnO$_2$ in a suitable solvent such as DCM at a suitable temperature such as room temperature to reflux. Compounds of Formula (IXA) may be prepared from compounds of Formula (XIV) using a suitable halogenation reagent such as thionyl chloride (Hal=Cl) in a suitable solvent such as DCM at a suitable temperature such as room temperature. Compounds of Formula (XIII) may be obtained commercially or by analogy with the methods described herein.

In Scheme 7, compounds of Formula (IIA″) may be prepared from compounds of Formulae (IID″), (IIE″) and (V) using a suitable halogenation and organometallic cross-coupling reaction such as Suzuki cross-coupling reaction preceded if necessary by a boronic acid or ester formation in an analogous fashion the methods in Scheme 2.

According to an eighth process, compounds of Formula (IIIA′) may be prepared from compounds of Formulae (XVI), (XVII), (XVIII), (XIX), (XX), (XXI) and (XXII) as illustrated in Scheme 8 wherein Hal is chloro, bromo or iodo and Rx is a suitable alkyl group such as methyl or ethyl.

Scheme 8

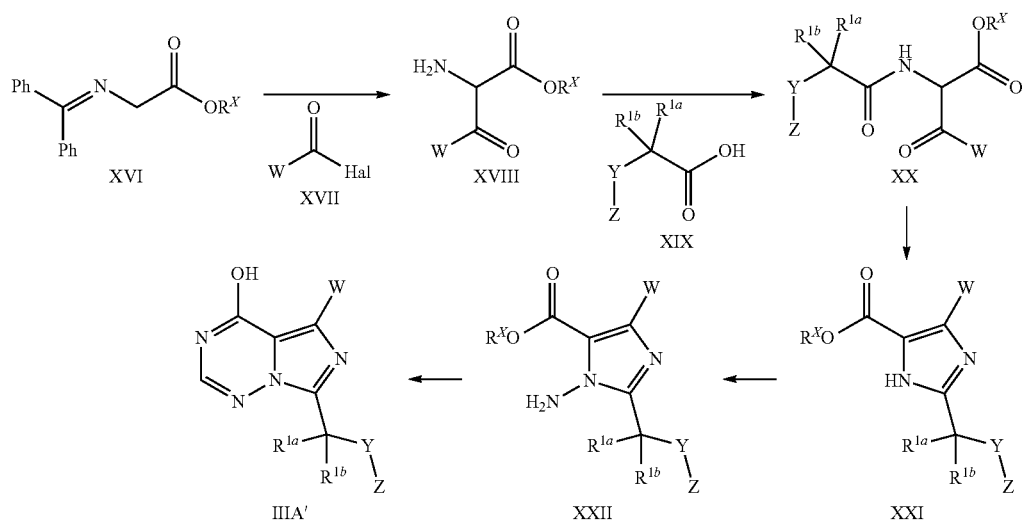

According to a seventh process, compounds of Formula (IIA″) (a compound of Formula (II) where R$^{1b}$=OH) may be prepared from compounds of Formulae (IID″), (IIE″) and (V) and as illustrated in Scheme 7 wherein Hal is chloro, bromo or iodo.

Scheme 7

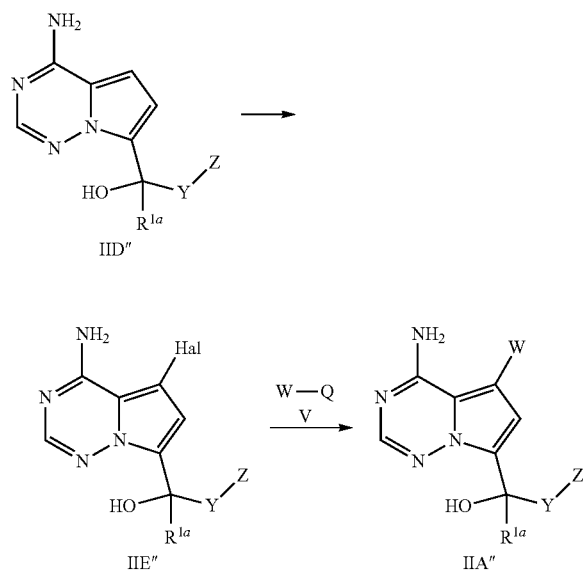

In Scheme 8, compounds of Formula (IIIA′) may be prepared by heating compounds of Formula (XXII), formamide and formamidine acetate in a sealed tube at a suitable temperature such as 130° C. under microwave irradiation for a suitable time such as 2 hours. A person skilled in the art will appreciate that there are alternative suitable methods to elicit heterocycle formation. Compounds of Formula (XXII) may be prepared from compounds of Formula (XXI) and O(diphenylphosphinyl)hydroxylamine in the presence of a suitable base such as LiHMDS in a suitable solvent such as DMF at a suitable temperature such as 0° C. to room temperature for a suitable time such as 18 hours. Compounds of Formula (XXI) may be prepared by heating compounds of Formula (XX) and ammonium acetate in acetic acid in a sealed tube under microwave irradiation at a suitable temperature such as 130° C. Compounds of Formula (XX) may be prepared from compounds of Formula (XVIII) and (XIX) using an amide bond formation step mediated by a suitable combination of amide bond coupling agent and organic base. Preferred conditions comprise HATU with NMM in a suitable solvent such as DMF at room or elevated temperatures. Compounds of Formula (XVIII) may be prepared from compounds of Formula (XVI) and (XVII) in the presence of a suitable base such as KOtBu in a suitable solvent such as THF at a suitable temperature such as −70° C. to −50° C. followed by treatment with conc. HCl. Compounds of Formulae (XVI), (XVII) and (XIX) may be obtained commercially or by analogy with the methods described herein.

According to a ninth process, compounds of Formula (IID‴) may be prepared from compounds of Formulae (XV), (XXIII), (XXIV), (XXV), (XXVI), (XXVII), (XXVIII) and (XXIX) and as illustrated in Scheme 9 wherein PG is a suitable nitrogen protecting group (e.g. tBoc).

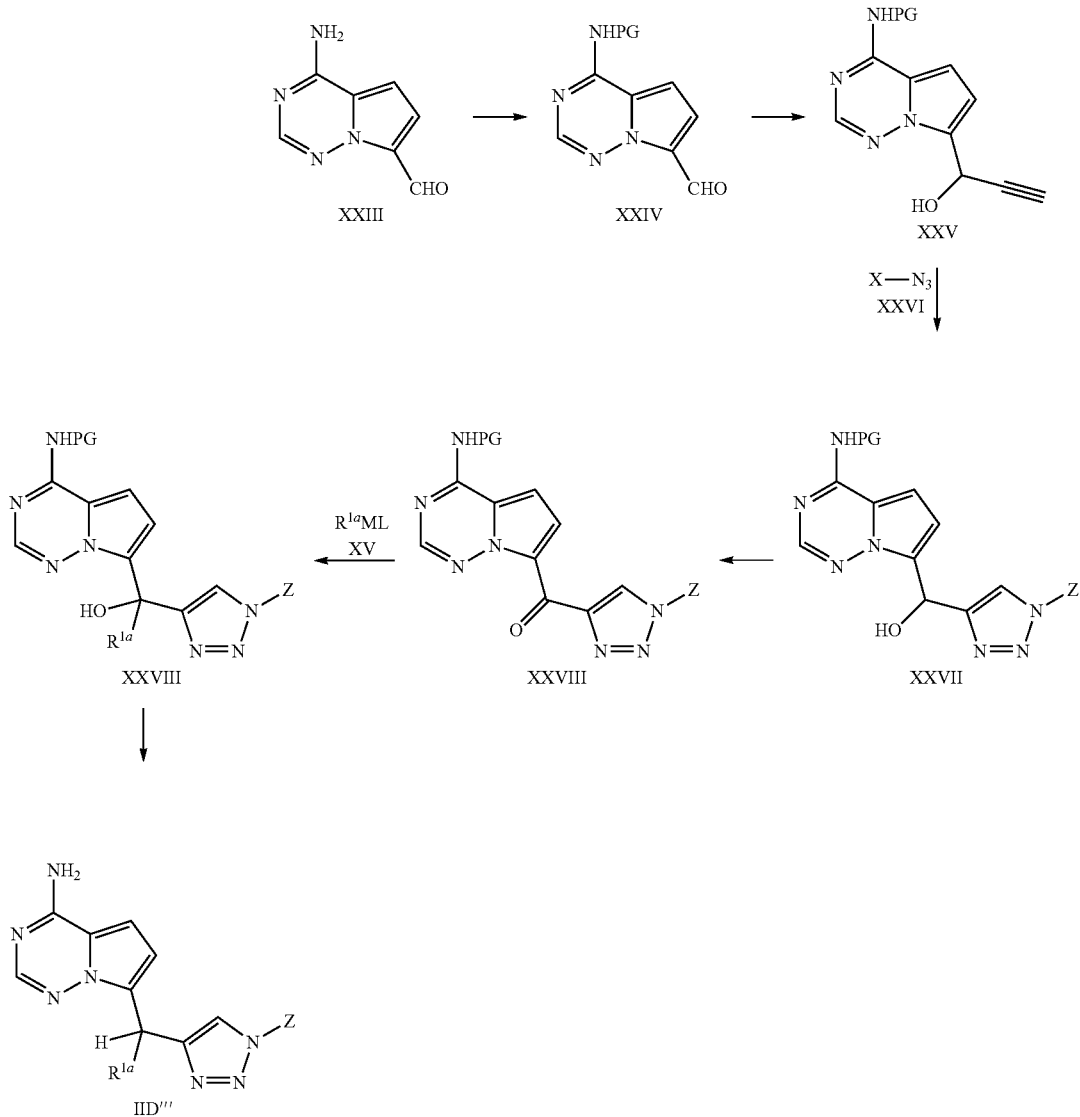

In Scheme 9, compounds of Formula (IID''') may be prepared from compounds of Formula (XXIX) using a suitable reagent such as Et₃SiH in the presence of TFA in a suitable solvent such as DCM at a suitable temperature such as 0° C. to room temperature for an appropriate time of 1-18 hours. Compounds of Formula (XXIX) may be prepared from compounds of Formula (XXVIII) using a suitable nucleophilic-carbon compound of Formula (XV) such as a suitable Grignard reagent (where M is Mg, L is Hal) in a suitable solvent such as THF at a suitable temperature such as 0° C. to room temperature. Compounds of Formula (XXVIII) may be prepared from compounds of Formula (XXVII) using a suitable oxidation using a suitable reagent such as MnO₂ in a suitable solvent such as DCM at a suitable temperature such as room temperature to reflux. Compounds of Formula (XXVII) may be prepared from compounds of Formulae (XXV) and (XXVI) in the presence of a suitable base such as DIPEA in suitable solvent such as toluene and ᵗBuOH at a suitable temperature such as room temperature. Compounds of Formula (XXV) may be prepared from compounds of Formula (XXIV) and ethynylmagnesium bromide in a suitable aprotic solvent such as THF at a suitable temperature such as 0° C. to room temperature. Compounds of Formula (XXIV) may be prepared from compounds of Formula (XXIII) and (Boc)₂O in the presence of DMAP in a suitable solvent such as DCM at a suitable temperature such as room temperature. Compounds of Formulae (XV), (XXIII), and (XXVI) may be obtained commercially or by analogy with the methods described herein.

According to a tenth process, compounds of Formula (I') may be prepared from compounds of Formulae (IA), (XXX), (XXXI), and (IB') and the 2-trifluoromethyl pyrimidinyl boronate as illustrated in Scheme 10 wherein Hal is chloro, bromo or iodo.

Scheme 10

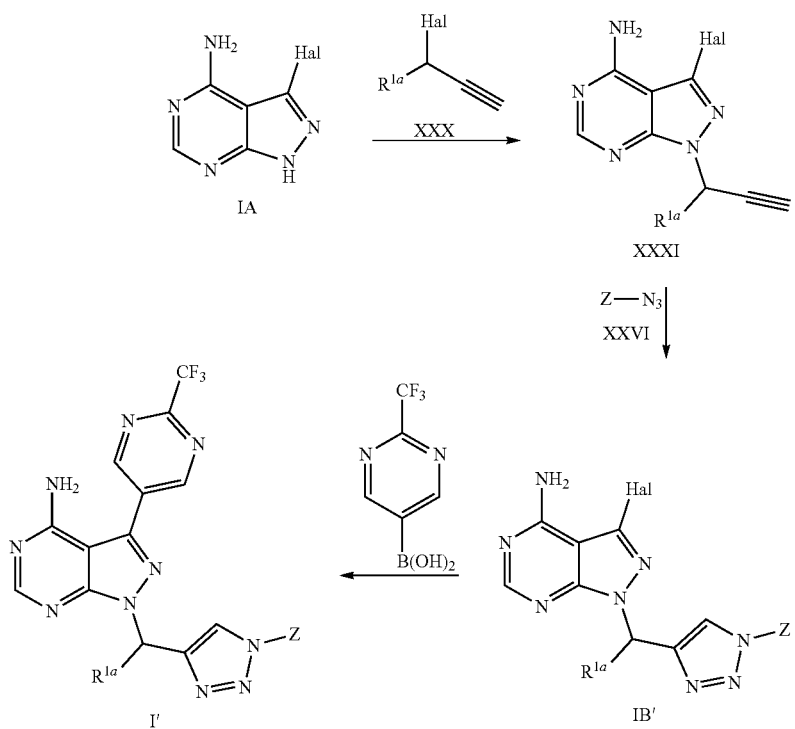

In Scheme 10, compounds of Formula (I') may be prepared from compounds of Formula (IB') and a suitable 2-trifluoromethyl pyrimidinyl boronate using a suitable organometallic cross-coupling reaction such as Suzuki cross-coupling reaction. Typical Suzuki cross-coupling conditions comprise a palladium catalyst containing suitable phosphine ligands, in the presence of an inorganic base, in aqueous dioxane, at elevated temperatures either thermally or under microwave irradiation. Preferred conditions comprise Pd(OAc)$_2$, Pd(dppf)Cl$_2$ or Pd(PPh$_3$)$_4$ with either sodium, cesium or potassium carbonate in aqueous dioxane or methanol at from room temperature to 120° C. Compounds of Formula (IB') may be prepared from compounds of Formulae (XXXI) and (XXVI) in the presence of a suitable base such as DIPEA in suitable solvent such as toluene and $^t$BuOH at a suitable temperature such as room temperature. Compounds of Formula (XXXI) may be prepared from compounds of Formulae (XXX) and (IA) in the presence of a suitable base such as Cs$_2$CO$_3$ in a suitable solvent such as DMF at a suitable temperature such as room temperature. Compounds of Formulae (IA), and (XXVI) may be obtained commercially or by analogy with the methods described herein.

In the case of compounds described in all of the preceding general method schemes where R$^{1a}$ and R$^{1b}$ are different groups (for example where R$^{1a}$ is (C$_1$-C$_3$)alkyl and R$^{1b}$ is H) leading to the presence of a chiral center it is well understood by a skilled person that the individual enantiomers can be obtained using a suitable separation method such as SFC chromatography to afford both the (+) and (−)-enantiomers of these compounds. It is well understood by a skilled person that an individual enantiomer of a compound described in the preceding general method schemes is prepared and isolated as described above or isolated using an alternative separation technique such as HPLC using a suitable chiral stationary phase eluting with a suitable mobile phase as determined to be necessary to isolate the required enantiomers.

The following non-limiting Preparations and Examples illustrate the preparation of compounds and salts of the present invention. In the Examples and Preparations that are set out below, and in the aforementioned Schemes, the following abbreviations, definitions and analytical procedures may be referred to. Other abbreviations common in the art are also used. Standard IUPAC nomenclature has been used.

The following abbreviations may be used: AcOH is acetic acid; Ar is argon; aq is aqueous; Bn is benzyl; Boc is tert-butoxy carbonyl; Boc$_2$O is di-tert-butyl dicarbonate; br is broad; tBu is tert-butyl; tBuOH is tert-butanol; n-BuLi is n-butyl lithium; Bu$_4$NCl is tetrabutyl ammonium chloride; ° C. is degrees Celsius; CDCl$_3$ is deutero-chloroform; Cs$_2$CO$_3$ is cesium carbonate; CsF is cesium fluoride; CuCN is copper cyanide; CuI is copper iodide; δ is chemical shift; d is doublet; DCM is dichloromethane or methylene chloride; DIAD is diisopropyl azodicarboxylate; DIPEA is N-ethyl-diisopropylamine or N,N-diisopropylethylamine; DMA is N,N-dimethyl acetamide; DMAP is 4-dimethyl aminopyridine; DMF is N,N-dimethylformamide; DMF-DMA is N,N-dimethylformamide dimethyl acetal; DMSO is dimethyl sulfoxide; DPPA is diphenyl phosphoryl azide; Dppf is 1,1'-bis(diphenylphosphino)ferrocene; EDA is ethylenediamine; Et$_2$O is diethyl ether; EtOAc is ethyl acetate; EtOH is ethanol; Et$_3$N is triethylamine; Et$_3$SiH is triethylsilane; g is gram; HATU is 1-[Bis(dimethylamino) methylene]-1H-1,2,3-triazolo[4,5-b]pyridinium 3-oxid hexafluorophosphate; HCl is hydrochloric acid; HCO$_2$H is formic acid; HPLC is high pressure liquid chromatography; H$_2$ is hydrogen; H$_2$O is water; Hr is hour, hrs are hours; $K_2CO_3$ is potassium carbonate; $KHSO_4$ is potassium hydrogen sulfate; KOAc is potassium acetate; $K_3PO_4$ is potassium phosphate; L is liter; LCMS is liquid chromatography mass spectrometry; LDA is lithium diisopropylamide; $LiAlH_4$ or LAH is lithium aluminium hydride; LiCl is lithium chloride; LiHMDS is lithium bis(trimethylsilyl)amide; $LiOH.H_2O$ is lithium hydroxide monohydrate; Li-Selectride® is lithium tri-sec-butylborohydride; m is multiplet; M is molar; MeCN is acetonitrile; MeMgBr is methyl magnesium bromide; MeOH is methanol; 2-MeTHF is 2-methyl tetrahydrofuran; mg is milligram; $MgSO_4$ is magnesium sulfate; MHz is mega Hertz; min is minutes; mL is milliliter; mmol is millimole; $MnO_2$ is manganese dioxide; mol is mole; MS m/z is mass spectrum peak; MTBE is tert-butyl methyl ether; MsCl is mesyl chloride; NaCN is sodium cyanide; $NaBH_4$ is sodium borohydride; $Na_2CO_3$ is sodium carbonate; NaH is sodium hydride; $NaHCO_3$ is sodium hydrogen carbonate; $NaHSO_4$ is sodium hydrogen sulfate; NaHMDS is sodium bis(trimethylsilyl)amide; NaOH is sodium hydroxide; NaOAc is sodium acetate; NaOMe is sodium methoxide; $Na_2SO_4$ is sodium sulfate; $Na_2S_2O_3$ is sodium thiosulfate; NBS is N-bromo succinimide; NCS is N-chlorosuccinimide; $NH_3$ is ammonia; $NH_4Cl$ is ammonium chloride; $NH_4HCO_3$ is ammonium hydrogen carbonate; $NH_2NH_2.H_2O$ is hydrazine hydrate; $NH_2OH.HCl$ is hydroxylamine hydrochloride; $NH_4OH$ is ammonium hydroxide; $NH_4OAc$ is ammonium acetate; NiI is nickel iodide; NIS is N-iodosuccinimide; nM is nanomolar; NMP is 1-methyl-2-pyrrolidinone; NMR is nuclear magnetic resonance; Pd/C is palladium on carbon; $Pd_2(dba)_3$ is Tris(dibenzylideneacetone)dipalladium; $Pd(dppf)Cl_2$ is [1,1'-bis(diphenylphosphino) ferrocene]dichloropalladium(II); $Pd(OH)_2$ is palladium hydroxide; $Pd(OAc)_2$ is palladium acetate; $PPh_3$ is triphenylphosphine; $Pd(PPh_3)_4$ is tetrakis (triphenylphosphine) palladium (0); Pet. Ether is petroleum ether; pH is power of hydrogen; ppm is parts per million; $PtO_2$ is platinum (IV) oxide; q is quartet; rt is room temperature; RT is retention time; s is singlet; SCX is strong cation exchange; SEM-Cl is 2-(trimethylsilyl) ethoxymethyl chloride; SFC is supercritical fluid chromatography; SM is starting material; S-Phos is 2-dicyclohexylphosphino-2',6'-dimethoxybiphenyl; $SOCl_2$ is thionyl chloride; t is triplet; T3P is propylphosphonic anhydride; TBAF is tert-butyl ammonium fluoride; TBD is 1,5,7-triazabicyclo[4.4.0]dec-5-ene; TBME is tert-butyl dimethyl ether; TFA is trifluoroacetic acid; TFP is tri(2-furyl)phosphine; THF is tetrahydrofuran; $Ti(OiPr)_4$ is titanium (IV) isopropoxide; TPTU is 2-(2-pyridon-1-yl)-1,1,3,3-tetramethyluronium tetrafluoroborate; µL is microliter; µmol is micromole; XPhos is 2-dicyclohexyl phosphino-2',4',6'-trisopropylbiphenyl; and $Zn(CN)_2$ is Zinc cyanide.

$^1H$ and $^{19}F$ Nuclear magnetic resonance (NMR) spectra were in all cases consistent with the proposed structures. Characteristic chemical shifts (δ) are given in parts-per-million downfield from tetramethylsilane (for $^1H$-NMR) and upfield from trichloro-fluoro-methane (for $^{19}F$ NMR) using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; DMSO-$d_6$, deuterodimethylsulfoxide; and MeOH-$d_4$, deuteromethanol. Where appropriate, tautomers may be recorded within the NMR data; and some exchangeable protons may not be visible.

Mass spectra, MS (m/z), were recorded using either electrospray ionisation (ESI) or atmospheric pressure chemical ionisation (APCI).

Where relevant and unless otherwise stated the m/z data provided are for isotopes $^{19}F$, $^{35}Cl$, $^{79}Br$ and $^{127}I$.

Wherein preparative TLC or silica gel chromatography has been used, one skilled in the art may choose any combination of appropriate solvents to purify the desired compound.

The following are analytical and preparative chromatography methods used for the analysis and purification of intermediates and compounds of the invention.

Preparative SFC Methods
SFC Method F1:
Column: CHIRALPAK ID, 5.0 cm I.D.×25 cm long; Isocratic Mobile Phase: Hexane/EtOAc/DEA, 60/40/0.1 (v/v/v); Flow rate: 60 mL/min; Temperature: 35° C.

Analytical SFC Methods
SFC Method F2:
Column: CHIRALPAK ID, 0.46 cm I.D.×15 cm long; Mobile phase: Hexane/EtOAc/DEA, 60/40/0.1 (v/v/v); Flow rate: 1.0 mL/min; Wave length: UV 214 nm; Temperature: 35° C.

Preparative HPLC Methods
HPLC Method B2:
Column: CHIRALCEL OJ-H 2.5 cm I.D.×25 cm long; Isocratic Mobile Phase: MeOH/DEA, 100/0.1 (v/v); Flow rate: 30 mL/min; Temperature: 35° C.

HPLC Method C20A:
Column: CHIRALPAK IC, 2.5 cm I.D.×25 cm long; Isocratic Mobile Phase: DCM/MeOH, 95/5 (v/v); Flow rate: 30 mL/min; Temperature: 35° C.

HPLC Method C20B:
Column: CHIRALPAK IC, 5.0 cm I.D.×25 cm long; Isocratic Mobile Phase: DCM/MeOH, 95/5 (v/v); Flow rate: 60 mL/min; Temperature: 35° C.

HPLC Method C22A:
Column: CHIRALPAK IC, 2.5 cm I.D.×25 cm long; Isocratic Mobile Phase: DCM/MeOH/DEA, 95/5/0.1 (v/v/v); Flow rate: 30 mL/min; Temperature: 35° C.

HPLC Method C22B:
Column: CHIRALPAK IC, 5.0 cm I.D.×25 cm long; Isocratic Mobile Phase: DCM/MeOH/DEA, 95/5/0.1 (v/v/v); Flow rate: 30 mL/min; Temperature: 35° C.

HPLC Method C23A:
Column: CHIRALPAK IC, 5.0 cm I.D.×25 cm long; Isocratic Mobile Phase: DCM/EtOH, 90/10 (v/v); Flow rate: 60 mL/min; Temperature: 35° C.

HPLC Method C23B:
Column: CHIRALPAK IC, 2.5 cm I.D.×25 cm long; Isocratic Mobile Phase: DCM/EtOH, 90/10 (v/v); Flow rate: 60 mL/min; Temperature: 35° C.

HPLC Method C24A:
Column: CHIRALPAK IC, 5.0 cm I.D.×25 cm long; Isocratic Mobile Phase: DCM/EtOH, 95/5 (v/v); Flow rate: 60 mL/min; Temperature: 35° C.

HPLC Method C24B:
Column: CHIRALPAK IC, 2.5 cm I.D.×25 cm long; Isocratic Mobile Phase: DCM/EtOH, 95/5 (v/v); Flow rate: 60 mL/min; Temperature: 35° C.

HPLC Method C27:
Column: CHIRALPAK IC, 5.0 cm I.D.×25 cm long; Isocratic Mobile Phase: Hexane/EtOAc/DEA, 60/40/0.1 (v/v/v); Flow rate: 60 mL/min; Temperature: 35° C.

HPLC Method C28:
Column: CHIRALPAK IC, 2.5 cm I.D.×25 cm long; Isocratic Mobile Phase: Hexane/EtOH, 85/15 (v/v); Flow rate: 30 mL/min.
HPLC Method D4:
Column: CHIRALPAK AD-H, 25 cm I.D.×250 cm long; Isocratic Mobile Phase: EtOH/MeCN, 80/20 (v/v); Flow rate: 20 mL/min; Temperature: 35° C.
HPLC Method D5:
Column: CHIRALPAK AD-H, 2.5 cm I.D.×25 cm long; Isocratic Mobile Phase: Hexane/EtOH, 70/30 (v/v); Flow rate: 30 mL/min; Temperature: 35° C.
HPLC Method D6:
Column: CHIRALPAK AD-H, 2.5 cm I.D.×25 cm long; Isocratic Mobile Phase: MeOH/MeCN, 90/10 (v/v); Flow rate: 30 mL/min.
HPLC Method D7:
Column: CHIRALPAK AD-H, 5.0 cm I.D.×25 cm long; Isocratic Mobile Phase: Hexane/IPA, 70/30 (v/v); Flow rate: 60 mL/min.
HPLC Method E3:
Column: CHIRALPAK IE, 2.5 cm I.D.×25 cm long; Isocratic Mobile Phase: Hexane/EtOH, 70/30, (v/v); Flow rate: 60 mL/min; Temperature: 35° C.
HPLC Method E4:
Column: CHIRALPAK IE, 5.0 cm I.D.×25 cm long; Isocratic Mobile Phase: DCM/EtOH, 95/5 (v/v); Flow rate: 55 mL/min; Temperature: 35° C.
HPLC Method E5:
Column: CHIRALPAK IE 5.0 cm I.D.×25 cm long; Isocratic Mobile Phase: Hexane/EtOH, 80/20 (v/v); Flow rate: 60 mL/min; Temperature: 35° C.
HPLC Method G1:
Column: Waters Sunfire C18 (19×100 mm, 5p); Mobile Phase: MeCN(0.05% TFA)-Water(0.05% TFA); Gradient: 20%-60% MeCN over 8.5 min, 60%-100% MeCN over 0.5 min, hold at 100% MeCN for 1 min; Flow rate: 25 mL/min.

Analytical HPLC Methods
HPLC Method A:
Column: Acquity BEH C18 50×2.1 mm, 1.7µ; Mobile Phase: MeCN(0.05% TFA)-Water(0.05% TFA); Gradient: 5%-95% MeCN over 2 min, hold at 95% MeCN for 0.5 min.; re-equilibrate back to 5% MeCN to 2.7 min.; Flow rate: 0.8 mL/min; Temperature: 45° C.
HPLC Method B1:
Column: CHIRALCEL OJ-H, 0.46 cm I.D.×15 cm long; Injection: 20.0 ul; Mobile Phase: MeOH/MeCN, 90/10(v/v); Flow rate: 1.0 mL/min; Wave length: UV 254 nm; Temperature: 35° C.
HPLC-Method C1:
Column: CHIRALPAK IC, 0.46 cm I.D.×25 cm long; Mobile Phase: DCM/EtOH, 95/5(v/v); Flow rate: 1.0 mL/min; Wave length: UV 214 nm; Temperature: 25° C.
HPLC-Method C2:
Column: CHIRALPAK IC, 0.46 cm I.D.×15 cm long; Mobile Phase: DCM/EtOH, 95/5 (v/v); Flow rate: 1.0 mL/min; Wave length: UV 214 nm; Temperature: 25° C.
HPLC-Method C4:
Column: CHIRALPAK IC, 0.46 cm I.D.×25 cm long; Mobile Phase: DCM/MeOH, 95/5 (v/v); Flow rate: 1.0 mL/min; Wave length: UV 254 nm; Temperature: 25° C.
HPLC-Method C5:
Column: CHIRALPAK IC, 0.46 cm I.D.×15 cm long, 5µ; Mobile Phase: DCM/MeOH, 95/5(v/v); Flow rate: 1.0 mL/min; Wave length: UV 254 nm; Temperature: 35° C.

HPLC Method C10:
Column: CHIRALPAK IC, 0.46 cm I.D.×15 cm long; Mobile Phase: DCM/EtOH/DEA, 90/10/0.1(v/v); Flow rate: 1.0 mL/min; Wave length: UV 254 nm; Temperature: 25° C.
HPLC Method C12:
Column: CHIRALPAK IC, 0.46 cm I.D.×15 cm long; Mobile Phase: Hexane/EtOH, 85/15 (v/v); Flow rate: 1.0 mL/min; Wave length: UV 214 nm; Temperature: 35° C.
HPLC Method C13:
Column: CHIRALPAK IC, 0.46 cm I.D.×15 cm long; Mobile phase: Hexane/EtOAc/DEA, 60/40/0.1 (v/v/v); Flow rate: 1.0 mL/min; Wave length: UV 214 nm; Temperature: 35° C.
HPLC Method C14:
Column: CHIRALPAK IC, 0.46 cm I.D.×15 cm long; Mobile Phase: Hexane/EtOH, 80/20 (v/v); Flow rate: 1.0 mL/min; Wave length: UV 214 nm; Temperature: 35° C.
Method D1:
Column: CHIRALPAK AD-H, 0.46 cm I.D.×15 cm long; Mobile Phase: EtOH/MeCN, 80/20 (v/v); Flow rate: 1.0 mL/min; Wave length: UV 214 nm; Temperature: 35° C.
Method D2:
Column: CHIRALPAK AD-H, 0.46 cm ID×15 cm long; Mobile Phase: Hexane/EtOH, 70/30 (v/v); Flow rate: 1.0 mL/min; Wave length: UV 214 nm; Temperature: 35° C.
Method E1:
Column: CHIRALPAK IE, 0.46 cm I.D.×15 cm long; Mobile Phase: Hexane/EtOH, 70/30 (v/v); Flow rate: 1.0 mL/min; Wave length: UV 214 nm; Temperature: 25° C.
HPLC Method G2:
Column: Waters Atlantis dC18 (4.6×50 mm, 5µ); Mobile Phase: MeCN(0.05% TFA)-Water(0.05% TFA); Gradient: 5%-95% MeCN over 4 min, hold at 95% MeCN for 1 min; Flow rate: 2 mL/min.

Preparation of Intermediates

Preparation 1: 5-Bromo-7-{[1-(2-fluorophenyl)-1H-1,2,3-triazol-4-yl]methyl}pyrrolo[2,1-f][1,2,4]triazin-4-amine

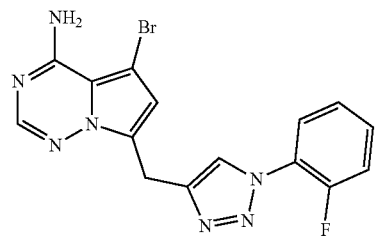 [SMILES: Nc1ncnn2c(Cc3cn(-c4ccccc4F)nn3)cc(Br)c12]

To a solution of 7-{[1-(2-fluorophenyl)-1H-1,2,3-triazol-4-yl]methyl}pyrrolo[2,1-f][1,2,4]triazin-4-amine (Preparation 45, 1.2 g, 3.88 mmol) in DCM (35 mL) was added NBS (0.76 g, 4.27 mmol) portion wise at 0° C. and the reaction mixture was stirred at 0° C. for 1 hr. The mixture was poured into water and the resulting white solid was filtered off, and dried under vacuum to afford the title product as a white solid (1.3 g, 86%). $^1$HNMR (400 MHz, CDCl$_3$): 4.47 (s, 2H), 6.19 (br s, 2H), 6.64 (s, 1H), 7.27-7.33 (m, 2H), 7.43 (m, 1H), 7.92-7.98 (m, 3H). LCMS m/z=388.0 [MH]$^+$

Preparation 2: 5-Bromo-7-{[1-(2-fluorophenyl)-1H-1,2,3-triazol-4-yl]ethyl}pyrrolo[2,1-f][1,2,4]triazin-4-amine

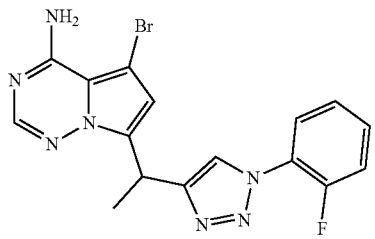 [SMILES: CC(c1cn(-c2ccccc2F)nn1)c1cc(Br)c2c(N)ncnn12]

To a stirred solution of 7-{[1-(2-fluorophenyl)-1H-1,2,3-triazol-4-yl]ethyl}pyrrolo[2,1-f][1,2,4]triazin-4-amine (Preparation 17, 220 mg, 0.68 mmol) in DMF (2 mL) and DCM (10 mL) was added NBS (115 mg, 0.64 mmol) in portions at 0° C. and the resulting reaction was stirred at 0° C. for 20 mins. The mixture was quenched with 5% $Na_2S_2O_3$ aqueous solution (10 mL), the layers separated and the aqueous extracted with DCM (10 mL×2). The combined organic extracts were dried ($Na_2SO_4$), filtered and the filtrate concentrated in vacuo. The residue was purified by preparative HPLC eluting with MeCN:$H_2O$ (0.1% TFA) (40:60 to 50:50) to afford the title compound as a white solid (260 mg, 98%). $^1$HNMR (400 MHz, DMSO-$d_6$): 1.69 (d, 3H), 4.88 (q, 1H), 6.68 (s, 1H), 6.70-6.80 (br s, 1H), 7.40 (m, 1H), 7.52-7.62 (m, 2H), 7.78 (m, 1H), 7.95 (s, 1H), 7.98-8.15 (br s, 1H), 8.41 (s, 1H). LCMS m/z=402.1, 404.1 [MH]$^+$

Preparation 3: 5-Bromo-7-{[1-(2,4-Difluorophenyl)-1H-1,2,3-triazol-4-yl]propyl}pyrrolo[2,1-f][1,2,4]triazin-4-amine

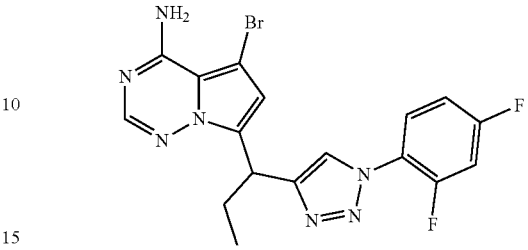

The title compound was obtained as a white solid (310 mg, 52%) from 7-{[1-(2,4-difluorophenyl)-1H-1,2,3-triazol-4-yl]propyl}pyrrolo[2,1-f][1,2,4]triazin-4-amine (Preparation 20) following an analogous procedure to that described in preparation 2. $^1$HNMR (400 MHz, DMSO-$d_6$): 0.87 (t, 3H), 2.10 (m, 2H), 4.72 (m, 1H), 6.81 (br s, 1H), 7.31 (m, 1H), 7.64 (m, 1H), 7.85-7.95 (m, 2H), 8.46 (s, 1H). LCMS m/z=434.1, 436.1 [MH]$^+$ Preparations 4 to 16

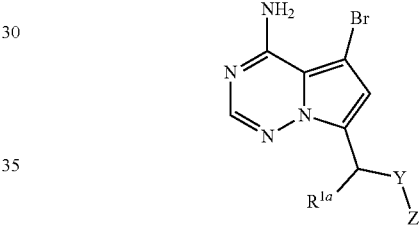

NBS (0.9-1.0 eq) was added portion wise to an ice-cooled solution of the appropriate starting material (1 eq) in DCM and the resulting mixture stirred at 0° C. for 15-60 minutes, until all starting material had been consumed. The mixture was quenched by the addition of 5% $Na_2S_2O_3$ solution and extracted with DCM (3×). The combined organic extracts were dried ($Na_2SO_4$), filtered and the filtrate evaporated under reduced pressure. The residue was purified by column chromatography eluting with EtOAc:pet. ether or DCM:MeOH at a suitable gradient to afford the desired compound.

| Prep. No. | $R^{1a}$CH—Y—Z | Starting Material | Analytical Data |
|---|---|---|---|
| 4 | ![structure] | 7-{1-[1-(2,4-difluorophenyl)-1H-1,2,3-triazol-4-yl]ethyl}pyrrolo[2,1-f][1,2,4]triazin-4-amine (Preparation 18) | LCMS m/z = 420.1, 422.1 [MH]$^+$; RT [HPLC Method A] = 1.725 min. |
| 5 | ![structure] | 7-{1-[1-(2-fluorophenyl)-1H-1,2,3-triazol-4-yl]propyl}pyrrolo[2,1-f][1,2,4]triazin-4-amine (Preparation 19) | LCMS m/z = 416.0, 418.0 [MH]$^+$; RT [HPLC Method A] = 1.688 min. |

| Prep. No. | R¹ᵃCH—Y—Z | Starting Material | Analytical Data |
|---|---|---|---|
| 6ᵃ | [structure: butyl-triazole-2,5-difluorophenyl] | 7-{1-[1-(2,5-difluorophenyl)-1H-1,2,3-triazol-4-yl]propyl}pyrrolo[2,1-f][1,2,4]triazin-4-amine (Preparation 21) | ¹HNMR (400 MHz, DMSO-d₆): 0.87 (t, 3H), 2.12 (m, 2H), 4.73 (m, 1H), 6.75 (s, 1H), 7.48 (m, 1H), 7.64 (m, 1H), 7.81-7.88 (m, 2H), 8.50 (s, 1H). LCMS m/z = 434.1, 436.1 [MH]⁺ |
| 7ᵃ | [structure: butyl-triazole-3,4-difluorophenyl] | 7-{1-[1-(3,4-difluorophenyl)-1H-1,2,3-triazol-4-yl]propyl}pyrrolo[2,1-f][1,2,4]triazin-4-amine (Preparation 22) | ¹HNMR (400 MHz, DMSO-d₆): 0.88 (t, 3H), 2.11 (m, 2H), 4.69 (m, 1H), 6.74 (s, 1H), 7.63-7.72 (m, 1H), 7.79 (m, 1H), 7.82 (s, 1H), 8.08 (m, 1H), 8.69 (s, 1H). LCMS m/z = 434.1, 436.1 [MH]⁺ |
| 8 | [structure: butyl-pyrazole-isopropyl] | 7-{1-[1-(propan-2-yl)-1H-pyrazol-4-yl]propyl}pyrrolo[2,1-f][1,2,4]triazin-4-amine (Preparation 23) | ¹HNMR (400 MHz, DMSO-d₆): 0.81 (t, 3H), 1.36 (d, 6H), 1.86-1.91 (m, 1H), 1.93-1.98 (m, 1H), 4.34-4.43 (m, 2H), 6.64 (s, 1H), 7.32 (s, 1H), 7.60 (s, 1H), 7.85 (s, 1H). LCMS m/z = 365.0 [MH]⁺; RT [HPLC Method A] = 1.694 min. |
| 9 | [structure: methyl-pyrazole-2-fluorophenyl] | 7-{[1-(2-fluorophenyl)-1H-pyrazol-4-yl]methyl}pyrrolo[2,1-f][1,2,4]triazin-4-amine (Preparation 24) | LCMS m/z = 387.0, 389.0 [MH]⁺ |
| 10 | [structure: ethyl-pyrazole-2-fluorophenyl] | 7-{1-[1-(2-fluorophenyl)-1H-pyrazol-4-yl]ethyl}pyrrolo[2,1-f][1,2,4]triazin-4-amine (Preparation 30) | LCMS m/z = 401.0 [MH]⁺; RT [HPLC Method A] = 1.835 min. |
| 11 | [structure: ethyl-pyrazole-2,4-difluorophenyl] | 7-{1-[1-(2,4-difluorophenyl)-1H-pyrazol-4-yl]ethyl}pyrrolo[2,1-f][1,2,4]triazin-4-amine (Preparation 25) | LCMS m/z = 419.0, 420.0 [MH]⁺ |
| 12 | [structure: propyl-pyrazole-2-fluorophenyl] | 7-{1-[1-(2-fluorophenyl)-1H-pyrazol-4-yl]propyl}pyrrolo[2,1-f][1,2,4]triazin-4-amine (Preparation 26) | LCMS m/z = 416.0, 417.0 [MH]⁺ |
| 13 | [structure: propyl-pyrazole-2,4-difluorophenyl] | 7-{1-[1-(2,4-difluorophenyl)-1H-pyrazol-4-yl]propyl}pyrrolo[2,1-f][1,2,4]triazin-4-amine (Preparation 27) | LCMS m/z = 433.1, 435.1 [MH]⁺ |
| 14ᵇ | [structure: methyl-oxazole-2-fluorophenyl] | 7-{[3-(2-fluorophenyl)-1,2-oxazol-5-yl]methyl}pyrrolo[2,1-f][1,2,4]triazin-4-amine (Preparation 28) | LCMS m/z = 388.0 [MH]⁺ |

-continued

| Prep. No. | R¹ᵃCH—Y—Z | Starting Material | Analytical Data |
|---|---|---|---|
| 15 | 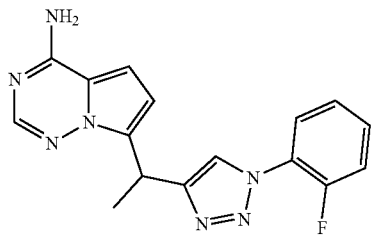 | 7-{1-[3-(2-fluorophenyl)-1,2-oxazol-5-yl]ethyl}pyrrolo[2,1-f][1,2,4]triazin-4-amine (Preparation 29) | LCMS m/z = 404.0 [MH]⁺ |
| 16 | 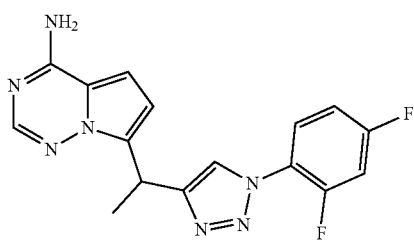 | 1-{4-aminopyrrolo[2,1-f][1,2,4]triazin-7-yl}-1-[1-(2-fluorophenyl)-1H-1,2,3-triazol-4-yl]ethanol (Preparation 31) | LCMS m/z = 418.0, 420.0 [MH]⁺ |

ᵃDMF was used as the reaction solvent instead of DCM, ᵇTHF was used as the reaction solvent

Preparation 17: 7-{[1-(2-Fluorophenyl)-1H-1,2,3-triazol-4-yl]ethyl}pyrrolo[2,1-f][1,2,4]triazin-4-amine A mixture of 1-(4-aminopyrrolo[2,1-f][1,2,4]triazin-7-yl)-1-[1-(2-fluorophenyl)-1H-1,2,3-triazol-4-yl]ethanol (Preparation 31, 400 mg, 1.2 mmol) in Et₃SiH (2 mL) and TFA (6 mL) was stirred at rt for 16 hrs. The mixture was concentrated in vacuo, aq. NaHCO₃ solution (25 mL) was added and the mixture extracted with EtOAc (20 mL×3). The combined organic extracts were dried (Na₂SO₄), filtered and the filtrate concentrated in vacuo. The crude product was purified by column chromatography on silica gel eluting with EtOAc:pet. ether (0:100 to 70:30) to afford the title compound as a white solid (220 mg, 57%). ¹HNMR (400 MHz, DMSO-d₆): 1.72 (d, 3H), 4.88 (q, 1H), 6.58 (d, 1H), 7.05 (s, 1H), 7.40 (m, 1H), 7.54-7.58 (m, 2H), 7.75 (m, 1H), 7.97 (s, 1H), 8.10-8.25 (br s, 2H), 8.37 (s, 1H). LCMS m/z=324.1 [MH]⁺

Preparation 18: 7-{[1-(2,4-Difluorophenyl)-1H-1,2,3-triazol-4-yl]ethyl}pyrrolo[2,1-f][1,2,4]triazin-4-amine To a solution of 1-(4-aminopyrrolo[2,1-f][1,2,4]triazin-7-yl)-1-[1-(2,4-difluorophenyl)-1H-1,2,3-triazol-4-yl]ethanol (Preparation 32, 1.5 g, 4.2 mmol) in DCM (10 mL), was slowly added Et₃SiH (5 mL) and TFA (5 mL) at 0° C. The reaction was stirred at rt for 16 hrs and then concentrated in vacuo. The crude product was purified by column chromatography on silica gel eluting with pet. ether:EtOAc (34:66) to afford the title compound as a yellow solid (1.2 g, 84%). LCMS m/z=342.1 [MH]⁺; RT [HPLC Method A]=1.445 min.

Preparation 19: 7-{[1-(2-Fluorophenyl)-1H-1,2,3-triazol-4-yl]propyl}pyrrolo[2,1-f][1,2,4]triazin-4-amine TFA (3 mL) was slowly added at 0° C. to a solution of tert-butyl (7-{[1-(2-fluorophenyl)-1H-1,2,3-triazol-4-yl]-1-hydroxypropyl}pyrrolo[2,1-f][1,2,4]triazin-4-yl)carbamate (Preparation 44, 1.3 g, 2.87 mmol) in DCM (5 mL). Et₃SiH (3 mL) was slowly added and the reaction mixture was stirred for 16 hr, and then concentrated in vacuo. The residue was dissolved in DCM (15 mL) and the pH adjusted to 8 by the addition of aq. NaHCO₃ solution. The organic phase was dried (Na₂SO₄), the solvents removed under reduced pressure and the crude product purified by column chromatography on silica gel eluting with DCM:MeOH (91:9) to afford the title compound as a yellow solid (0.6 g, 80%). LCMS m/z=338.1, 339.1 [MH]⁺; RT [HPLC Method A]=1.364 min.

Preparations 20 to 29

The following compounds were prepared from the appropriate alcohol starting material, following an analogous procedure to that described in preparation 19.

| Prep. No. | Structure | Starting Material | Starting Material, Yield, data |
|---|---|---|---|
| 20 | 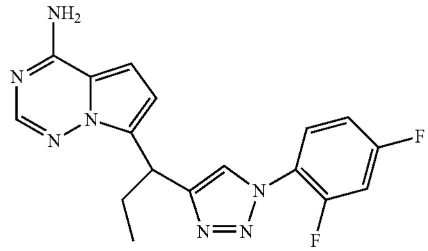 [SMILES: CCC(c1cn(-c2ccc(F)cc2F)nn1)c1ccc2c(N)ncnn12] | 1-(4-aminopyrrolo[2,1-f][1,2,4]triazin-7-yl)-1-[1-(2,4-difluorophenyl)-1H-1,2,3-triazol-4-yl]propan-1-ol (Preparation 33) | LCMS m/z = 356.2 [MH]$^+$; RT [HPLC Method A] = 1.351 min. |
| 21 | 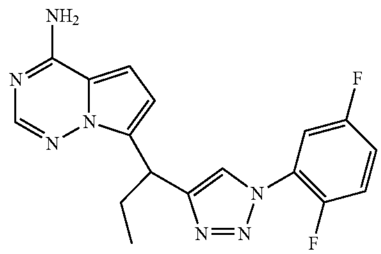 [SMILES: CCC(c1cn(-c2cc(F)ccc2F)nn1)c1ccc2c(N)ncnn12] | 1-(4-aminopyrrolo[2,1-f][1,2,4]triazin-7-yl)-1-[1-(2,5-difluorophenyl)-1H-1,2,3-triazol-4-yl]propan-1-ol (Preparation 34) | LCMS m/z = 356.2 [MH]$^+$ |
| 22 | 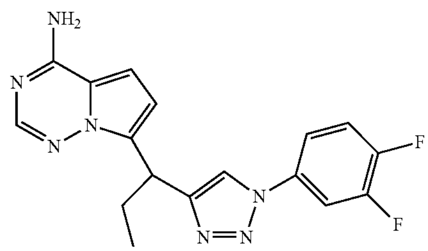 [SMILES: CCC(c1cn(-c2ccc(F)c(F)c2)nn1)c1ccc2c(N)ncnn12] | 1-(4-aminopyrrolo[2,1-f][1,2,4]triazin-7-yl)-1-[1-(3,4-difluorophenyl)-1H-1,2,3-triazol-4-yl]propan-1-ol (Preparation 35) | LCMS m/z = 356.1 [MH]$^+$ |
| 23$^a$ | | 1-(4-aminopyrrolo[2,1-f][1,2,4]triazin-7-yl)-1-[1-(propan-2-yl)-1H-pyrazol-4-yl]propan-1-ol (Preparation 36) | $^1$HNMR (400 MHz, DMSO-d$_6$): 0.81 (t, 3H), 1.36 (d, 6H), 1.91 (m, 1H), 2.01 (m, 1H), 4.33-4.43 (m, 2H), 6.44 (d, 1H), 6.82 (d, 1H), 7.29 (s, 1H), 7.56 (m, 3H), 7.81 (s, 1H). LCMS m/z = 285.2 [MH]$^+$ |
| 24 | 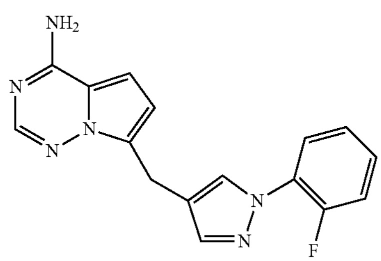 [SMILES: Nc1ncnn2c(Cc3cnn(-c4ccccc4F)c3)ccc12] | (4-aminopyrrolo[2,1-f][1,2,4]triazin-7-yl)[1-(2-fluorophenyl)-1H-pyrazol-4-yl]methanol (Preparation 37) | LCMS m/z = 309.1 [MH]$^+$ |
| 25 | 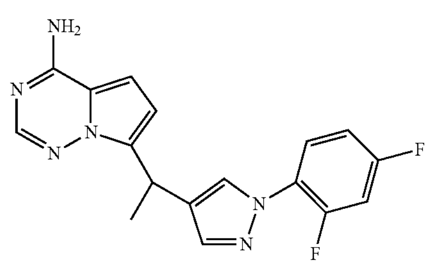 [SMILES: CC(c1cnn(-c2ccc(F)cc2F)c1)c1ccc2c(N)ncnn12] | 1-(4-aminopyrrolo[2,1-f][1,2,4]triazin-7-yl)-1-[1-(2,4-difluorophenyl)-1H-pyrazol-4-yl]ethanol (Preparation 39) | LCMS m/z = 341.1 [MH]$^+$ |

| Prep. No. | Structure | Starting Material | Starting Material, Yield, data |
|---|---|---|---|
| 26 | 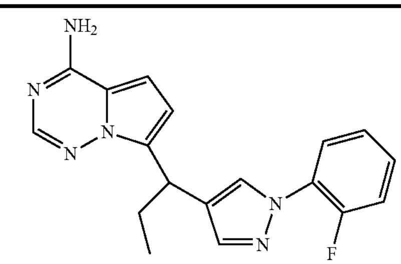 | 1-(4-aminopyrrolo[2,1-f][1,2,4]triazin-7-yl)-1-[1-(2-fluorophenyl)-1H-pyrazol-4-yl]propan-1-ol (Preparation 40) | LCMS m/z = 337.1 [MH]+ |
| 27 | 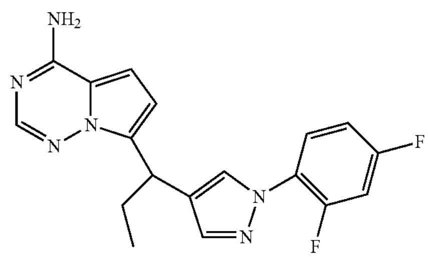 [SMILES: CCC(c1cnn(-c2ccc(F)cc2F)c1)c1ccc2c(N)ncnn12] | 1-(4-aminopyrrolo[2,1-f][1,2,4]triazin-7-yl)-1-[1-(2,4-difluorophenyl)-1H-pyrazol-4-yl]propan-1-ol (Preparation 41) | LCMS m/z = 355.1 [MH]+ |
| 28 | 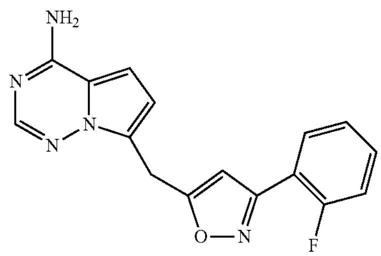 [SMILES: Nc1ncnn2c(Cc3cc(-c4ccccc4F)no3)ccc12] | (4-aminopyrrolo[2,1-f][1,2,4]triazin-7-yl)[3-(2-fluorophenyl)-1,2-oxazol-5-yl]methanol (Preparation 42) | LCMS m/z = 310.4 [MH]+ |
| 29 | 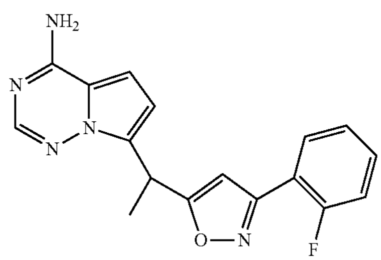 [SMILES: CC(c1cc(-c2ccccc2F)no1)c1ccc2c(N)ncnn12] | 1-(4-aminopyrrolo[2,1-f][1,2,4]triazin-7-yl)-1-[3-(2-fluorophenyl)-1,2-oxazol-5-yl]ethanol (Preparation 43) | LCMS m/z = 324.1 [MH]+ |

*a*EtOAc/pet. ether were used as the column eluents

Preparation 30: 7-{1-[1-(2-Fluorophenyl)-1H-pyrazol-4-yl]ethyl}pyrrolo[2,1-f][1,2,4]triazin-4-amine

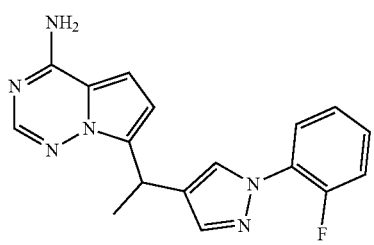 [SMILES: CC(c1cnn(-c2ccccc2F)c1)c1ccc2c(N)ncnn12]

A mixture of 1-(4-aminopyrrolo[2,1-f][1,2,4]triazin-7-yl)-1-[1-(2-fluorophenyl)-1H-pyrazol-4-yl]ethanol (Preparation 38, 6.5 g, 19.2 mmol) in Et$_3$SiH (15 mL) and TFA (45 mL) was stirred at rt for 14 hrs. The solvent was removed under reduced pressure, aq. NaHCO$_3$ solution (100 mL) added and the mixture extracted with EtOAc (50 mL×3). The combined organic extracts were washed with brine (50 mL), dried (Na$_2$SO$_4$), filtered and the filtrate concentrated under reduced pressure. The residue was purified by column chromatography on silica gel eluting with EtOAc:pet. ether (0:100 to 60:40) to afford the title compound, contaminated with 7-(1-(1-(2-fluorophenyl)-1H-pyrazol-4-yl)vinyl)pyrrolo[2,1-f][1,2,4]triazin-4-amine, as an oil. The oil was dissolved in MeOH (20 mL), Pd/C (500 mg) added and the mixture degased under N2, then purged with H$_2$. The reaction was stirred at rt for 2 hrs, then filtered through Celite®, washing through with MeOH. The combined filtrates were evaporated under reduced pressure to afford the title compound as an off-white solid (5 g, 83%). LCMS m/z=323.1 [MH]+

Preparation 31: 1-(4-Aminopyrrolo[2,1-f][1,2,4]triazin-7-yl)-1-[1-(2-fluorophenyl)-1H-1,2,3-triazol-4-yl]ethanol

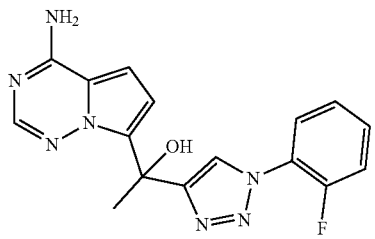 [SMILES: CC(O)(c1cn(-c2ccccc2F)nn1)c1ccc2c(N)ncnn12]

To a stirred solution of N'-(7-bromopyrrolo[2,1-f][1,2,4]triazin-4-yl)-N,N-dimethylimidoformamide (Preparation 50, 1 g, 3.73 mmol) in THF (30 mL) was added iPrMgCl (LiCl complex) (1.3 M in THF) (11.5 mL, 14.9 mmol) under N2 at −30° C. and the mixture stirred at rt for 4 hrs. The reaction was cooled in ice, an ice cooled solution of 1-(1-(2-fluorophenyl)-1H-1,2,3-triazol-4-yl)ethanone (918 mg, 4.5 mmol) in THF (20 mL) was added and the reaction stirred at rt for 2 hrs. The mixture was quenched using aq. NH$_4$Cl (10 mL) and the solvent was removed under reduced pressure. The residue was partitioned between H$_2$O (50 mL) and EtOAc (40 mL) the layers separated and the aqueous phase extracted with EtOAc (40 mL×2). The combined organic extracts were dried (Na$_2$SO$_4$), filtered and the filtrate concentrated in vacuo. The residue was purified by column chromatography on silica gel eluting with EtOAc:pet. ether (0:100 to 90:10) to afford the title compound as a yellow solid (400 mg, 31%). $^1$HNMR (400 MHz, DMSO-d$_6$): 2.05 (s, 3H), 6.09 (s, 1H), 6.64 (d, 1H), 6.85 (d, 1H), 7.40 (m, 1H), 7.50-7.70 (m, 5H), 7.78 (m, 1H), 8.31 (s, 1H). LCMS m/z=340.1 [MH]$^+$; RT [HPLC Method A]=1.224 min.

Preparations 32 to 44

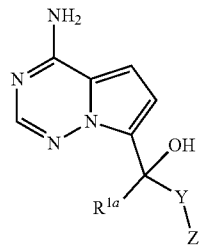

The following compounds were prepared from N'-(7-bromopyrrolo[2,1-f][1,2,4]triazin-4-yl)-N,N-dimethylimidoformamide (Preparation 50), and the appropriate ketone or aldehyde, following an analogous method to that described in Preparation 31.

| Prep. No. | R$^{1a}$C(OH)—Y—Z | Starting Material | Analytical Data |
|---|---|---|---|
| 32 | (structure: methyl, OH, triazole, 2,4-difluorophenyl) | 1-[1-(2,4-difluorophenyl)-1H-1,2,3-triazol-4-yl]ethanone | LCMS m/z = 358.1 [MH]$^+$; RT [HPLC Method A] = 1.408 min. |
| 33 | (structure: ethyl, OH, triazole, 2,4-difluorophenyl) | 1-(1-(2,4-difluorophenyl)-1H-1,2,3-triazol-4-yl)propan-1-one (Preparation 51) | LCMS m/z = 372.2 [MH]$^+$; RT [HPLC Method A] = 1.331 min. |
| 34 | (structure: ethyl, OH, triazole, 2,5-difluorophenyl) | 1-(1-(2,5-difluorophenyl)-1H-1,2,3-triazol-4-yl)propan-1-one (Preparation 52) | LCMS m/z = 372.2 [MH]$^+$ |
| 35 | (structure: ethyl, OH, triazole, 3,4-difluorophenyl) | 1-(1-(3,4-difluorophenyl)-1H-1,2,3-triazol-4-yl)propan-1-one (Preparation 53) | LCMS m/z = 372.2 [MH]$^+$ |
| 36 | (structure: ethyl, OH, pyrazole, isopropyl) | 1-[1-(propan-2-yl)-1H-pyrazol-4-yl]propan-1-one | $^1$HNMR (400 MHz, DMSO-d$_6$): 0.71 (t, 3H), 1.33 (s, 3H), 1.34 (d, 6H), 2.11 (m, 1H), 2.50 (m, 1H), 4.39 (m, 1H), 5.64 (s, 1H), 6.56 (d, 1H), 6.82 (d, 1H), 7.24 (s, 1H), 7.50 (s, 1H), 7.60-7.70 (br s, 2H), 7.77 (s, 1H). LCMS |

| Prep. No. | R$^{1a}$C(OH)—Y—Z | Starting Material | Analytical Data |
|---|---|---|---|
| | | | m/z = 301.1 [MH]$^+$ |
| 37 | (pyrazole with CH(OH), N-2-fluorophenyl) | 1-(2-fluorophenyl)-1H-pyrazole-4-carbaldehyde | LCMS m/z = 325.1 [MH]$^+$ |
| 38 | (pyrazole with C(CH$_3$)(OH), N-2-fluorophenyl) | 1-[1-(2-fluorophenyl)-1H-pyrazol-4-yl]ethanone | LCMS m/z = 339.1 [MH]$^+$ |
| 39 | (pyrazole with C(CH$_3$)(OH), N-2,4-difluorophenyl) | 1-[1-(2,4-difluorophenyl)-1H-pyrazol-4-yl]ethanone | LCMS m/z = 357.1 [MH]$^+$ |
| 40 | (pyrazole with C(Et)(OH), N-2-fluorophenyl) | 1-[1-(2-fluorophenyl)-1H-pyrazol-4-yl]propan-1-one (Preparation 54) | LCMS m/z = 353.1 [MH]$^+$ |
| 41 | (pyrazole with C(Et)(OH), N-2,4-difluorophenyl) | 1-[1-(2,4-difluorophenyl)-1H-pyrazol-4-yl]propan-1-one (Preparation 55) | LCMS m/z = 371.2 [MH]$^+$ |
| 42 | (isoxazole with CH$_2$, 3-(2-fluorophenyl)) | 1-[3-(2-fluorophenyl)isoxazol-5-yl]ethanone | LCMS m/z = 326.1 [MH]$^+$ |
| 43 | (isoxazole with CH(CH$_3$), 3-(2-fluorophenyl)) | 1-[3-(2-fluorophenyl)-1,2-oxazol-5-yl]ethan-1-one | LCMS m/z = 340.0 [MH]$^+$ |

Preparation 44: tert-Butyl (7-{1-[1-(2-fluorophenyl)-1H-1,2,3-triazol-4-yl]-1-hydroxypropyl}pyrrolo[2,1-f][1,2,4]triazin-4-yl)carbamate

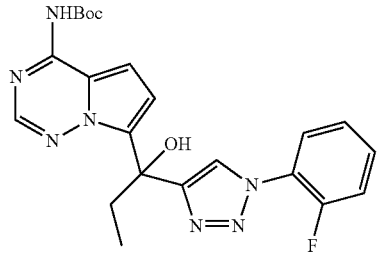 [SMILES: CCC(O)(c1cn(-c2ccccc2F)nn1)c1ccc2c(NC(=O)OC(C)(C)C)ncnn12]

Ethylmagnesium bromide (8.84 mmol, 8.84 mL) was added to a solution of tert-butyl (7-{[1-(2-fluorophenyl)-1H-1,2,3-triazol-4-yl]carbonyl}pyrrolo[2,1-f][1,2,4]triazin-4-yl)carbamate (Preparation 46, 1.5 g, 3.53 mmol) in THF (30 mL) at 0° C., and on complete addition, the reaction was stirred at 0° C. for 30 mins. NH$_4$Cl solution was slowly added and the mixture extracted with EtOAc (100 mL×2). The combined organic extracts were concentrated in vacuo to afford the title compound which was used without further purification (1.7 g, quant.). LCMS m/z=454.1 [MH]$^+$; RT [HPLC Method A]=1.712 min.

Preparation 45: 7-{[1-(2-Fluorophenyl)-1H-1,2,3-triazol-4-yl]methyl}pyrrolo[2,1-f][1,2,4]triazin-4-amine

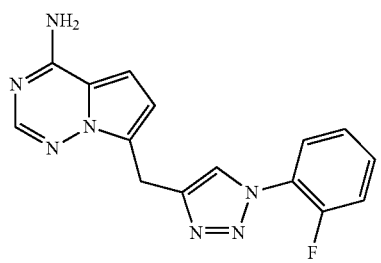 [SMILES: Nc1ncnn2c(Cc3cn(-c4ccccc4F)nn3)ccc12]

To an ice-cooled solution of tert-butyl (7-{[1-(2-fluorophenyl)-1H-1,2,3-triazol-4-yl]carbonyl}pyrrolo[2,1-f][1,2,4]triazin-4-yl)carbamate (Preparation 46, 5.01 g, 11.79 mmol) in DCM (40 mL) was added Et$_3$SiH (10 mL) and TFA (10 mL) and the reaction stirred at rt for 18 hrs. The mixture was concentrated in vacuo and the residue suspended in EtOAc (100 mL), washed with saturated NaHCO$_3$ soln. and brine (2×100 mL), dried (Na$_2$SO$_4$) and concentrated in vacuo. The crude product was purified by column chromatography on silica gel eluting with MeOH:DCM (5:95 to 9:91) to afford the title compound as a yellow solid (1.2 g, 25%). $^1$HNMR (400 MHz, MeOD-d$_4$): 4.55 (s, 2H), 6.81 (m, 1H), 7.38-7.44 (m, 3H), 7.60 (m, 1H), 7.85 (m, 1H), 8.04 (s, 1H), 8.31 (s, 1H). LCMS m/z=310.1 [MH]$^+$

Preparation 46: tert-Butyl (7-{[1-(2-fluorophenyl)-1H-1,2,3-triazol-4-yl]carbonyl}pyrrolo[2,1-f][1,2,4]triazin-4-yl)carbamate

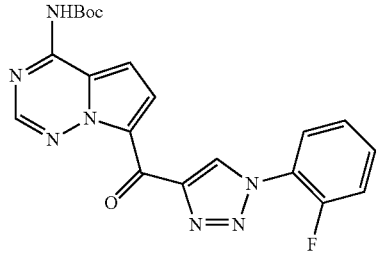 [SMILES: CC(C)(C)OC(=O)Nc1ncnn2c(C(=O)c3cn(-c4ccccc4F)nn3)ccc12]

MnO$_2$ (4.09 g, 47 mmol) was added to a solution of tert-butyl (7-{[1-(2-fluorophenyl)-1H-1,2,3-triazol-4-yl](hydroxyl)methyl}pyrrolo[2,1-f][1,2,4]triazin-4-yl)carbamate (Preparation 47, 4.0 g, 9.4 mmol) in DCM (50 mL) and the mixture heated under reflux for 32 hrs. The cooled mixture was filtered, the filtrate washed with DCM (100 mL×3) and concentrated in vacuo. The crude product was purified by column chromatography on silica gel eluting with pet. ether:EtOAc (50:50) to afford the title compound as a yellow solid (1.5 g, 37%). LCMS m/z=426.1 [MH]$^+$; RT [HPLC method A]=1.684 min.

Preparation 47: tert-Butyl (7-{[1-(2-fluorophenyl)-1H-1,2,3-triazol-4-yl](hydroxyl) methyl}pyrrolo[2,1-f][1,2,4]triazin-4-yl)carbamate

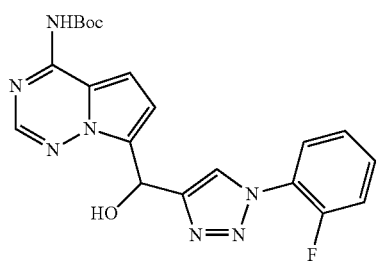 [SMILES: CC(C)(C)OC(=O)Nc1ncnn2c(C(O)c3cn(-c4ccccc4F)nn3)ccc12]

1-Azido-2-fluorobenzene (2.28 g, 16.67 mmol), CuI (1.5 g, 8.33 mmol), and DIPEA (3.22 g, 24.99 mmol) were added to a solution of tert-butyl [7-(1-hydroxyprop-2-yn-1-yl)pyrrolo[2,1-f][1,2,4]triazin-4-yl]carbamate (Preparation 48, 2.4 g, 8.33 mmol) in toluene (30 mL) and t-BuOH (15 mL) and the reaction stirred at rt under N2 for 16 hrs. The mixture was concentrated in vacuo and the crude product purified by column chromatography on silica gel eluting with DCM:MeOH (97:3) to afford the title compound as a yellow solid (2.6 g, 73.4%). LCMS m/z=426.1 [MH]$^+$; RT [HPLC Method A]=1.604 min.

Preparation 48: tert-Butyl [7-(1-hydroxyprop-2-yn-1-yl)pyrrolo[2,1-f][1,2,4]triazin-4-yl]carbamate

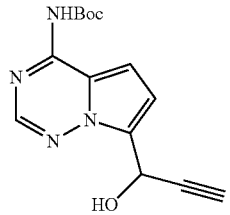 [SMILES: C#CC(O)c1ccc2c(NC(=O)OC(C)(C)C)ncnn12]

Ethynylmagnesium bromide (42 mL, 0.5M in THF, 21 mmol) was slowly added to an ice-cooled solution of tert-butyl (7-formylpyrrolo[2,1-f][1,2,4]triazin-4-yl)carbamate (Preparation 49, 2.5 g, 9.54 mmol) in THF (40 mL) and the reaction stirred at rt for 2 hrs. Sat. aq. NH$_4$Cl was slowly added to the reaction, and the mixture extracted with EtOAc (50 mL×2), the combined organic extracts dried (Na$_2$SO$_4$) and concentrated in vacuo. The crude product was purified by column chromatography on silica gel eluting with pet.ether:EtOAc (50:50) to afford the title compound as a yellow solid (2.4 g, 87%). LCMS m/z=233.1 [M-(C$_3$HO)]$^+$ Preparation 49: tert-Butyl (7-formylpyrrolo[2,1-f][1,2,4]triazin-4-yl)carbamate

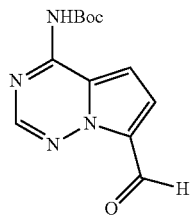 [SMILES: CC(C)(C)OC(=O)Nc1ncnn2c(C=O)ccc12]

(Boc)$_2$O (12 g, 56 mmol) followed by DMAP (4.5 g, 37 mmol) were slowly added to a solution of 4-aminopyrrolo[2,1-f][1,2,4]triazine-7-carbaldehyde (WO2007064931, 6.0 g, 37 mmol) in DCM (100 mL) and the reaction stirred for 30 min. The reaction was diluted with water and the mixture extracted with DCM (100 mL×2), the combined organic extracts, dried (Na$_2$SO$_4$) and concentrated in vacuo. The crude product was purified by column chromatography on silica gel eluting with pet. ether:EtOAc (77:23) to afford the title compound as a yellow solid (2.5 g, 25%). LCMS m/z=285.1 [MNa]$^+$ Preparation 50: N'-(7-bromopyrrolo[2,1-f][1,2,4]triazin-4-yl)-N,N-dimethylimidoformamide

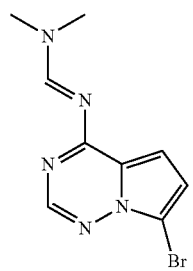

A mixture of 7-bromopyrrolo[2,1-f][1,2,4]triazin-4-amine (40 g, 0.19 mmol) and N,N-dimethylformamide dimethyl acetal (2 L) was heated to 90° C. for 2 hrs. The cooled mixture was concentrated in vacuo. The residue was purified by column chromatography on silica gel eluting with DCM:EtOAc (91:9) to afford the title compound (100 g, 69%). $^1$HNMR (400 MHz, DMSO-d$_6$): 3.19 (s, 3H), 3.25 (s, 3H), 6.90 (m, 2H), 8.16 (s, 1H), 8.95 (s, 1H). LCMS m/z=268.0 [MH]$^+$; RT [HPLC Method A]=0.934 min.

Preparation 51: 1-[-(2,4-Difluorophenyl)-1H-1,2,3-triazol-4-yl]propan-1-one

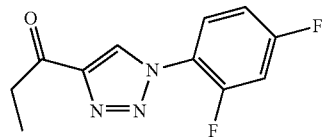 [SMILES: CCC(=O)c1cn(-c2ccc(F)cc2F)nn1]

To a solution of pent-1-yn-3-one (1.3 g, 15.84 mmol) in MeOH/H$_2$O (30 mL/5 mL) was added 1-azido-2,4-difluorobenzene (2.95 g, 19 mmol), sodium L-ascorbate (1.57 g, 7.92 mmol) and CuSO$_4$ (1.27 g, 7.92 mmol) and the reaction stirred at rt for 12 hrs. The solvent was removed under reduced pressure and the residue purified by column chromatography on silica gel eluting with EtOAc:pet. ether (0:100 to 20:80) to afford the title compound as an off-white solid (2.5 g, 67%). $^1$HNMR (400 MHz, CDCl$_3$): 1.27 (t, 3H), 3.22 (q, 2H), 7.12 (m, 2H), 7.94 (m, 1H), 8.53 (s, 1H). LCMS m/z=238.1 [MH]$^+$; RT [HPLC Method A]=1.605 min.

Preparation 52: 1[-(2,5-Difluorophenyl)-1H-1,2,3-triazol-4-yl]propan-1-one

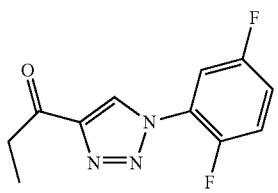 [SMILES: CCC(=O)c1cn(-c2cc(F)ccc2F)nn1]

The title compound was obtained as an off-white solid (1.75 g, 61%) from pent-1-yn-3-one and 2-azido-1,4-difluorobenzene, following the procedure described in Preparation 51. $^1$HNMR (400 MHz, CDCl$_3$): 1.25 (t, 3H), 3.21 (q, 2H), 7.20 (m, 1H), 723-7.33 (m, 1H), 7.79 (m, 1H), 8.64 (s, 1H). LCMS m/z=238.1 [MH]$^+$ Preparation 53: 1-[-(3,4-Difluorophenyl)-1H-1,2,3-triazol-4-yl]propan-1-one

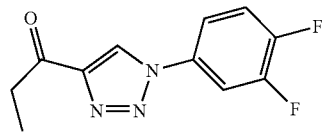 [SMILES: CCC(=O)c1cn(-c2ccc(F)c(F)c2)nn1]

The title compound was obtained as an off-white solid (1.70 g, 59%) from pent-1-yn-3-one and 4-azido-1,2-difluorobenzene, following the procedure described in Preparation 51. ¹HNMR (400 MHz, CDCl₃): 1.27 (t, 3H), 3.22 (q, 2H), 7.26-7.39 (m, 1H), 7.51 (m, 1H), 7.70 (m, 1H), 8.45 (s, 1H). LCMS m/z=238.1 [MH]⁺

Preparation 54: 1-[1-(2-Fluorophenyl)-1H-pyrazol-4-yl]propan-1-one

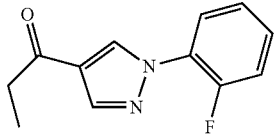 [SMILES: CCC(=O)c1cnn(-c2ccccc2F)c1]

To a mixture of 1-[5-amino-1-(2-fluorophenyl)-1H-pyrazol-4-yl]propan-1-one (Preparation 56, 5 g, 21.44 mmol) in THF (150 mL) was added drop wise tert-butyl nitrite (4.1 g, 39.8 mmol) at rt and the reaction stirred at 65° C. for 4 hrs. The solvent was evaporated under reduced pressure and purified by column chromatography on silica gel eluting with pet. ether:EtOAc (10:1 to 1:1) to afford the title compound as a yellow oil (2 g, 42.75%). ¹HNMR (400 MHz, MeOD-d₄): 1.08 (t, 3H), 2.82 (q, 2H), 7.24-7.31 (m, 2H), 7.36-7.40 (m, 1H), 7.71 (m, 1H), 8.09 (s, 1H), 8.57 (d, 1H). LCMS m/z=219.1 [MH]⁺

Preparation 55: 1-[1-(2,4-Difluorophenyl)-1H-pyrazol-4-yl]propan-1-one

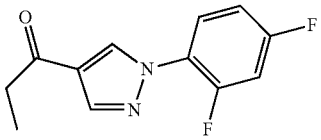 [SMILES: CCC(=O)c1cnn(-c2ccc(F)cc2F)c1]

The title compound was obtained (2 g, 42%) from 1-[5-amino-1-(2,4-difluorophenyl)-1H-pyrazol-4-yl]propan-1-one (Preparation 57), following the procedure described in Preparation 54. ¹HNMR (400 MHz, MeOD-d₄): 1.19 (t, 3H), 2.92 (q, 2H), 7.17 (m, 1H), 7.27 (m, 1H), 7.84 (m, 1H), 8.22 (s, 1H), 8.65 (d, 1H). LCMS m/z=237.1 [MH]⁺

Preparation 56: 1-[5-Amino-1-(2-fluorophenyl)-1H-pyrazol-4-yl]propan-1-one

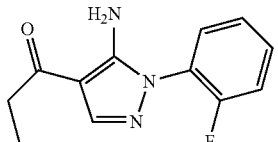

A degassed mixture of (E)-2-(ethoxymethylene)-3-oxopentanenitrile (6 g, 39.17 mmol), Et₃N (11.89 g, 117.5 mmol) and (2-fluorophenyl)hydrazine hydrochloride (9.55 g, 58.75 mmol) in EtOH (200 mL) was stirred under reflux for 2 hrs under an atmosphere of N2. The cooled reaction was concentrated in vacuo and the residue purified by column chromatography on silica gel eluting with pet. ether:EtOAc (10:1 to 1:1) to afford the title compound as a yellow oil (5 g, 54.74%). LCMS m/z=234.1 [MH]⁺

Preparation 57: 1-[5-Amino-1-(2,4-difluorophenyl)-1H-pyrazol-4-yl]propan-1-one

The title compound was obtained as a yellow oil (5 g, 51%) from (E)-2-(ethoxymethylene)-3-oxopentanenitrile and (2,4-difluorophenyl)hydrazine hydrochloride following the procedure described in Preparation 56. LCMS m/z=252.1 [MH]⁺

Preparation 58: 1-{1-[1-(2-Fluorophenyl)-1H-pyrazol-4-yl]propyl}-3-iodo-1H-pyrazolo[3,4-d]pyrimidin-4-amine

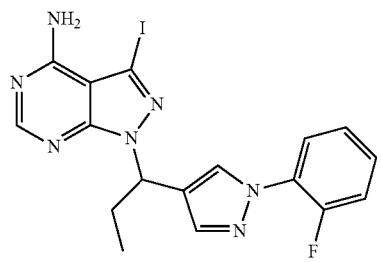 [SMILES: CCC(c1cnn(-c2ccccc2F)c1)n1nc(I)c2c(N)ncnc21]

To a solution of 3-iodo-1H-pyrazolo[3,4-d]pyrimidin-4-amine (0.9 g, 3.78 mmol) in DMF (30 mL) was added 4-(1-chloropropyl)-1-(2-fluorophenyl)-1H-pyrazole (Preparation 61, 1.08 g, 4.54 mmol) and Cs₂CO₃ (6.16 g, 18.9 mmol) and the reaction stirred at 90° C. under N2 for 18 hrs. The cooled mixture was diluted with water then extracted with EtOAc, the organic layer washed with brine, dried and evaporated. The crude product was purified by column chromatography on silica gel eluting with DCM:MeOH (95:5) to give the title compound (0.5 g, 28%). ¹HNMR (400 MHz, DMSO-d₆): 0.75 (t, 3H), 2.18-2.29 (m, 1H), 2.33-2.39 (m, 1H), 5.84 (m, 1H), 7.32 (m, 1H), 7.40-7.48 (m, 2H), 7.74 (m, 2H), 8.19 (s, 1H), 8.26 (s, 1H). LCMS m/z=463.9 [MH]⁺

Preparation 59: 1-{[1-(2-Fluorophenyl)-1H-1,2,3-triazol-4-yl]propyl}-3-iodo-1H-pyrazolo[3,4-d]pyrimidin-4-amine

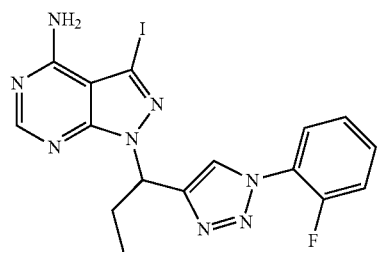 [SMILES: CCC(c1cn(-c2ccccc2F)nn1)n1nc(I)c2c(N)ncnc21]

To a stirred solution of 3-iodo-1-(pent-1-yn-3-yl)-1H-pyrazolo[3,4-d]pyrimidin-4-amine (Preparation 60, 7 g, 21.40 mmol) in toluene (25 mL) was added 1-azido-2-fluorobenzene (5.87 g, 42.80 mmol), DIPEA (13.8 g, 107.0 mmol) and t-BuOH (100 mL). CuI (2.45 g, 12.84 mmol) was added and the reaction stirred at rt under N2 for 16 hrs. The mixture was concentrated under reduced pressure and purified by column chromatography on silica gel eluting with DCM:MeOH (97:3) to afford the title compound (5.4 g, 54%). $^1$HNMR (400 MHz, DMSO-$d_6$): 0.79 (t, 3H), 2.46 (m, 2H), 6.03 (m, 1H), 7.41 (m, 1H), 7.45-7.60 (m, 2H), 7.83 (m, 1H), 8.28 (s, 1H), 8.61 (s, 1H). LCMS m/z=464.9 [MH]$^+$ Preparation 60: 3-Iodo-1-(pent-1-yn-3-yl)-1H-pyrazolo[3,4-d]pyrimidin-4-amine

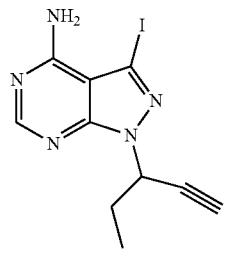 [SMILES: C#CC(CC)n1nc(I)c2c(N)ncnc21]

3-Bromopent-1-yne (8.6 g, 58.5 mmol) was added to a solution of 3-iodo-1H-pyrazolo[3,4-d]pyrimidin-4-amine (10.2 g, 39 mmol) and $Cs_2CO_3$ (38 g, 117 mmol) in DMF (200 mL) and the reaction stirred at rt for 16 hrs. The mixture was concentrated in vacuo, the residue diluted with water and extracted with EtOAc (300 mL×3). The combined organic phases were washed with brine (300 ml×2), dried ($Na_2SO_4$) and concentrated to afford the title compound as a brown solid (7 g, 55%). LCMS m/z=327.9 [MH]$^+$ Preparation 61: 4-(1-Chloropropyl)-1-(2-fluorophenyl)-1H-pyrazole

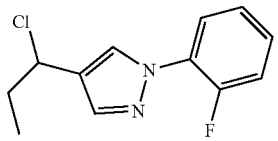 [SMILES: CCC(Cl)c1cnn(-c2ccccc2F)c1]

To a solution of 1-(1-(2-fluorophenyl)-1H-pyrazol-4-yl)propan-1-ol (Preparation 62, 1 g, 4.54 mmol) in DCM (30 mL) was added $SOCl_2$ (5 mL) drop wise and the reaction stirred at rt for 2 hrs. The mixture was evaporated under reduced pressure to afford the title compound (1.08 g, quant.).

Preparation 62: 1-[1-(2-Fluorophenyl)-1H-pyrazol-4-yl]propan-1-ol

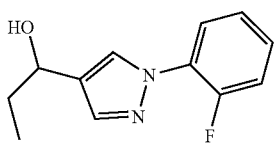 [SMILES: CCC(O)c1cnn(-c2ccccc2F)c1]

To a solution of 1-(2-fluorophenyl)-1H-pyrazole-4-carbaldehyde (3 g, 15.8 mmol) in THF (50 mL) was added EtMgBr (31.6 mL, 31.6 mmol) drop wise at 0° C. and the reaction stirred at rt for 2 hrs. Water was added to quench the reaction and the mixture extracted with EtOAc. The organic layer was collected, washed with brine, dried and evaporated. The crude product was purified by column chromatography on silica gel eluting with DCM:MeOH (95:5) to afford the title compound (3 g, 86%). $^1$HNMR (400 MHz, $CDCl_3$): 1.00 (t, 3H), 1.74 (br s, 1H), 1.88 (m, 2H), 4.71 (t, 1H), 7.19-7.27 (m, 3H), 7.71 (s, 1H), 7.88 (m, 1H), 7.96 (d, 1H). LCMS m/z=221.2 [MH]$^+$ Preparation 63: 5-(4-Chlorophenyl)-7-{[1-(2-fluorophenyl)-1H-1,2,3-triazol-4-yl]methyl}imidazo[5,1-f][1,2,4]triazin-4-ol

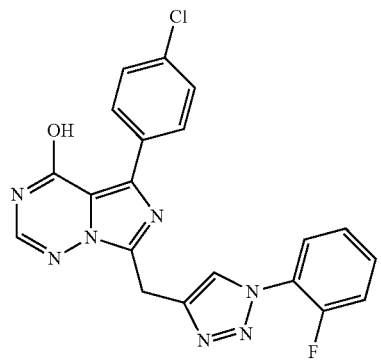 [SMILES: Oc1ncnn2c(Cc3cn(-c4ccccc4F)nn3)nc(-c3ccc(Cl)cc3)c12]

A mixture of ethyl 1-amino-4-(4-chlorophenyl)-2-{[1-(2-fluorophenyl)-1H-1,2,3-triazol-4-yl]methyl}-1H-imidazole-5-carboxylate (Preparation 64, 72 mg, 0.16 mmol), formamide (1.63 mL, 0.6M) and formamidine acetate (42.5 mg, 0.408 mmol) was degassed for 2 mins, then heated at 130° C. under microwave irradiation for 2 hr. Additional formamidine acetate (50 mg, 0.48 mmol) was added and the reaction heated to 150° C. for a further 2 hr. The cooled mixture was filtered and dried to afford the title compound as a tan solid (42 mg, 62%). $^1$HNMR (400 MHz, DMSO-$d_6$): 4.53 (s, 2H), 7.40-7.63 (m, 5H), 7.80 (m, 1H), 7.98 (s, 1H), 8.38 (d, 2H), 8.50 (s, 1H), 11.95 (br s, 1H). LCMS m/z=422.2 [MH]$^+$ Preparation 64: Ethyl 1-amino-4-(4-chlorophenyl)-2-{[1-(2-fluorophenyl)-1H-1,2,3-triazol-4-yl]methyl}-1H-imidazole-5-carboxylate

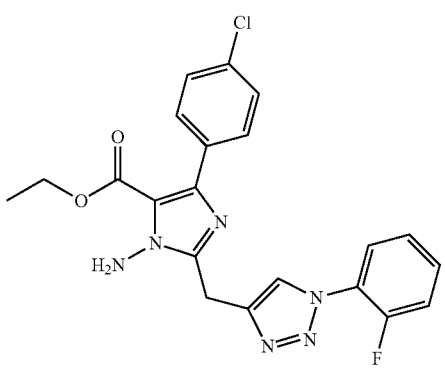 [SMILES: CCOC(=O)c1c(-c2ccc(Cl)cc2)nc(Cc2cn(-c3ccccc3F)nn2)n1N]

LiHMDS (1.0M in THF, 0.181 mL, 0.181 mmol) was added drop wise to an ice-cooled solution of ethyl 4-(4-chlorophenyl)-2-{[1-(2-fluorophenyl)-1H-1,2,3-triazol-4-yl]methyl}-1H-imidazole-5-carboxylate (Preparation 65, 70 mg, 0.16 mmol) in DMF (1.1 mL). o-(Diphenylphosphinyl)-hydroxylamine (53.7 mg, 0.23 mmol) was added in two portions while maintaining the internal temperature at 0° C. The resulting white suspension was diluted with DMF (5 mL) and the solution stirred at rt for 18 hrs. The reaction was diluted with water and extracted with DCM (4×50 mL). The combined organic layers were dried (Na$_2$SO$_4$) and concentrated in vacuo. The residue was purified by column chromatography on silica gel eluting with EtOAc:heptane (0:100 to 100:0) to afford the title compound (35 mg, 50%). $^1$HNMR (400 MHz, CDCl$_3$): 1.26 (t, 3H), 4.32 (q, 2H), 4.50 (s, 2H), 6.18 (br s, 2H), 7.25-8.23 (m, 9H). LCMS m/z=441.2 [MH]$^+$ Preparation 65: Ethyl 4-(4-chlorophenyl)-2-{[1-(2-fluorophenyl)-1H-1,2,3-triazol-4-yl]methyl}-1H-imidazole-5-carboxylate

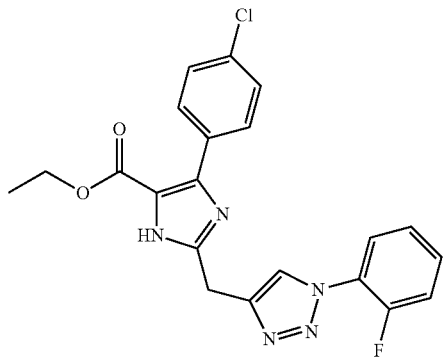 [SMILES: CCOC(=O)c1[nH]c(Cc2cn(-c3ccccc3F)nn2)nc1-c1ccc(Cl)cc1]

A mixture of ethyl 3-(4-chlorophenyl)-2-{2-[1-(2-fluorophenyl)-1H-1,2,3-triazol-4-yl]acetamido}-3-oxopropanoate (Preparation 66, 281 mg, 0.632 mmol) and ammonium acetate (300 mg, 3.89 mmol) in acetic acid (3.16 mL) was heated at 150° C. for 2 hrs under microwave irradiation. The cooled mixture was concentrated under reduced pressure and the residue purified by column chromatography on silica gel eluting with EtOAc:heptanes (0:100 to 100:0) to afford the title compound (72 mg, 27%). LCMS m/z=426.3 [MH]$^+$ Preparation 66: Ethyl 3-(4-chlorophenyl)-2-{2-[1-(2-fluorophenyl)-1H-1,2,3-triazol-4-yl]acetamido}-3-oxopropanoate

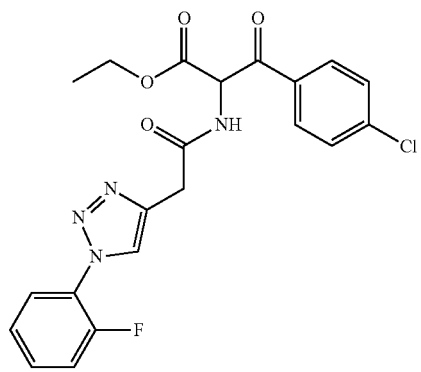 [SMILES: CCOC(=O)C(NC(=O)Cc1cn(-c2ccccc2F)nn1)C(=O)c1ccc(Cl)cc1]

A mixture of ethyl 2-amino-3-(4-chlorophenyl)-3-oxopropanoate (Preparation 67, 246 mg, 1.02 mmol), 2-[1-(2-fluorophenyl)-1H-1,2,3-triazol-4-yl]acetic acid (150 mg 0.678 mmol), NMM (0.261 mL, 2.37 mmol), HATU (387 mg, 1.02 mmol) in DMF (4.52 mL) was stirred at rt for 18 hrs. The mixture was diluted with NH$_4$Cl, extracted with 3×100 mL EtOAc and the combined organic solutions washed with sat. LiCl solution and dried (Na$_2$SO$_4$) and filtered. The filtrate was evaporated under reduced pressure, the residue purified by column chromatography on silica gel eluting with MeOH:DCM (0:100 to 20:80) to afford the title compound (311 mg, x %). LCMS m/z=445.3 [MH]$^+$ Preparation 67: Ethyl 2-amino-3-(4-chlorophenyl)-3-oxopropanoate

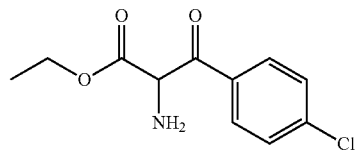 [SMILES: CCOC(=O)C(N)C(=O)c1ccc(Cl)cc1]

A solution of ethyl 2-(diphenylmethyleneamino)acetate (5 g, 18.7 mmol) in THF (35 mL) was added via cannula over 30 mins to a solution of potassium t-butoxide (15 mL in THF) at −78° C. and the solution stirred for 35 mins. 4-Chlorobenzoyl chloride (2.57 mL, 20 mmol) in THF (10 mL) was added drop wise, the reaction stirred at −78° C. for 25 mins then allowed to warm to −50° C., and stirred for 40 mins. The reaction was quenched with a solution of conc. HCl (2.15 mL, 25.2 mol) in 1 mL water and the mixture allowed to warm to rt. The reaction slurry was filtered to remove inorganic salts, the filtrate evaporated and azeotroped to remove residual water. The crude product was purified by column chromatography on silica gel eluting with MeOH:DCM (0:100 to 10:90) to afford the title compound as a white solid (1.01 g, 22%). $^1$HNMR (400 MHz, DMSO-d$_6$): 1.07 (t, 3H), 4.15 (q, 2H), 6.28 (s, 1H), 7.72 9d, 2H), 8.20 (d, 2H), 9.05 (br s, 2H). LCMS m/z=242.3 [MH]$^+$

EXAMPLES

Examples 1 to 19

The following compounds were obtained by chiral separation of the corresponding racemic starting material, using the HPLC methods previously described.

| Ex. No. | Structure | Separation Method Starting Material | Analytical Data |
|---|---|---|---|
| 1 | 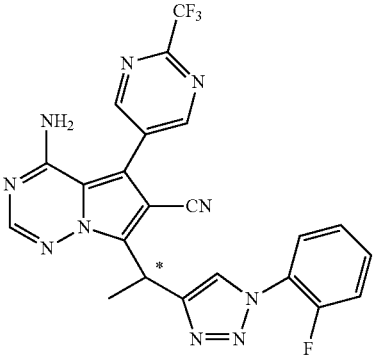<br>Enantiomer 1 | HPLC Method C20B; 4-amino-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile (Example 23) | $^1$HNMR (400 MHz, DMSO-$d_6$): 1.88 (d, 3H), 5.20 (q, 1H), 6.95-7.10 (br s, 2H), 7.43 (m, 1H), 7.54-7.62 (m, 2H), 7.78 (m, 1H), 8.18 (s, 1H), 8.61 (s, 1H), 9.16 (s, 2H). LCMS m/z = 495.1 [MH]$^+$; RT [HPLC Method C4] = 3.824 min. |
| 2 | 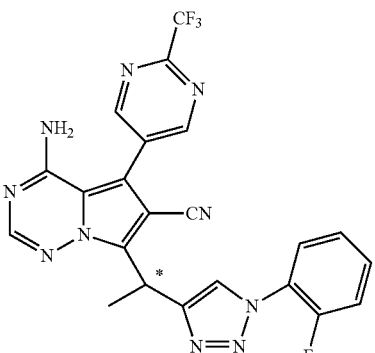<br>Enantiomer 2 | HPLC Method C20B; 4-amino-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile (Example 23) | $^1$HNMR (400 MHz, DMSO-$d_6$): 1.88 (d, 3H), 5.20 (q, 1H), 6.95-7.10 (br s, 2H), 7.43 (m, 1H), 7.56-7.62 (m, 2H), 7.77 (m, 1H), 8.18 (s, 1H), 8.61 (s, 1H), 9.16 (s, 2H). LCMS m/z = 495.1 [MH]$^+$; RT [HPLC Method C4] = 5.435 min. |
| 3 | 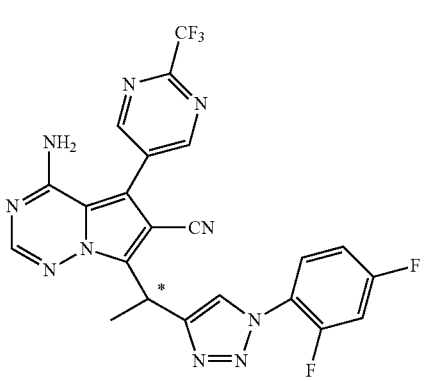<br>Enantiomer 1 | HPLC Method C22B; 4-amino-7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile (Example 24) | $^1$HNMR (400 MHz, DMSO-$d_6$): 1.87 (d, 3H), 5.20 (q, 1H), 6.95-7.12 (br s, 2H), 7.32 (m, 1H), 7.65 (m, 1H), 7.71 (m, 1H), 8.18 (s, 1H), 8.60 (s, 1H), 9.16 (s, 2H). LCMS m/z = 513.2 [MH]$^+$; RT [HPLC Method C2] = 2.268 min. |
| 4 | 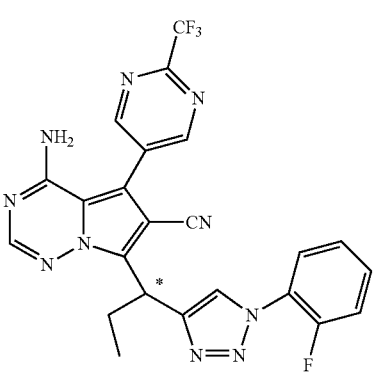<br>Enantiomer 1 | HPLC Method C20B; 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 25) | $^1$HNMR (400 MHz, DMSO-$d_6$): 0.97 (t, 3H), 2.36-2.43 (m, 2H), 5.02 (t, 1H), 7.43 (m, 1H), 7.54-7.64 (m, 2H), 7.78 (m, 1H), 8.17 (s, 1H), 8.60 (d, 1H), 9.18 (s, 2H). LCMS m/z = 509.1 [MH]$^+$; RT [HPLC Method C1] = 3.464 min. |

| Ex. No. | Structure | Separation Method Starting Material | Analytical Data |
|---|---|---|---|
| 5 | 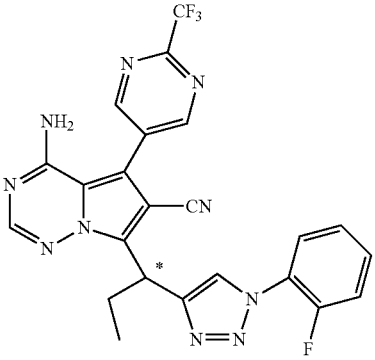<br>Enantiomer 2 | HPLC Method C20B; 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 25) | $^1$HNMR (400 MHz, DMSO-$d_6$): 0.99 (t, 3H), 2.38-2.44 (m, 2H), 5.03 (t, 1H), 7.43 (m, 1H), 7.54-7.61 (m, 2H), 7.79 (m, 1H), 8.17 (s, 1H), 8.60 (d, 1H), 9.19 (s, 2H).; LCMS m/z = 509.1 [MH]$^+$; RT [HPLC Method C1] = 4.109 min. |
| 6 | 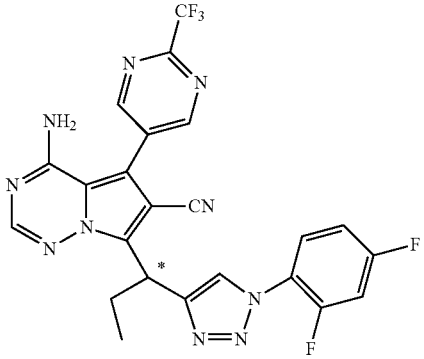<br>Enantiomer 1 | HPLC Method E4; 4-amino-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 26) | $^1$HNMR (400 MHz, DMSO-$d_6$): 0.98 (t, 3H), 2.39 (m, 2H), 5.02 (t, 1H), 7.35 (m, 1H), 7.65 (m, 1H), 7.85 (m, 1H), 8.16 (s, 1H), 8.59 (s, 1H), 9.18 (s, 2H). LCMS m/z = 527.1 [MH]$^+$; RT [HPLC Method C1] = 3.024 min. |
| 7 | 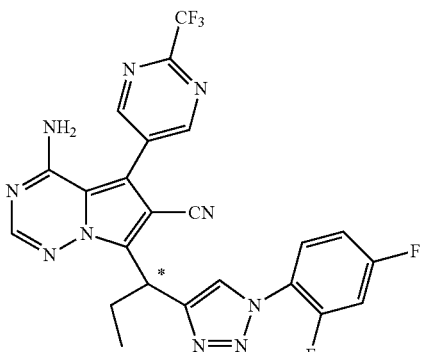<br>Enantiomer 2 | HPLC Method E4; 4-amino-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 26) | $^1$HNMR (400 MHz, DMSO-$d_6$): 0.98 (t, 3H), 2.33-2.42 (m, 2H), 5.01 (t, 1H), 7.32-7.37 (m, 1H), 7.65 (m, 1H), 7.95 (m, 1H), 8.16 (s, 1H), 8.58 (d, 1H), 9.18 (s, 2H). LCMS m/z = 527.1 [MH]$^+$; RT [HPLC Method C1] = 3.480 min. |

-continued

| Ex. No. | Structure | Separation Method Starting Material | Analytical Data |
|---|---|---|---|
| 8 | Enantiomer 2 | HPLC Method C23B; 4-amino-7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 28) | $^1$HNMR (400 MHz, DMSO-$d_6$): 0.98 (t, 3H), 2.36-2.42 (m, 2H), 5.02 (t, 1H), 7.46-7.52 (m, 1H), 7.65 (m, 1H), 7.77 (m, 1H), 8.16 (s, 1H), 8.63 (d, 1H), 9.18 (s, 2H). LCMS m/z = 527.2 [MH]$^+$; RT [HPLC Method C2] = 2.543 min. |
| 9 | Enantiomer 2 | HPLC Method C23B; 4-amino-7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile (Example 27) | $^1$HNMR (400 MHz, DMSO-$d_6$): 0.98 (t, 3H), 2.33-2.42 (m, 2H), 4.99 (t, 1H), 7.67-7.74 (m, 1H), 7.85 (m, 1H), 8.09 (m, 1H), 8.4 (s, 1H), 8.84 (s, 1H), 9.18 (s, 2H). LCMS m/z = 527.1 [MH]$^+$; RT [HPLC Method C2] = 3.352 min. |
| 10 | Enantiomer 1 | HPLC Method C28; 4-amino-7-{1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile (Example 29) | $^1$HNMR (400 MHz, DMSO-$d_6$): 0.89 (t, 3H), 1.36 (d, 6H), 2.16-2.28 (m, 2H), 4.43 (m, 1H), 4.70 (m, 1H), 7.37 (s, 1H), 7.69 (s, 1H), 8.15 (s, 1H), 9.17 (s, 2H). LCMS m/z = 456.2 [MH]$^+$; RT [HPLC Method C12] = 6.292 min. |
| 11 | Enantiomer 2 | HPLC Method C28; 4-amino-7-{1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile (Example 29) | $^1$HNMR (400 MHz, DMSO-$d_6$): 0.89 (t, 3H), 1.36 (d, 6H), 2.21-2.28 (m, 2H), 4.43 (m, 1H), 4.70 (m, 1H), 7.37 (s, 1H), 7.69 (s, 1H), 8.15 (s, 1H), 9.17 (s, 2H). LCMS m/z = 456.2 [MH]$^+$; RT [HPLC Method C12] = 9.60 min. |

| Ex. No. | Structure | Separation Method Starting Material | Analytical Data |
|---|---|---|---|
| 12 | Enantiomer 1 | HPLC Method E3; 4-amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile (Example 32) | $^1$HNMR (400 MHz, DMSO-$d_6$): 1.83 (d, 3H), 5.02 (q, 1H), 7.31-7.44 (m, 3H), 7.73 (m, 2H), 8.17 (m, 2H), 9.16 (s, 2H). LCMS m/z = 494.2 [MH]$^+$; RT [HPLC Method E1] = 4.251 min. |
| 13 | Enantiomer 2 | HPLC Method E3; 4-amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile (Example 32) | $^1$HNMR (400 MHz, DMSO-$d_6$): 1.84 (d, 3H), 5.02 (q, 1H), 7.31-7.43 (m, 3H), 7.73 (m, 2H), 8.17 (m, 2H), 9.16 (s, 2H). LCMS m/z = 494.2 [MH]$^+$; RT [HPLC Method E1] = 5.714 min. |
| 14 | Enantiomer 1 | HPLC Method C27; 4-amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile (Example 33) | $^1$HNMR (400 MHz, CDCl$_3$): 1.04 (t, 3H), 2.46 (m, 2H), 4.84 (t, 1H), 5.60 (br s, 2H), 7.21-7.26 (m, 3H), 7.78 (s, 1H), 7.83 (m, 1H), 8.10 (d, 1H), 8.15 (s, 1H), 9.10 (s, 2H). LCMS m/z = 508.1 [MH]$^+$; RT [HPLC Method C13] = 3.531 min. |

-continued

| Ex. No. | Structure | Separation Method Starting Material | Analytical Data |
|---|---|---|---|
| 15 | 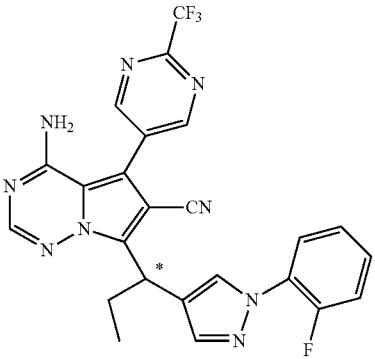 Enantiomer 2 | HPLC Method C27; 4-amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile (Example 33) | $^1$HNMR (400 MHz, CDCl$_3$): 1.04 (t, 3H), 2.46 (m, 2H), 4.84 (t, 1H), 5.60 (br s, 2H), 7.21-7.26 (m, 3H), 7.78 (s, 1H), 7.83 (m, 1H), 8.10 (d, 1H), 8.15 (s, 1H), 9.10 (s, 2H). LCMS m/z = 508.1 [MH]$^+$; RT [HPLC Method C13] = 4.883 min. |
| 16 | 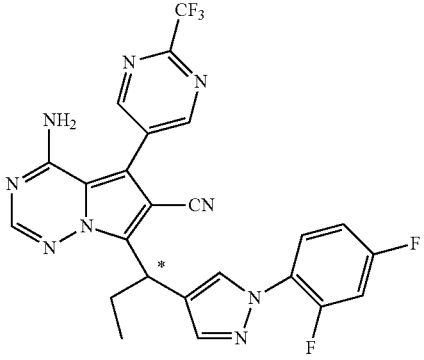 Enantiomer 1 | HPLC Method C27; 4-amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile (Example 34) | $^1$HNMR (400 MHz, MeOD-d$_4$): 1.02 (t, 3H), 2.34-2.41 (m, 1H), 2.43-2.52 (m, 1H), 4.90 (m, 1H), 7.10 (m, 1H), 7.21 (m, 1H), 7.70-7.77 (m, 2H), 8.07 (d, 2H), 9.12 (s, 2H). LCMS m/z = 526.1 [MH]$^+$; RT [HPLC Method C13] = 2.725 min. |
| 17 | 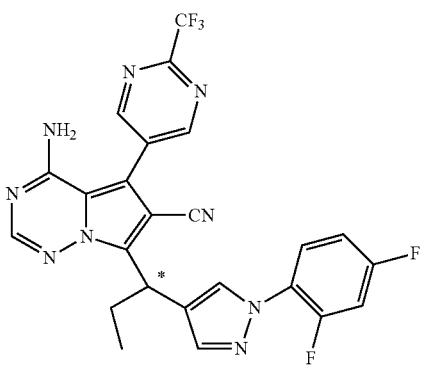 Enantiomer 2 | HPLC Method C27; 4-amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile (Example 34) | $^1$HNMR (400 MHz, MeOD-d$_4$): 1.02 (t, 3H), 2.34-2.41 (m, 1H), 2.43-2.52 (m, 1H), 4.90 (m, 1H), 7.10 (m, 1H), 7.21 (m, 1H), 7.70-7.77 (m, 2H), 8.07 (d, 2H), 9.12 (s, 2H). LCMS m/z = 526.1 [MH]$^+$; RT [HPLC Method C13] = 3.369 min. |

| Ex. No. | Structure | Separation Method Starting Material | Analytical Data |
|---|---|---|---|
| 18 | 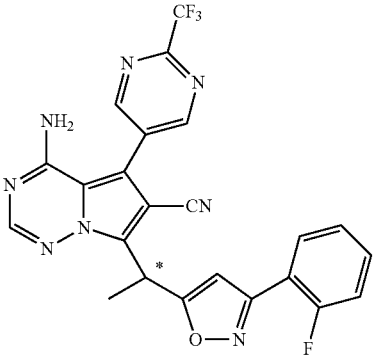 Enantiomer 1 | HPLC Method D7; 4-amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile (Example 36) | $^1$HNMR (400 MHz, DMSO-$d_6$): 1.90 (d, 3H), 5.32 (m, 1H), 6.93 (s, 1H), 7.32-7.40 (m, 2H), 7.54 (m, 1H), 7.85 (m, 1H), 8.19 (s, 1H), 9.19 (s, 2H). LCMS m/z = 495.0 [MH]$^+$ RT [HPLC Method D2] = 4.311 min. |
| 19 | 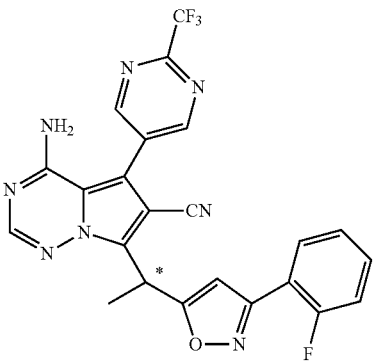 Enantiomer 2 | HPLC Method D7; 4-amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile (Example 36) | $^1$HNMR (400 MHz, DMSO-$d_6$): 1.90 (d, 3H), 5.32 (m, 1H), 6.93 (s, 1H), 7.32-7.40 (m, 2H), 7.54 (m, 1H), 7.85 (m, 1H), 8.19 (s, 1H), 9.19 (s, 2H). LCMS m/z = 495.0 [MH]$^+$; RT [HPLC Method D2] = 5.260 min. |

Example 20 and Example 21: 4-Amino-7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazine-6-carbonitrile, Enantiomers 1 and 2

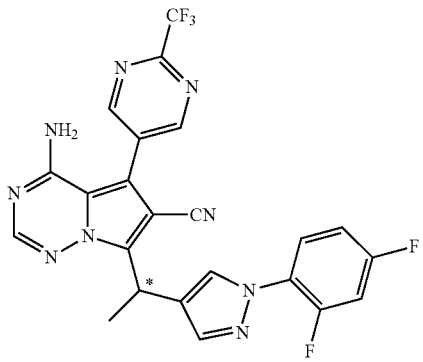 [SMILES: CC(c1cnn(-c2ccc(F)cc2F)c1)c1c(C#N)c(-c2cnc(C(F)(F)F)nc2)c2c(N)ncnn12]

To a mixture of 6-bromo-7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazin-4-amine (Example 47, 250 mg, 0.442 mmol), Pd$_2$(dba)$_3$ (202.4 mg, 0.22 mmol) and dppf (245 mg, 0.44 mmol) in NMP (10 mL) was added Zn(CN)$_2$ (208 mg, 1.768 mmol) and the reaction stirred at 160° C. for 3 hr under MW irradiation under N$_2$. The cooled mixture was filtered, washing through with EtOAc, the filtrate poured into water and extracted with EtOAc (30 mL×3). The combined organic extracts were dried (Na$_2$SO$_4$), filtered and evaporated under reduced pressure. The crude product was purified by column chromatography on silica gel eluting with EtOAc:pet. ether (30:70 to 100:0) to provide a yellow solid (75 mg, 33.18%). This solid was further purified by HPLC Method D5, to afford Example 20, enantiomer 1. $^1$HNMR (400 MHz, MeOD-$d_4$): 1.91 (d, 3H), 5.14 (q, 1H), 7.10 (m, 1H), 7.17 (m, 1H), 7.72 (m, 2H), 8.05 (s, 1H), 8.09 (s, 1H), 9.10 (s, 2H). LCMS m/z=512.0 [MH]$^+$; RT [HPLC Method D2]=9.308 min.

Further elution provided Example 21, enantiomer 2. $^1$HNMR (400 MHz, MeOD-$d_4$): 1.91 (d, 3H), 5.14 (q, 1H), 7.10 (m, 1H), 7.17 (m, 1H), 7.72 (m, 2H), 8.05 (s, 1H), 8.09 (s, 1H), 9.10 (s, 2H). LCMS m/z=512.0 [MH]$^+$; RT [HPLC Method D2]=12.255 min.

Examples 22 to 31

To a solution of the appropriate bromide starting material (1 eq) in DMF (10 mL/mmol SM), was slowly added Zn(CN)$_2$ (1.5-3 eq), dppf (0.1-0.2 eq) and Pd$_2$(dba)$_3$ (0.1 eq) and the reaction stirred at 140-150° C. for 1.5-2 hrs under microwave irradiation. The reaction was filtered, the residue partitioned between EtOAc and H$_2$O, the layers separated, the aqueous phase extracted with EtOAc, and the combined organics dried (Na$_2$SO$_4$), filtered and concentrated in vacuo. The crude product was purified by column chromatography on silica gel eluting with EtOAc:pet. ether at a suitable gradient to afford the desired compound.

| Ex. No. | Structure | Starting material | Analytical Data |
|---|---|---|---|
| 22[a] | 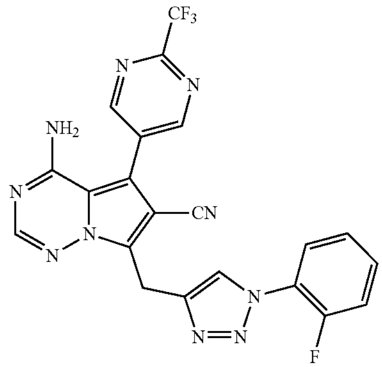 [SMILES: N#Cc1c(-c2cnc(C(F)(F)F)nc2)c2c(N)ncnn2c1Cc1cn(-c2ccccc2F)nn1] | 6-bromo-7-{[1-(2-fluorophenyl)-1H-1,2,3-triazol-4-yl]methyl}-5-[2-(trifluoromethyl)pyrimidin-5-yl]pyrrolo[2,1-f][1,2,4]triazin-4-amine (Example 37) | $^1$HNMR (400 MHz, MeOD-$d_4$): 4.73 (s, 2H), 7.40-7.47 (m, 2H), 7.56 (m, 1H), 7.82 (m, 1H), 8.12 (s, 1H), 8.40 (s, 1H), 9.16 (s, 2H). LCMS m/z = 481.1 [MH]$^+$; RT [HPLC Method A] = 1.565 min. |
| 23 | 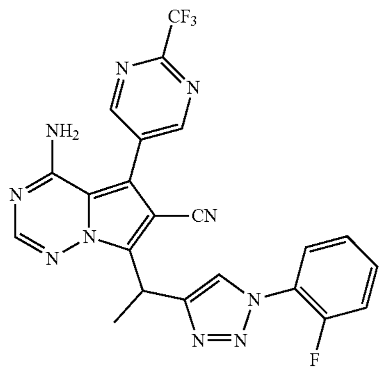 [SMILES: CC(c1cn(-c2ccccc2F)nn1)c1c(C#N)c(-c2cnc(C(F)(F)F)nc2)c2c(N)ncnn12] | 6-bromo-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 38) | $^1$HNMR (400 MHz, DMSO-$d_6$): 1.88 (d, 3H), 5.21 (q, 1H), 6.95-7.10 (br s, 2H), 7.43 (m, 1H), 7.56-7.63 (m, 2H), 7.77 (m, 1H), 8.18 (s, 1H), 8.61 (s, 1H), 9.16 (s, 2H). LCMS m/z = 495.1 [MH]$^+$ |
| 24 | 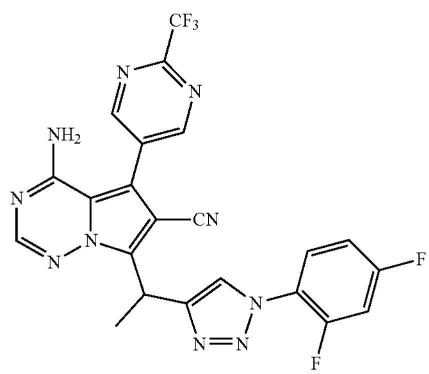 [SMILES: CC(c1cn(-c2ccc(F)cc2F)nn1)c1c(C#N)c(-c2cnc(C(F)(F)F)nc2)c2c(N)ncnn12] | 6-bromo-7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 39) | $^1$HNMR (400 MHz, DMSO-$d_6$): 1.87 (d, 3H), 5.20 (m, 1H), 6.95-7.05 (br s, 2H), 7.09 (m, 1H), 7.33 (m, 1H), 7.66 (m, 1H), 8.18 (s, 1H), 8.61 (s, 1H), 9.16 (s, 2H). LCMS m/z = 513.2 [MH]$^+$ |
| 25[b,c] | 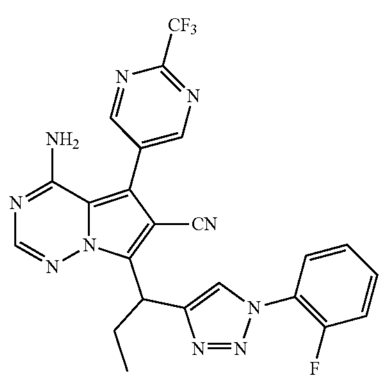 [SMILES: CCC(c1cn(-c2ccccc2F)nn1)c1c(C#N)c(-c2cnc(C(F)(F)F)nc2)c2c(N)ncnn12] | 6-bromo-7-{1-[1-(2-fluorophenyl)-1H-1,2,3-triazol-4-yl]propyl}-5-[2-(trifluoromethyl)pyrimidin-5yl]pyrrolo[2,1-f][1,2,4]triazin-4-amine (Example 40) | $^1$HNMR (400 MHz, MeOD-$d_4$): 1.10 (t, 3H), 2.04 (m, 2H), 5.20 (m, 1H), 7.38-7.48 (m, 2H), 7.62 (m, 1H), 7.82 (m, 1H), 8.18 (s, 1H), 8.49 (s, 1H), 9.20 (s, 2H). LCMS m/z = 509.1 [MH]$^+$; RT [HPLC Method A] = 1.699 min. |

| Ex. No. | Structure | Starting material | Analytical Data |
|---|---|---|---|
| 26[b] | 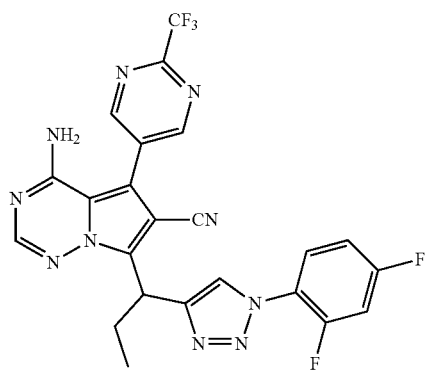 [SMILES: CCC(c1cn(-c2ccc(F)cc2F)nn1)c1c(C#N)c(-c2cnc(C(F)(F)F)nc2)c2c(N)ncnn12] | 6-bromo-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 41) | LCMS m/z = 527.0 [MH]+ |
| 27[b] | 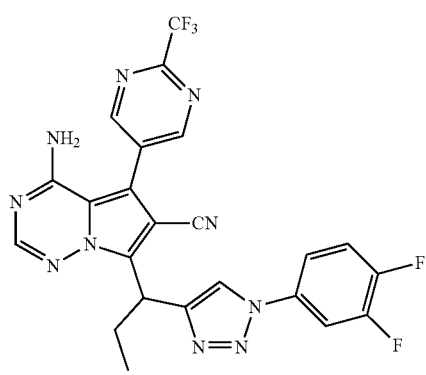 [SMILES: CCC(c1cn(-c2ccc(F)c(F)c2)nn1)c1c(C#N)c(-c2cnc(C(F)(F)F)nc2)c2c(N)ncnn12] | 6-bromo-7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 43) | LCMS m/z = 527.0 [MH]+ |
| 28 | 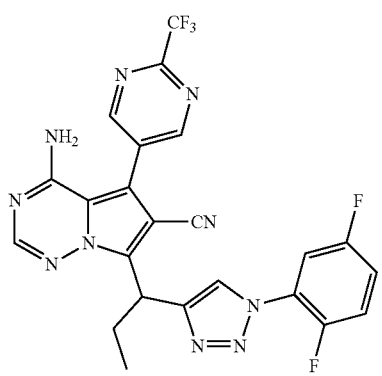 [SMILES: CCC(c1cn(-c2cc(F)ccc2F)nn1)c1c(C#N)c(-c2cnc(C(F)(F)F)nc2)c2c(N)ncnn12] | 6-bromo-7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 42) | LCMS m/z = 527.0 [MH]+ |
| 29[b] | 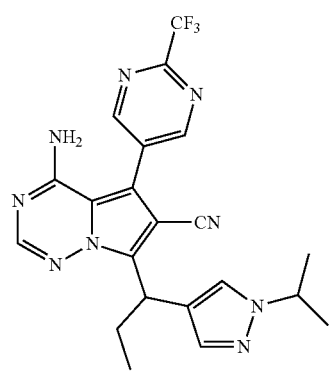 [SMILES: CCC(c1cnn(C(C)C)c1)c1c(C#N)c(-c2cnc(C(F)(F)F)nc2)c2c(N)ncnn12] | 6-bromo-7-{1-[1-(propan-2-yl)-1H-pyrazol-4-yl]propyl}-5-[2-(trifluoromethyl)pyrimidin-5-yl]pyrrolo[2,1-f][1,2,4]triazin-4-amine (Example 50) | $^1$HNMR (400 MHz, MeOD-d$_4$): 0.99 (t, 3H), 1.46 (d, 6H), 2.28-2.41 (m, 2H), 4.47 (m, 1H), 4.84 (m, 1H), 7.49 (s, 1H), 7.71 (s, 1H), 8.08 (s, 1H), 9.12 (s, 2H). LCMS m/z = 456.2 [MH]+ |

| Ex. No. | Structure | Starting material | Analytical Data |
|---|---|---|---|
| 30 | 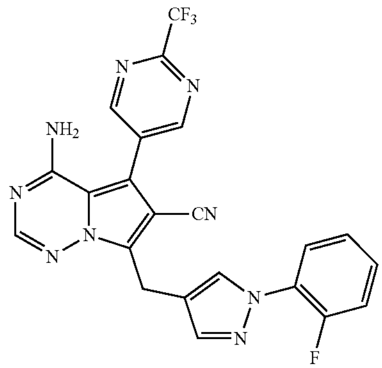 [SMILES: N#Cc1c(-c2cnc(C(F)(F)F)nc2)c2c(N)ncnn2c1Cc1cnn(-c2ccccc2F)c1] | 6-bromo-7-{[1-(2-fluorophenyl)-1H-pyrazol-4-yl]methyl}-5-[2-(trifluoromethyl)pyrimidin-5-yl]pyrrolo[2,1-f][1,2,4]triazine-4-amine (Example 44) | $^1$HNMR (400 MHz, DMSO-$d_6$): 4.38 (s, 2H), 7.33-7.43 (m, 3H), 7.75 (m, 2H), 8.14 (s, 1H), 8.20 (s, 1H), 9.17 (s, 2H). |
| 31 | 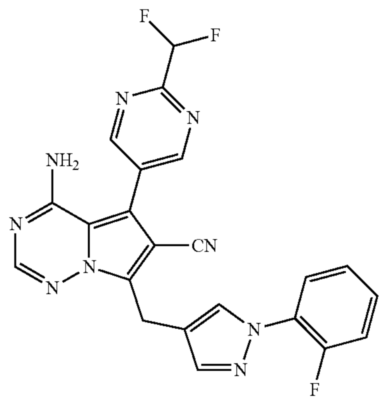 [SMILES: N#Cc1c(-c2cnc(C(F)F)nc2)c2c(N)ncnn2c1Cc1cnn(-c2ccccc2F)c1] | 6-bromo-5-[2-(difluoromethyl)pyrimidin-5-yl]-7-{[1-(2-fluorophenyl)-1H-pyrazol-4-yl]methyl}pyrrolo[2,1-f][1,2,4]triazine-4-amine (Example 45) | $^1$HNMR (400 MHz, DMSO-$d_6$): 4.37 (s, 2H), 6.94-7.21 (dd, 1H), 7.31-7.45 (m, 5H), 7.72 (m, 2H), 8.13-8.15 (m, 2H), 9.07 (s, 2H). LCMS m/z = 462.2 [MH]$^+$ |

$^a$DCM:MeOH was used as the column solvent, $^b$NMP was used as the reaction, solvent, $^c$Pd(dppf)Cl$_2$ was used instead of Pd$_2$(dba)$_3$.

Example 32: 4-Amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile

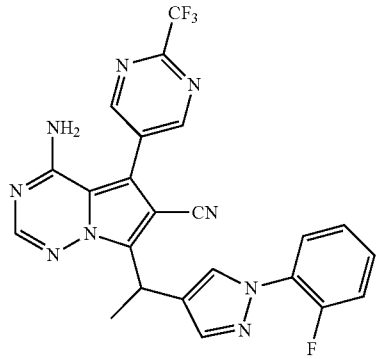 [SMILES: CC(c1cnn(-c2ccccc2F)c1)c1c(C#N)c(-c2cnc(C(F)(F)F)nc2)c2c(N)ncnn12]

To a solution of 6-bromo-7-{1-[1-(2-fluorophenyl)-1H-pyrazol-4-yl]ethyl}-5-[2-(trifluoromethyl)pyrimidin-5-yl]pyrrolo[2,1-f][1,2,4]triazin-4-amine (Example 46, 270 mg, 0.49 mmol) in NMP (15 mL), in a microwave vial, was added Zn(CN)$_2$ (173 mg, 1.47 mmol), dppf (56 mg, 0.1 mmol) and Pd$_2$(dba)$_3$ (46 mg, 0.05 mmol). The sealed vial was irradiated in the microwave at 140° C. for 2 hrs. The cooled mixture was diluted with water (10 mL), and extracted with DCM (15 mL×2). The combined organic extracts were washed with brine (60 mL), dried (Na$_2$SO$_4$), filtered and evaporated under reduced pressure. The residue was purified by column chromatography on silica gel eluting with EtOAc:pet. ether (10:90 to 90:10) to afford the title compound as a white solid (170 mg, yield 70%). LCMS m/z=494.1 [MH]$^+$ Example 33: 4-Amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile

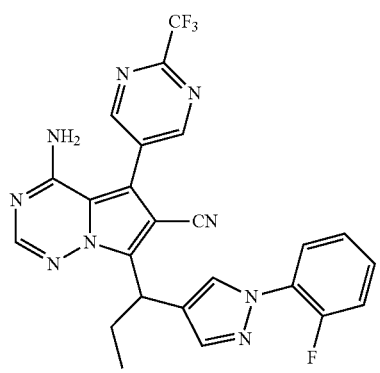 [SMILES: CCC(c1cnn(-c2ccccc2F)c1)c1c(C#N)c(-c2cnc(C(F)(F)F)nc2)c2c(N)ncnn12]

The title compound was prepared as a yellow solid (50 mg, 66% yield) from 6-bromo-7-{1-[1-(2-fluorophenyl)-

1H-pyrazol-4-yl]propyl}-5-[2-(trifluoromethyl)pyrimidin-5-yl]pyrrolo[2,1-f][1,2,4]triazin-4-amine (Example 48), following a similar procedure to that described in Example 32. LCMS m/z=508.1 [MH]+

Example 34: 4-Amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile

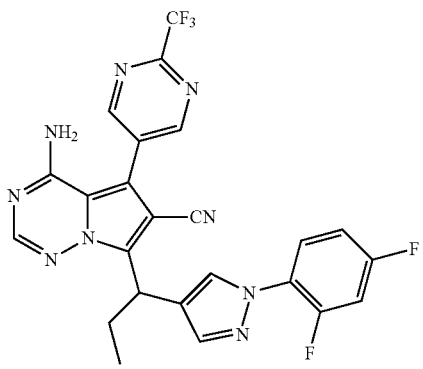 [SMILES: CCC(c1cnn(-c2ccc(F)cc2F)c1)c1c(C#N)c(-c2cnc(C(F)(F)F)nc2)c2c(N)ncnn12]

To a mixture of 6-bromo-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazin-4-amine (Example 49, 250 mg, 0.43 mmol), Pd$_2$(dba)$_3$ (197 mg, 0.215 mmol) and dppf (238 mg, 0.43 mmol) in NMP (10 mL) was added Zn(CN)$_2$ (202 mg, 1.72 mmol) and the reaction stirred at 160° C. for 3 hr under microwave irradiation under N2. The cooled mixture was filtered, washing through with EtOAc, the filtrate poured into water and extracted with EtOAc (30 mL×3). The combined organic extracts were dried (Na$_2$SO$_4$), filtered and concentrated in vacuo. The crude product was purified by column chromatography on silica gel eluting with EtOAc:Pet. Ether (30:70 to 0:100) to provide the desired compound as a yellow solid (90 mg, 39.83%). $^1$HNMR (400 MHz, MeOD-d$_4$): 1.02 (t, 3H), 2.34-2.41 (m, 1H), 2.43-2.52 (m, 1H), 4.90 (m, 1H), 7.10 (m, 1H), 7.21 (m, 1H), 7.70-7.77 (m, 2H), 8.07 (d, 2H), 9.12 (s, 2H). LCMS m/z=526.1 [MH]+

Example 35: 4-Amino-7-{[3-(2-fluorophenyl)-1,2-oxazol-5-yl]methyl}-5-[2-(trifluoromethyl)pyrimidin-5-yl]pyrrolo[2,1-f][1,2,4]triazine-6-carbonitrile

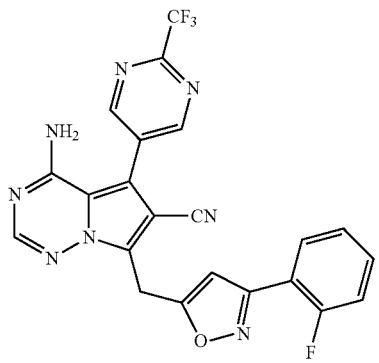 [SMILES: N#Cc1c(-c2cnc(C(F)(F)F)nc2)c2c(N)ncnn2c1Cc1cc(-c2ccccc2F)no1]

To a solution of 6-bromo-7-{[3-(2-fluorophenyl)-1,2-oxazol-5-yl]methyl}-5-[2-(trifluoromethyl)pyrimidin-5-yl]pyrrolo[2,1-f][1,2,4]triazin-4-amine (Example 51, 120 mg, 0.225 mmol) in DMF (5 mL) was slowly added CuCN (20 mg, 0.45 mmol) and the reaction stirred at 160° C. for 4 hr under microwave irradiation. EtOAc (100 mL) was added to the cooled mixture and the solution washed with aq. NH$_3$ (50 mL), dried (Na$_2$SO$_4$) and concentrated in vacuo. The crude product was purified by column chromatography on silica gel eluting with DCM:MeOH (91:9) to afford the title compound as a white solid (11.2 mg, 10%). $^1$HNMR (400 MHz, DMSO-d$_6$): 4.79 (s, 2H), 6.82 (s, 1H), 7.32-7.42 (m, 2H), 7.54 (m, 1H), 7.84 (m, 1H), 8.20 (s, 1H), 9.20 (s, 2H). LCMS m/z=481.0 [MH]+

Example 36: 4-Amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile

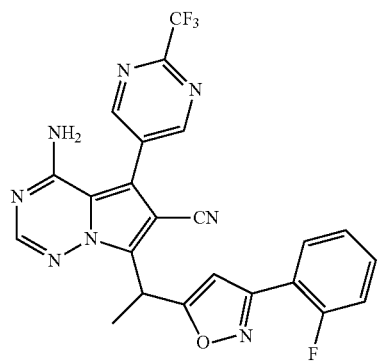 [SMILES: CC(c1cc(-c2ccccc2F)no1)c1c(C#N)c(-c2cnc(C(F)(F)F)nc2)c2c(N)ncnn12]

To a solution of 6-bromo-7-{1-[3-(2-fluorophenyl)-1,2-oxazol-5-yl]ethyl}-5-[2-(trifluoromethyl)pyrimidin-5-yl]pyrrolo[2,1-f][1,2,4]triazin-4-amine (Example 52, 1.0 g, 1.83 mmol) in NMP (15 mL) was added Zn(CN)$_2$ (0.32 g, 2.74 mmol) and Pd(PPh$_3$)$_4$ (0.2 g, 0.183 mmol) and the reaction stirred at 160° C. for 2 hrs under microwave irradiation. The cooled mixture was filtered, water and EtOAc (100 mL) added, the layers separated, and the organic phase washed with brine, dried (Na$_2$SO$_4$) and concentrated in vacuo. The crude product was purified by column chromatography on silica gel eluting with Pet. Ether:EtOAc (34:66) to afford the title compound as a yellow solid (135 mg, 15%). LCMS m/z=495.0 [MH]+

Examples 37 to 52

To a solution of the appropriate triazine-4-amine starting material (1 eq) in DCM was added NBS (1.05-2.0 eq) drop wise at 0° C. and the mixture allowed to warm to rt and stirred until all starting material had been consumed. The mixture was quenched with aq. Na$_2$S$_2$O$_3$ solution and extracted with EtOAc. The organic layer was washed with brine (2×), dried (Na$_2$SO$_4$) and concentrated in vacuo. The crude product was purified by column chromatography on silica gel eluting with suitable solvents to afford the title compound.

| Ex. No. | Structure | Starting Material | Analytical Data |
|---|---|---|---|
| 37[a] | 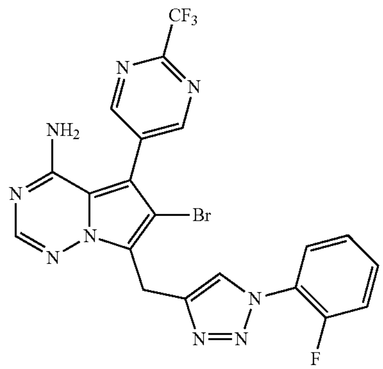 [SMILES: Nc1ncnn2c(Cc3cn(-c4ccccc4F)nn3)c(Br)c(-c3cnc(C(F)(F)F)nc3)c12] | 7-{[1-(2-fluorophenyl)-1H-1,2,3-triazol-4-yl]methyl}-5-[2-(trifluoromethyl)pyrimidin-5-yl]pyrrolo[2,1-f][1,2,4]triazin-4-amine (Example 81) | LCMS m/z = 534.0, 536.0 [MH]+ |
| 38[b] | 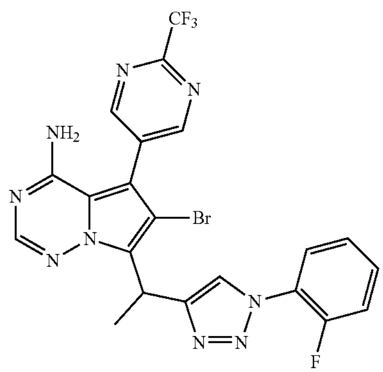 [SMILES: CC(c1cn(-c2ccccc2F)nn1)c1c(Br)c(-c2cnc(C(F)(F)F)nc2)c2c(N)ncnn12] | 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 69) | 1HNMR (400 MHz, DMSO-$d_6$): 1.86 (d, 3H), 5.16 (q, 1H), 7.05-7.15 (br s, 1H), 7.42 (m, 1H), 7.53-7.61 (m, 2H), 7.78 (m, 1H), 8.03 (s, 1H), 8.49 (s, 1H), 9.07 (s, 2H). LCMS m/z = 548.1, 550.1 [MH]+ |
| 39 | 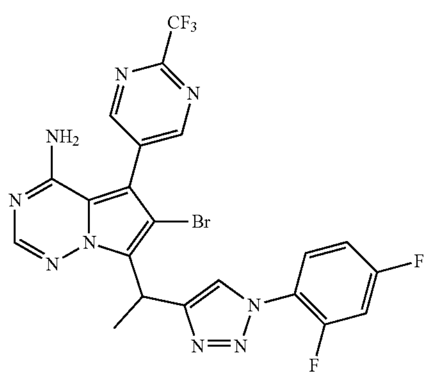 [SMILES: CC(c1cn(-c2ccc(F)cc2F)nn1)c1c(Br)c(-c2cnc(C(F)(F)F)nc2)c2c(N)ncnn12] | 7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 70) | 1HNMR (400 MHz, DMSO-$d_6$): 1.85 (d, 3H), 5.15 (q, 1H), 7.34 (m, 1H), 7.64-7.70 (m, 1H), 7.95 (m, 1H), 8.03 (s, 1H), 8.48 (s, 1H), 9.07 (s, 2H). LCMS m/z = 566.1, 568.1 [MH]+ |
| 40[c] | 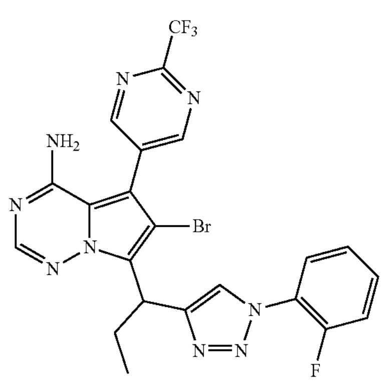 [SMILES: CCC(c1cn(-c2ccccc2F)nn1)c1c(Br)c(-c2cnc(C(F)(F)F)nc2)c2c(N)ncnn12] | 7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine (Example 82) | LCMS m/z = 562.0, 564.0 [MH]+ |

-continued

| Ex. No. | Structure | Starting Material | Analytical Data |
|---|---|---|---|
| 41 | 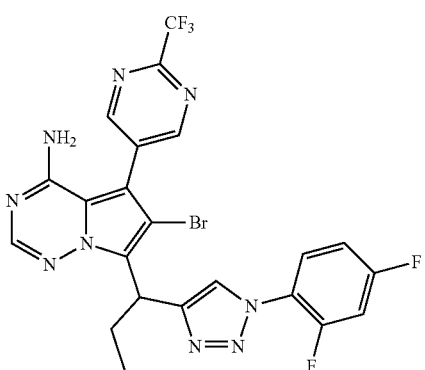 | 7-{1-[1-(2,4-difluoro-phenyl)-1H-1,2,3-triazol-4-yl]propyl}-5-[2-(trifluoro-methyl)pyrimidin-5-yl] pyrrolo[2,1-f][1,2,4]triazin-4-amine (Example 84) | LCMS m/z = 580.0 [MH]+; RT [HPLC Method A] = 1.794 min. |
| 42[a] | 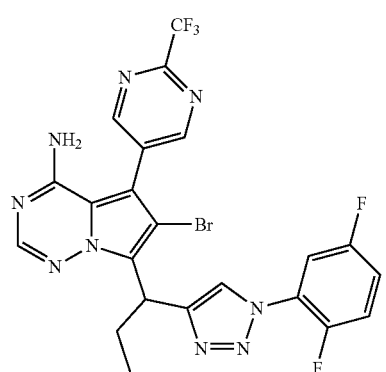 | 7-{1-[1-(2,5-difluoro-phenyl)-1H-1,2,3-triazol-4-yl]propyl}-5-[2-(trifluoro-methyl)pyrimidin-5-yl] pyrrolo[2,1-f][1,2,4]triazin-4-amine (Example 71) | LCMS m/z = 579.9, 582.0 [MH]+ |
| 43 | 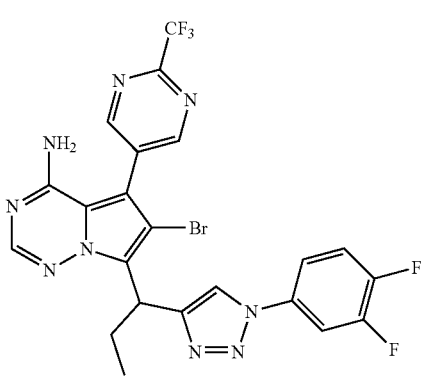 | 7-{1-[1-(3,4-difluoro-phenyl)-1H-1,2,3-triazol-4-yl]propyl}-5-[2-(trifluoro-methyl)pyrimidin-5-yl] pyrrolo[2,1-f][1,2,4]triazin-4-amine (Example 72) | LCMS m/z = 579.9, 582.0 [MH]+ |
| 44 | 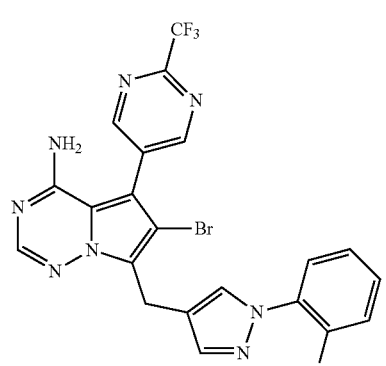 | 7-{[1-(2-fluorophenyl)-1H-pyrazol-4-yl]methyl}-5-[2-(trifluoromethyl) pyrimidin-5-yl]pyrrolo[2,1-f][1,2,4]triazin-4-amine (Example 75) | 1HNMR (400 MHz, MeOD-d4): 4.48 (s, 2H), 7.29-7.39 (m, 3H), 7.72 (m, 2H), 8.09 (s, 1H), 8.13 (s, 1H), 9.14 (s, 2H). LCMS m/z = 533.0 [MH]+ |

| Ex. No. | Structure | Starting Material | Analytical Data |
|---|---|---|---|
| 45[b] | 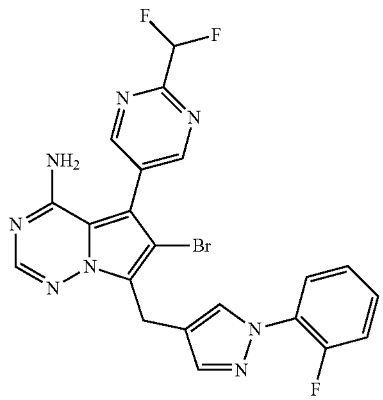 [SMILES: Nc1ncnn2c(Cc3cnn(-c4ccccc4F)c3)c(Br)c(-c3cnc(C(F)F)nc3)c12] | 5-[2-(difluoromethyl)pyrimidin-5-yl]-7-{[1-(2-fluorophenyl)-1H-pyrazol-4-yl]methyl}pyrrolo[2,1-f][1,2,4]triazin-4-amine (Example 76) | LCMS m/z = 515.1 [MH]+ |
| 46 | 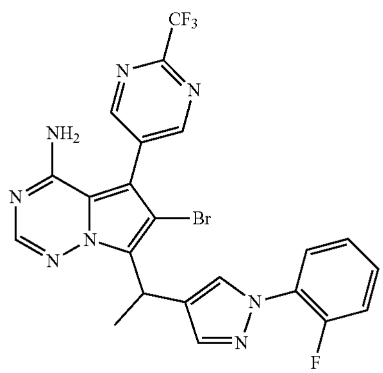 [SMILES: CC(c1cnn(-c2ccccc2F)c1)c1c(Br)c(-c2cnc(C(F)(F)F)nc2)c2c(N)ncnn12] | 7-{1-[1-(2-fluorophenyl)-1H-pyrazol-4-yl]ethyl}-5-[2-(trifluoromethyl)pyrimidin-5-yl]pyrrolo[2,1-f][1,2,4]triazin-4-amine (Example 77) | LCMS m/z = 549.0 [MH]+ |
| 47[a] | 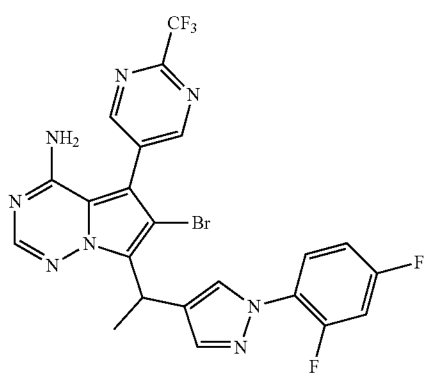 [SMILES: CC(c1cnn(-c2ccc(F)cc2F)c1)c1c(Br)c(-c2cnc(C(F)(F)F)nc2)c2c(N)ncnn12] | 7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazin-4-amine (Example 85) | LCMS m/z = 566.9 [MH]+ |
| 48[b] | 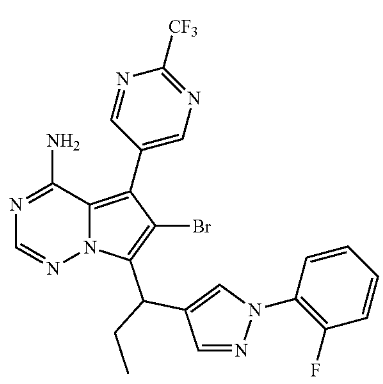 [SMILES: CCC(c1cnn(-c2ccccc2F)c1)c1c(Br)c(-c2cnc(C(F)(F)F)nc2)c2c(N)ncnn12] | 7-{1-[1-(2-fluorophenyl)-1H-pyrazol-4-yl]propyl}-5-[2-(trifluoromethyl)pyrimidin-5-yl]pyrrolo[2,1-f][1,2,4]triazin-4-amine (Example 78) | LCMS m/z = 561.9 [MH]+ |

-continued

| Ex. No. | Structure | Starting Material | Analytical Data |
|---|---|---|---|
| 49[a] | 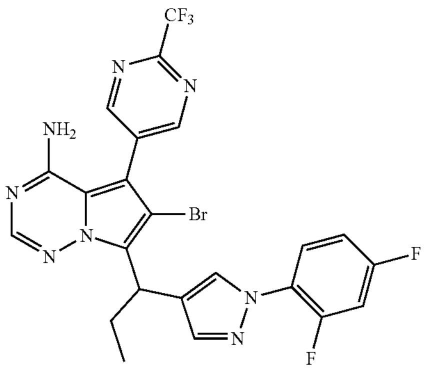 [SMILES: CCC(c1cnn(-c2ccc(F)cc2F)c1)c1c(Br)c(-c2cnc(C(F)(F)F)nc2)c2c(N)ncnn12] | 7-{1-[1-(2,4-difluorophenyl)-1H-pyrazol-4-yl]propyl}-5-[2-(trifluoromethyl)pyrimidin-5-yl]pyrrolo[2,1-f][1,2,4]triazin-4-amine (Example 86) | LCMS m/z = 579.0 [MH]+ |
| 50 | 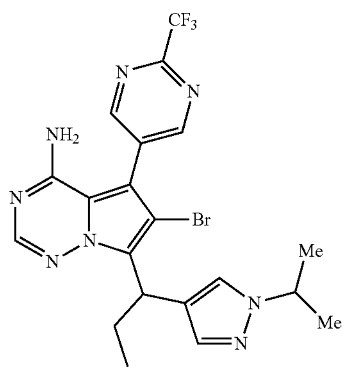 [SMILES: CCC(c1cnn(C(C)C)c1)c1c(Br)c(-c2cnc(C(F)(F)F)nc2)c2c(N)ncnn12] | 7-{1-[1-(propan-2-yl)-1H-pyrazol-4-yl]propyl}-5-[2-(trifluoromethyl)pyrimidin-5-yl]pyrrolo[2,1-f][1,2,4]triazin-4-amine (Example 74) | $^1$HNMR (400 MHz, DMSO-d$_6$): 0.81 (t, 3H), 1.35 (d, 6H), 2.13-2.23 (m, 1H), 2.39-2.44 (m, 1H), 4.37-4.44 (m, 1H), 4.58-4.62 (m, 1H), 7.35 (s, 1H), 7.63 (s, 1H), 8.04 (s, 1H), 9.06 (s, 1H). LCMS m/z = 509.0 [MH]+ |
| 51[a] | 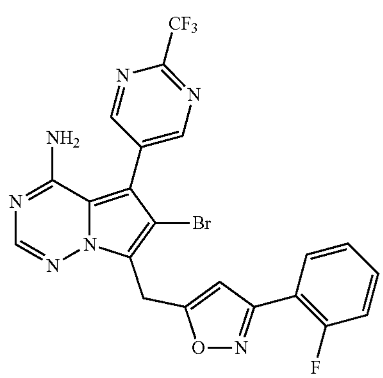 [SMILES: Nc1ncnn2c(Cc3cc(-c4ccccc4F)no3)c(Br)c(-c3cnc(C(F)(F)F)nc3)c12] | 7-{[3-(2-fluorophenyl)-1,2-oxazol-5-yl]methyl}-5-[2-(trifluoromethyl)pyrimidin-5-yl]pyrrolo[2,1-f][1,2,4]triazin-4-amine (Example 80) | LCMS m/z = 533.9 [MH]+ |
| 52[c] | 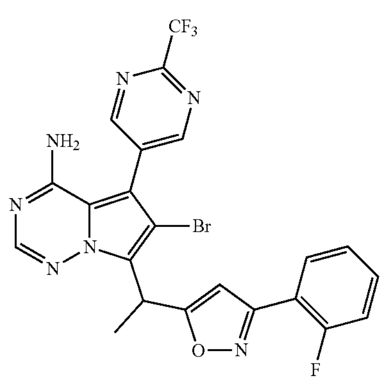 [SMILES: CC(c1cc(-c2ccccc2F)no1)c1c(Br)c(-c2cnc(C(F)(F)F)nc2)c2c(N)ncnn12] | 7-{1-[3-(2-fluorophenyl)-1,2-oxazol-5-yl]ethyl}-5-[2-(trifluoromethyl)pyrimidin-5-yl]pyrrolo[2,1-f][1,2,4]triazin-4-amine (Example 79) | $^1$HNMR (400 MHz, DMSO-d$_6$): 1.88 (d, 3H), 5.22 (q, 1H), 6.85 (d, 1H), 7.33-7.39 (m, 2H), 7.54 (m, 1H), 7.87 (m, 1H), 8.06 (s, 1H), 9.08 (s, 2H). LCMS m/z = 548.0, 550.0 [MH]+ |

[a]DMF was used as the reaction solvent, [b]DMF/DCM was used as the reaction solvent, [c]THF was used as the reaction solvent Examples 53 to 68

The following compounds were obtained by chiral separation of the corresponding racemic starting material, using the HPLC methods previously described.

| Ex. No. | Structure | Separation Method Starting Material | Analytical Data |
|---|---|---|---|
| 53 | 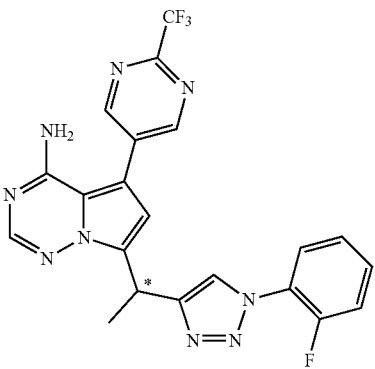<br>Enantiomer 1 | HPLC Method C20A; 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 69) | $^1$HNMR (400 MHz, DMSO-$d_6$): 1.77 (d, 3H), 4.97 (q, 1H), 6.90 (s, 1H), 7.20-7.30 (br s, 2H), 7.48 (m, 1H), 7.52-7.58 (m, 2H), 7.80 (m, 1H), 8.04 (s, 1H), 8.45 (s, 1H), 9.04 (s, 2H). LCMS m/z = 470.2 [MH]$^+$; RT [HPLC Method C5] = 2.579 min. |
| 54 | 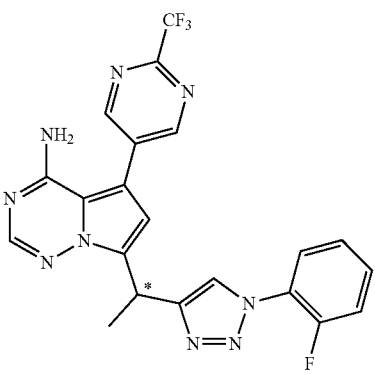<br>Enantiomer 2 | HPLC Method C20A; 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine (Example 69) | $^1$HNMR (400 MHz, DMSO-$d_6$): 1.77 (d, 3H), 4.97 (q, 1H), 6.90 (s, 1H), 7.20-7.30 (br s, 2H), 7.48 (m, 1H), 7.52-7.58 (m, 2H), 7.80 (m, 1H), 8.04 (s, 1H), 8.45 (s, 1H), 9.05 (s, 2H). LCMS m/z = 470.2 [MH]$^+$; RT [HPLC Method C5] = 3.109 min. |
| 55 | 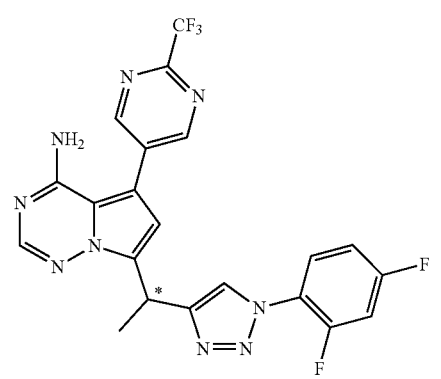 [SMILES: CC(c1cn(-c2ccc(F)cc2F)nn1)c1cc(-c2cnc(C(F)(F)F)nc2)c2c(N)ncnn12]<br>Enantiomer 1 | HPLC Method D6; 7-{1-[1-(2,4-Difluorophenyl)-1H-1,2,3-triazol-4-yl]ethyl}-5-[2-(trifluoromethyl) pyrimidin-5yl] pyrrolo[2,1-f][1,2,4]triazin-4-amine (Example 70) | $^1$HNMR (400 MHz, DMSO-$d_6$): 1.76 (d, 3H), 4.96 (q, 1H), 6.90 (s, 1H), 7.15-7.25 (br s, 2H), 7.32 (m, 1H), 7.63 (m, 1H), 7.68 (m, 1H), 8.04 (s, 1H), 8.43 (s, 1H), 9.04 (s, 2H). LCMS m/z = 488.2 [MH]$^+$; RT [HPLC Method B1] = 3.727 min. |

| Ex. No. | Structure | Separation Method Starting Material | Analytical Data |
|---|---|---|---|
| 56 | 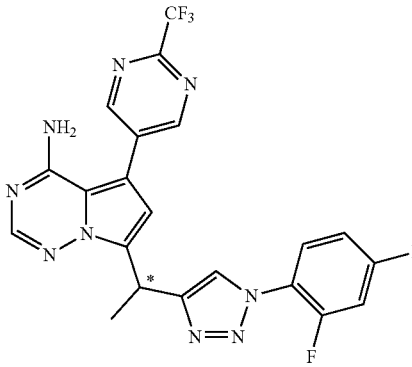<br>Enantiomer 2 | HPLC Method D6; 7-{1-[1-(2,4-Difluorophenyl)-1H-1,2,3-triazol-4-yl]ethyl}-5-[2-(trifluoromethyl) pyrimidin-5-yl] pyrrolo[2,1-f] [1,2,4]triazin-4-amine (Example 70) | $^1$HNMR (400 MHz, DMSO-$d_6$): 1.76 (d, 3H), 4.96 (q, 1H), 6.89 (s, 1H), 7.15-7.25 (br s, 2H), 7.30 (m, 1H), 7.63 (m, 1H), 7.67 (m, 1H), 8.04 (s, 1H), 8.43 (s, 1H), 9.05 (s, 2H). LCMS m/z = 488.2 [MH]$^+$; RT [HPLC Method B1] = 5.223 min. |
| 57 | 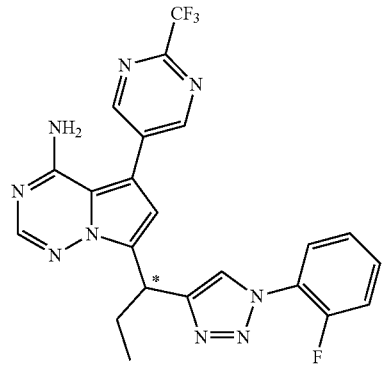<br>Enantiomer 1 | HPLC Method C23A; 7-{1-[1-(2-Fluorophenyl)-1H-1,2,3-triazol-4-yl]propyl}-5-[2-(trifluoromethyl)pyrimidin-5-yl]pyrrolo[2,1-f][1,2,4]triazin-4-amine (Example 82) | $^1$HNMR (400 MHz, DMSO-$d_6$): 0.93 (t, 3H), 2.20 (m, 2H), 4.82 (m, 1H), 6.97 (s, 1H), 7.25-7.35 (br s, 2H), 7.44 (m, 1H), 7.55 (m, 2H), 7.80 (m, 1H), 8.05 (s, 1H), 8.51 (s, 1H), 9.05 (s, 2H). LCMS m/z = 484.1 [MH]$^+$; RT [HPLC Method C2] = 2.421 min. |
| 58 | 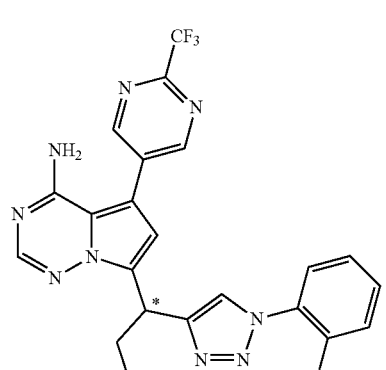<br>Enantiomer 2 | HPLC Method C23A; 7-{1-[1-(2-Fluorophenyl)-1H-1,2,3-triazol-4-yl]propyl}-5-[2-(trifluoromethyl)pyrimidin-5-yl]pyrrolo[2,1-f][1,2,4]triazin-4-amine (Example 82) | $^1$HNMR (400 MHz, DMSO-$d_6$): 0.93 (t, 3H), 2.20 (m, 2H), 4.82 (m, 1H), 6.97 (s, 1H), 7.25-7.35 (br s, 2H), 7.44 (m, 1H), 7.55 (m, 2H), 7.82 (m, 1H), 8.04 (s, 1H), 8.51 (s, 1H), 9.05 (s, 2H). LCMS m/z = 484.1 [MH]$^+$; RT [HPLC Method C2] = 2.778 min. |

-continued

| Ex. No. | Structure | Separation Method Starting Material | Analytical Data |
|---|---|---|---|
| 59 | 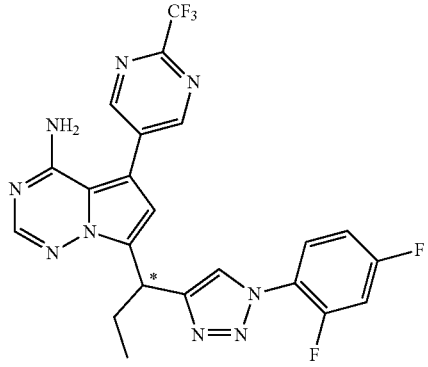Enantiomer 1 | HPLC-Method C24A; 7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 84) | $^1$HNMR (400 MHz, DMSO-$d_6$): 0.93 (t, 3H), 2.18 (t, 2H), 4.81 (t, 1H), 6.97 (s, 1H), 7.20-7.30 (br s, 2H), 7.31 (m, 1H), 7.63 (m, 1H), 7.85 (m, 1H), 8.04 (s, 1H), 8.48 (s, 1H), 9.05 (s, 2H). LCMS m/z = 502.2 [MH]$^+$; RT [HPLC Method C2] = 4.226 min. |
| 60 | 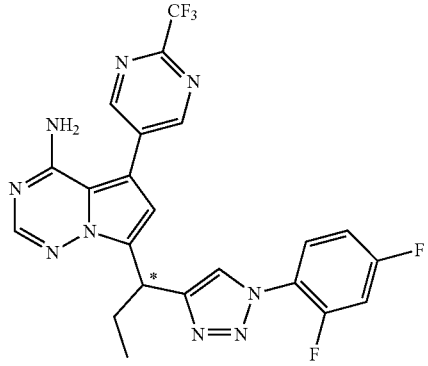Enantiomer 2 | HPLC-Method C24A; 7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 84) | $^1$HNMR (400 MHz, DMSO-$d_6$): 0.92 (t, 3H), 2.22 (t, 2H), 4.88 (t, 1H), 7.04 (s, 1H), 7.30-7.43 (m, 3H), 7.70 (m, 1H), 7.92 (m, 1H), 8.10 (s, 1H), 8.55 (s, 1H), 9.12 (s, 2H). LCMS m/z = 502.2 [MH]$^+$; RT [HPLC Method C2] = 5.438 min. |
| 61 | 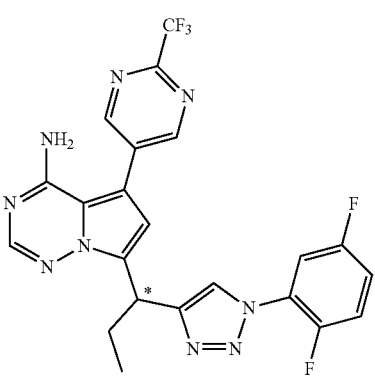 [SMILES: CCC(c1cn(-c2cc(F)ccc2F)nn1)c1cc(-c2cnc(C(F)(F)F)nc2)c2c(N)ncnn12]Enantiomer 1 | HPLC method C24B; 7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 71) | $^1$HNMR (400 MHz, DMSO-$d_6$): 0.93 (t, 3H), 2.18 (m, 2H), 4.82 (t, 1H), 6.96 (s, 1H), 7.20-7.30 (br s, 2H), 7.45 (m, 1H), 7.51 (m, 1H), 7.83 (m, 1H), 8.04 (s, 1H), 8.54 (s, 1H), 9.05 (s, 2H). LCMS m/z = 502.2 [MH]$^+$; RT [HPLC Method C1] = 4.137 min. |

| Ex. No. | Structure | Separation Method Starting Material | Analytical Data |
|---|---|---|---|
| 62 | 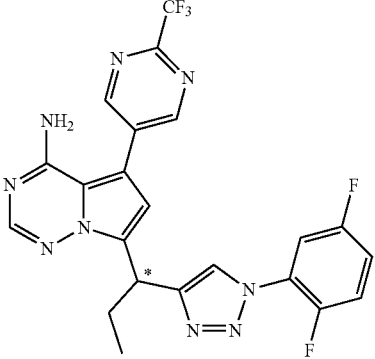<br>Enantiomer 2 | HPLC method C24B; 7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 71) | $^1$HNMR (400 MHz, DMSO-$d_6$): 0.93 (t, 3H), 2.18 (m, 2H), 4.82 (t, 1H), 6.96 (s, 1H), 7.20-7.30 (br s, 2H), 7.45 (m, 1H), 7.51 (m, 1H), 7.80 (m, 1H), 8.04 (s, 1H), 8.54 (s, 1H), 9.05 (s, 2H). LCMS m/z = 502.2 [MH]$^+$; RT [Method C1] = 5.389 min. |
| 63 | 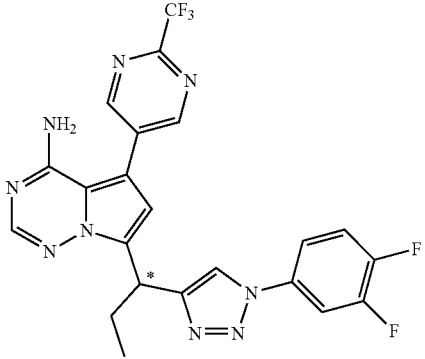 [SMILES: CCC(c1cn(-c2ccc(F)c(F)c2)nn1)c1cc(-c2cnc(C(F)(F)F)nc2)c2c(N)ncnn12]<br>Enantiomer 1 | HPLC Method C24B; 7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 72) | $^1$HNMR (400 MHz, DMSO-$d_6$): 0.93 (t, 3H), 2.18 (m, 2H), 4.79 (t, 1H), 6.95 (s, 1H), 7.20-7.30 (br s, 2H), 7.65-7.70 (m, 1H), 7.80 (m, 1H), 8.04 (s, 1H), 8.09 (m, 1H), 8.74 (s, 1H), 9.05 (s, 2H). LCMS m/z = 502.2 [MH]$^+$; RT [HPLC Method C1] = 4.201 min. |
| 64 | 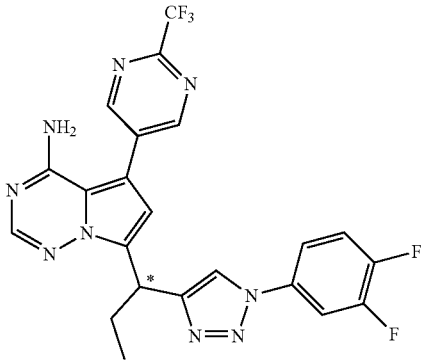<br>Enantiomer 2 | HPLC Method C24B; 7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine (Example 72) | $^1$HNMR (400 MHz, DMSO-$d_6$): 0.93 (t, 3H), 2.18 (m, 2H), 4.79 (t, 1H), 6.95 (s, 1H), 7.20-7.30 (br s, 2H), 7.65-7.72 (m, 1H), 7.81 (m, 1H), 8.04 (s, 1H), 8.09 (m, 1H), 8.74 (s, 1H), 9.05 (s, 2H). LCMS m/z = 502.2 [MH]$^+$; RT [HPLC Method C1] = 5.791 min. |
| 65$^a$ | 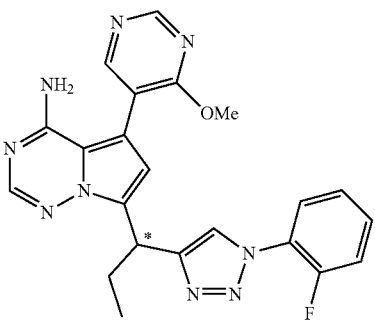<br>Enantiomer 1 | HPLC Method D4; 7-{1-[1-(2-Fluorophenyl)-1H-1,2,3-triazol-4-yl]propyl}-5-(4-methoxypyrimidin-5-yl)pyrrolo[2,1-f][1,2,4]triazin-4-amine (Example 83) | $^1$HNMR (400 MHz, MeOD-$d_4$): 1.03 (t, 3H), 2.32 (m, 2H), 4.04 (s, 3H), 4.89 (m, 1H), 6.74 (s, 1H), 7.36-7.43 (m, 2H), 7.56 (m, 1H), 7.82-7.88 (m, 2H), 8.30 (d, 1H), 8.45 (s, 1H), 8.76 (s, 1H). LCMS m/z = 446.2 [MH]$^+$; RT [HPLC Method D1] = 3.873 min. |

| Ex. No. | Structure | Separation Method Starting Material | Analytical Data |
|---|---|---|---|
| 66[a] | Enantiomer 2 | HPLC Method D4; 7-{1-[1-(2-Fluorophenyl)-1H-1,2,3-triazol-4-yl]propyl}-5-(4-methoxypyrimidin-5-yl)pyrrolo[2,1-f][1,2,4]triazin-4-amine (Example 83) | $^1$HNMR (400 MHz, MeOD-$d_4$): 1.03 (t, 3H), 2.33 (m, 2H), 4.05 (s, 3H), 4.89 (m, 1H), 6.78 (s, 1H), 7.36-7.43 (m, 2H), 7.56 (m, 1H), 7.85 (m, 1H), 7.91 (s, 1H), 8.32 (d, 1H), 8.45 (s, 1H), 8.77 (s, 1H). LCMS m/z = 446.2 [MH]$^+$; RT [HPLC Method D1] = 7.077 min. |
| 67 | Enantiomer 1 | HPLC Method E3; 1-{4-amino-5-[2-(trifluoromethyl)pyrimidin-5-yl]pyrrolo[2,1-f][1,2,4]triazin-7-yl}-1-[1-(2-fluorophenyl)-1H-1,2,3-triazol-4-yl]ethanol (Example 73) | $^1$HNMR (400 MHz, DMSO-$d_6$): 2.11 (s, 3H), 6.23 (s, 1H), 6.95 (s, 1H), 7.06 (s, 1H), 7.15-7.25 (br s, 2H), 7.44 (m, 1H), 7.54-7.60 (m, 2H), 7.90 (s, 1H), 8.42 (s, 1H), 9.08 (s, 2H). LCMS m/z = 486.2 [MH]$^+$; RT [HPLC Method E1] = 8.135 min. |
| 68 | Enantiomer 2 | HPLC Method E3; 1-{4-amino-5-[2-(trifluoromethyl)pyrimidin-5-yl]pyrrolo[2,1-f][1,2,4]triazin-7-yl}-1-[1-(2-fluorophenyl)-1H-1,2,3-triazol-4-yl]ethanol (Example 73) | $^1$HNMR (400 MHz, DMSO-$d_6$): 2.11 (s, 3H), 6.22 (s, 1H), 7.06 (s, 1H), 7.15-7.25 (br s, 2H), 7.44 (m, 1H), 7.52-7.58 (m, 2H), 7.80 (m, 1H), 7.90 (s, 1H), 8.42 (s, 1H), 9.08 (s, 2H). LCMS m/z = 486.1 [MH]$^+$; RT [HPLC Method E1] = 10.144 min. |

[a] additionally purified by preparative HPLC using a Gemini-C18 150*21.2 mm, 5 μm column; eluting with MeCN:H$_2$O (0.1 TFA%);

Example 69: 7-{1-[1-(2-Fluorophenyl)-1H-1,2,3-triazol-4-yl]ethyl}-5-[2-(trifluoromethyl) pyrimidin-5-yl]pyrrolo[2,1-f][1,2,4]triazin-4-amine

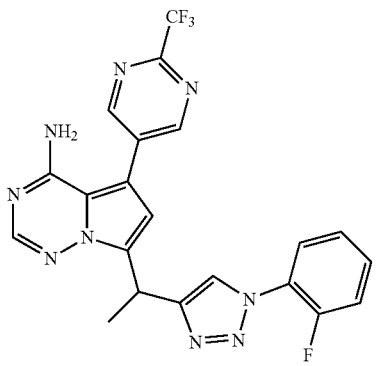

To a mixture of 5-bromo-7-{[1-(2-fluorophenyl)-1H-1,2,3-triazol-4-yl]ethyl}pyrrolo[2,1-f][1,2,4]triazin-4-amine (Preparation 2, 260 mg, 0.65 mmol) and 5-(4,4,5,5-tetramethyl-1,3,2-dioxaborolan-2-yl)-2-(trifluoromethyl)pyrimidine (266 mg, 0.97 mmol) in 1,4-dioxane (9 mL) and H$_2$O (3 mL) were added PdCl$_2$(dppf) (48 mg, 0.065 mmol) and Na$_2$CO$_3$ (138 mg, 1.3 mmol), and the reaction stirred under N2 at 95° C. for 2 hrs. The cooled mixture was concentrated under reduced pressure and the residue partitioned between H$_2$O (30 mL) and EtOAc (30 mL). The layers were separated, the aqueous phase extracted with EtOAc (30 mL×3), the combined organic extracts were dried (Na$_2$SO$_4$), filtered and the filtrate concentrated in vacuo. The residue was purified by HPLC eluting with MeCN:H$_2$O (0.1% TFA) (45:55 to 55:45), to afford the title compound as a white solid (130 mg, 42%). $^1$HNMR (400 MHz, DMSO-d$_6$): 1.77 (d, 3H), 4.97 (q, 1H), 6.90 (s, 1H), 7.15-7.25 (m, 2H), 7.48-7.62 (m, 4H), 8.05 (s, 1H), 8.45 (s, 1H), 9.05 (s, 2H). LCMS m/z=470.2 [MH]$^+$; RT [HPLC Method A]=1.658 min.

Examples 70 to 79

The following Examples were prepared from the appropriate bromide starting material and boronate ester, following an analogous procedure to that described in Example 69 and purified using silica gel column chromatography eluting with suitable solvents.

| Ex. No. | Structure | Starting Material | Analytical Data |
|---|---|---|---|
| 70$^a$ | (structure: 5-[2-(trifluoromethyl)pyrimidin-5-yl]pyrrolo[2,1-f][1,2,4]triazin-4-amine with 1-(2,4-difluorophenyl)triazolyl ethyl substituent) | 5-bromo-7-{1-[1-(2,4-difluorophenyl)-1H-1,2,3-triazol-4-yl]ethyl}pyrrolo[2,1-f][1,2,4]triazin-4-amine (Preparation 4) | LCMS m/z = 488.0 [MH]$^+$; RT [HPLC Method A] = 1.783 min. |
| 71$^{a,b}$ | (structure: analogous compound with 1-(2,5-difluorophenyl)triazolyl propyl substituent) | 5-bromo-7-{1-[1-(2,5-difluorophenyl)-1H-1,2,3-triazol-4-yl]propyl}pyrrolo[2,1-f][1,2,4]triazin-4-amine (Preparation 6) | LCMS m/z = 502.2 [MH]$^+$ |

| Ex. No. | Structure | Starting Material | Analytical Data |
|---|---|---|---|
| 72[a,b] | 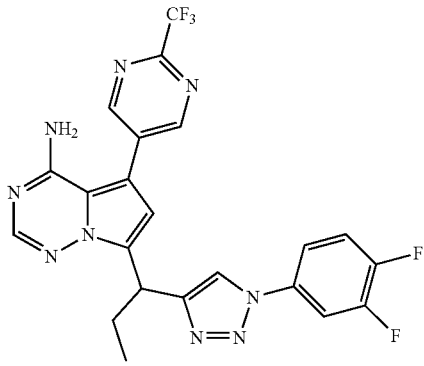 | 5-bromo-7-{1-[1-(3,4-difluorophenyl)-1H-1,2,3-triazol-4-yl]propyl}pyrrolo[2,1-f][1,2,4]triazin-4-amine (Preparation 7) | LCMS m/z = 502.2 [MH]+ |
| 73[b] | 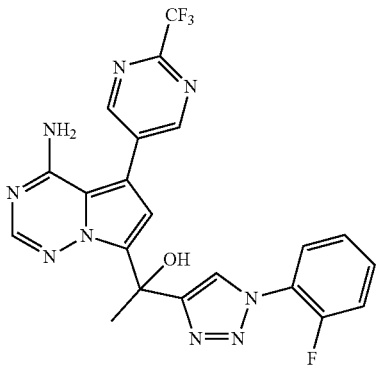 [SMILES: CC(O)(c1cn(-c2ccccc2F)nn1)c1cc(-c2cnc(C(F)(F)F)nc2)c2c(N)ncnn12] | 1-{4-amino-5-bromopyrrolo[2,1-f][1,2,4]triazin-7-yl}-1-[1-(2-fluorophenyl)-1H-1,2,3-triazol-4-yl]ethanol (Preparation 16) | LCMS m/z = 486.1 [MH]+ |
| 74[c] | 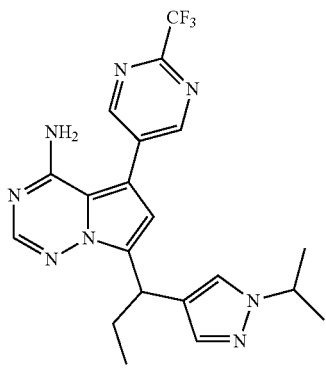 [SMILES: CCC(c1cnn(C(C)C)c1)c1cc(-c2cnc(C(F)(F)F)nc2)c2c(N)ncnn12] | 5-bromo-7-{1-[1-(propan-2-yl)-1H-pyrazol-4-yl]propyl}pyrrolo[2,1-f][1,2,4]triazin-4-amine (Preparation 8) | $^1$HNMR (400 MHz, DMSO-$d_6$): 0.85 (t, 3H), 1.35 (d, 6H), 1.92 (m, 1H), 2.04 (m, 1H), 4.39-4.47 (m, 2H), 6.87 (s, 1H), 7.13 (br s, 2H), 7.37 (s, 1H), 7.64 (s, 1H), 8.02 (s, 1H), 9.04 (s, 2H). LCMS m/z = 431.1 [MH]+; RT [HPLC Method A] = 1.781 min. |
| 75 | 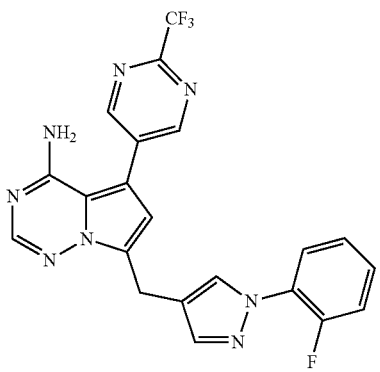 [SMILES: Nc1ncnn2c(Cc3cnn(-c4ccccc4F)c3)cc(-c3cnc(C(F)(F)F)nc3)c12] | 5-bromo-7-{[1-(2-fluorophenyl)-1H-pyrazol-4-yl]methyl}pyrrolo[2,1-f][1,2,4]triazin-4-amine (Preparation 9) | $^1$HNMR (400 MHz, DMSO-$d_6$): 4.22 (s, 2H), 6.83 (s, 1H), 7.20 (br s, 2H), 7.31-7.45 (m, 3H), 7.76 (m, 2H), 7.78 (s, 1H), 7.93 (s, 1H), 9.04 (s, 2H). LCMS m/z = 455.1 [MH]+ |

-continued

| Ex. No. | Structure | Starting Material | Analytical Data |
|---|---|---|---|
| 76[c] | 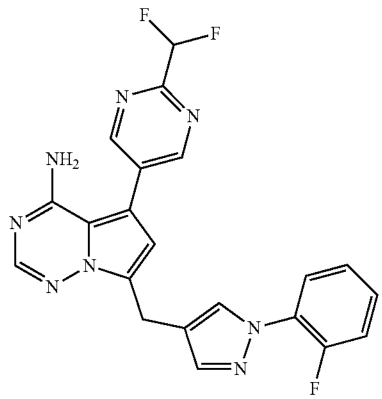 [SMILES: Nc1ncnn2c(Cc3cnn(-c4ccccc4F)c3)cc(-c3cnc(C(F)F)nc3)c12] | 5-bromo-7-{[1-(2-fluorophenyl)-1H-pyrazol-4-yl]methyl}pyrrolo[2,1-f][1,2,4]triazin-4-amine (Preparation 9) | LCMS m/z = 437.2 [MH]+ |
| 77 | 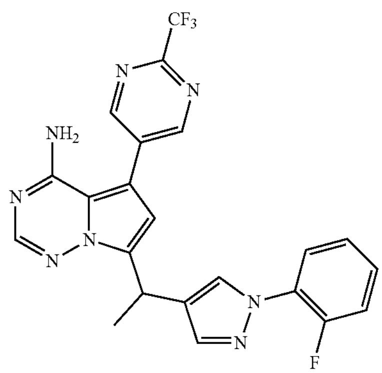 [SMILES: CC(c1cnn(-c2ccccc2F)c1)c1cc(-c2cnc(C(F)(F)F)nc2)c2c(N)ncnn12] | 5-bromo-7-{1-[1-(2-fluorophenyl)-1H-pyrazol-4-yl]ethyl}pyrrolo[2,1-f][1,2,4]triazin-4-amine (Preparation 10) | LCMS m/z = 469.1 [MH]+ |
| 78 | 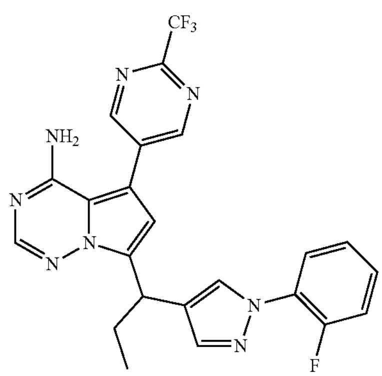 [SMILES: CCC(c1cnn(-c2ccccc2F)c1)c1cc(-c2cnc(C(F)(F)F)nc2)c2c(N)ncnn12] | 5-bromo-7-{1-[1-(2-fluorophenyl)-1H-pyrazol-4-yl]methyl}pyrrolo[2,1-f][1,2,4]triazin-4-amine (Preparation 12) | LCMS m/z = 483.1 [MH]+ |
| 79 | 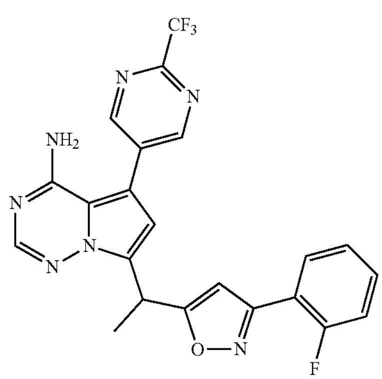 [SMILES: CC(c1cc(-c2ccccc2F)no1)c1cc(-c2cnc(C(F)(F)F)nc2)c2c(N)ncnn12] | 5-bromo-7-{1-[3-(2-fluorophenyl)-1,2-oxazol-5-yl]ethyl}pyrrolo[2,1-f][1,2,4]triazin-4-amine (Preparation 15) | LCMS m/z = 470.1 [MH]+ |

[a]purified by column chromatography on silica gel eluting with pet. ether:EtOAc, [b]DMF was used as the column solvent, instead of dioxane, [c]$K_2CO_3$ was used as the base

Example 80: 7-{[3-(2-Fluorophenyl)-1,2-oxazol-5-yl]methyl}-5-[2-(trifluoromethyl) pyrimidin-5-yl)pyrrolo[2,1-f][1,2,4]triazin-4-amine

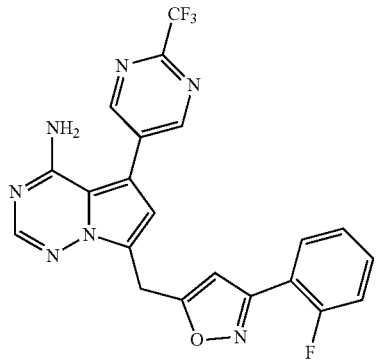 [SMILES: Nc1ncnn2c(Cc3cc(-c4ccccc4F)no3)cc(-c3cnc(C(F)(F)F)nc3)c12]

To a solution of 5-bromo-7-{[3-(2-fluorophenyl)-1,2-oxazol-5-yl]methyl}pyrrolo[2,1-f][1,2,4]triazin-4-amine (Preparation 14, 250 mg, 0.644 mmol) in 1,4-dioxane (10 mL), was slowly added 5-(4,4,5,5-tetramethyl-1,3,2-dioxaborolan-2-yl)-2-(trifluoromethyl)pyrimidine (1.3 g, 4.86 mmol), Pd(dppf)Cl$_2$ (0.26 g, 0.324 mmol) and Na$_2$CO$_3$ (0.69 g, 6.48 mmol) in H$_2$O (2 mL) and the reaction stirred at 100° C. for 16 hr under N2. The cooled mixture was concentrated in vacuo and the crude product purified by column chromatography on silica gel eluting with DCM:MeOH (91:9) to afford the title compound as a yellow solid (150 mg, 51%). LCMS m/z=456.0 [MH]$^+$

Example 81: 7-{[1-(2-Fluorophenyl)-1H-1,2,3-triazol-4-yl]methyl}-5-[2-(trifluoromethyl) pyrimidin-5-yl]pyrrolo[2,1-f][1,2,4]triazin-4-amine

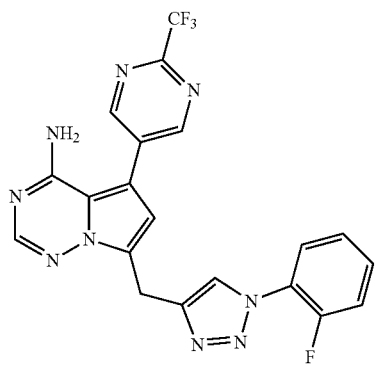 [SMILES: Nc1ncnn2c(Cc3cn(-c4ccccc4F)nn3)cc(-c3cnc(C(F)(F)F)nc3)c12]

To a solution of 5-bromo-7-{[1-(2-fluorophenyl)-1H-1,2,3-triazol-4-yl]methyl}pyrrolo[2,1-f][1,2,4]triazin-4-amine (Preparation 1, 500 mg, 1.27 mmol) in 1,4-dioxane (10 mL), was slowly added 2-(trifluoromethyl)pyrimidin-5-ylboronic acid (867 mg, 4.52 mmol), K$_2$CO$_3$ (356 mg, 2.58 mmol) in H$_2$O (5 mL) and Pd(dppf)Cl$_2$ (105 mg, 0.129 mmol) and the reaction stirred at 105° C. for 2 hrs under N2. The cooled mixture was concentrated in vacuo and the crude product purified by column chromatography on silica gel eluting with DCM:MeOH (91:9) to afford the title compound as a yellow solid (260 mg, 44%). LCMS m/z=456.1 [MH]$^+$; RT [HPLC Method A]=1.717 min.

Example 82: 7-{[1-(2-Fluorophenyl)-1H-1,2,3-triazol-4-yl]propyl}-5-[2-(trifluoromethyl)pyrimidin-5-yl]pyrrolo[2,1-f][1,2,4]triazin-4-amine

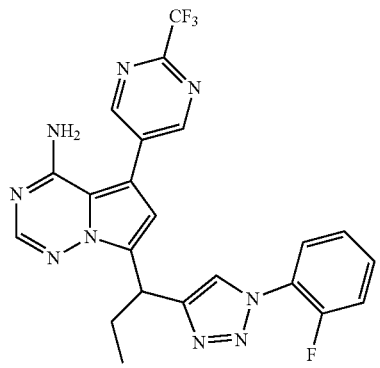 [SMILES: CCC(c1cn(-c2ccccc2F)nn1)c1cc(-c2cnc(C(F)(F)F)nc2)c2c(N)ncnn12]

The title compound was obtained as a white solid (7.5 g, 72%) from 5-bromo-7-{[1-(2-fluorophenyl)-1H-1,2,3-triazol-4-yl]propyl}pyrrolo[2,1-f][1,2,4]triazin-4-amine (Preparation 5) and 5-(4,4,5,5-tetramethyl-1,3,2-dioxaborolan-2-yl)-2-(trifluoromethyl)pyrimidine following the procedure described in Example 80. $^1$HNMR (400 MHz, DMSO-d$_6$): 0.93 (t, 3H), 2.20 (m, 2H), 4.82 (m, 1H), 6.97 (s, 1H), 7.15-7.30 (br s, 2H), 7.44 (m, 1H), 7.55 (m, 2H), 7.82 (m, 1H), 8.04 (s, 1H), 8.50 (s, 1H), 9.05 (s, 2H). LCMS m/z=484.1 [MH]$^+$; RT [HPLC Method A]=1.743 min.

Example 83: 7-{[1-(2-Fluorophenyl)-1H-1,2,3-triazol-4-yl]propyl}-5-(4-methoxypyrimidin-5-yl)pyrrolo[2,1-f][1,2,4]triazin-4-amine

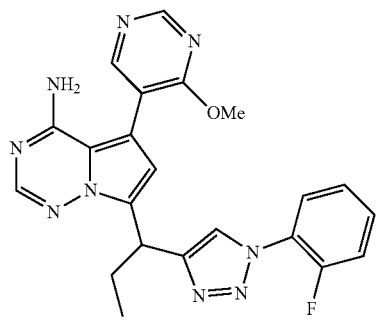 [SMILES: CCC(c1cn(-c2ccccc2F)nn1)c1cc(-c2cncnc2OC)c2c(N)ncnn12]

The title compound was obtained as a yellow solid (160 mg, 50%) from 5-bromo-7-{1-[1-(2-fluorophenyl)-1H-1,2,3-triazol-4-yl]propyl}pyrrolo[2,1-f][1,2,4]triazin-4-amine (Preparation 5) and 4-methoxypyrimidin-5-ylboronic acid, following the procedure described in Example 81. $^1$HNMR (400 MHz, MeOD-d$_4$): 1.05 (t, 3H), 2.35 (m, 2H), 4.08 (s, 3H), 4.91 (q, 1H), 7.00 (s, 1H), 7.38-7.45 (m, 2H), 7.60 (m, 1H), 7.82 (m, 1H), 8.09 (s, 1H), 8.40 (d, 1H), 8.58 (s, 1H), 8.87 (s, 1H). RT [HPLC Method A]=1.288 min.

Example 84: 7-{[1-(2,4-Difluorophenyl)-1H-1,2,3-triazol-4-yl]propyl}-5-[2-(trifluoromethyl)pyrimidin-5-yl]pyrrolo[2,1-f][1,2,4]triazin-4-amine

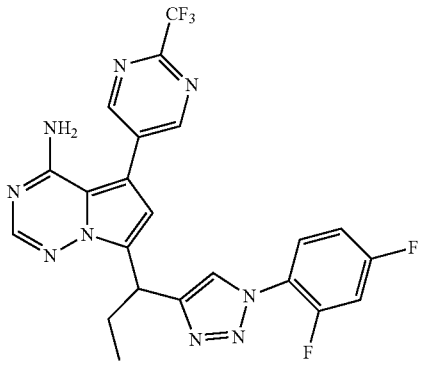 [SMILES: CCC(c1cn(-c2ccc(F)cc2F)nn1)c1cc(-c2cnc(C(F)(F)F)nc2)c2c(N)ncnn12]

To a suspension of 5-bromo-7-{[1-(2,4-difluorophenyl)-1H-1,2,3-triazol-4-yl]propyl}pyrrolo[2,1-f][1,2,4]triazin-4-amine (Preparation 13, 250 mg, 0.58 mmol), 5-(4,4,5,5-tetramethyl-1,3,2-dioxaborolan-2-yl)-2-(trifluoromethyl)pyrimidine (238 mg, 0.87 mmol) and $Na_2CO_3$ (123 mg, 1.16 mmol) in $DMF:H_2O$ (12 mL:3 mL) was added $Pd(PPh_3)_4$ (70 mg, 0.06 mmol) under N2 and the reaction was stirred at 100° C. for 12 hr. The cooled mixture was poured into ice-water (10 mL) and extracted with EtOAc (3×10 mL). The combined organic layers were washed with brine (3×10 mL), dried and evaporated under reduced pressure. The residue was purified by column chromatography on silica gel eluting with EtOAc:pet. ether (0:100 to 80:20) to afford the title compound as an off-white solid (100 mg, 35%). LCMS m/z=502.2 [MH]+; RT [HPLC Method A]=1.718 min.

Example 85: 7-{1-[1-(2,4-Difluorophenyl)-1H-pyrazol-4-yl]ethyl}-5-[2-(trifluoromethyl)pyrimidin-5-yl]pyrrolo[2,1-f][1,2,4]triazin-4-amine

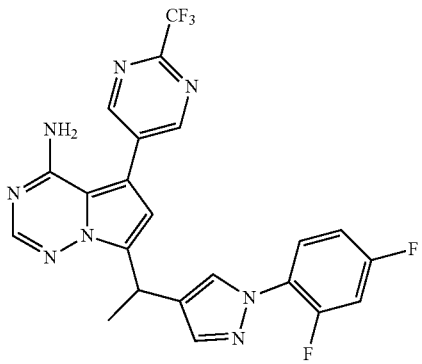 [SMILES: CC(c1cnn(-c2ccc(F)cc2F)c1)c1cc(-c2cnc(C(F)(F)F)nc2)c2c(N)ncnn12]

The title compound was obtained as a light yellow solid (0.5 g, 43%) from 5-bromo-7-{1-[1-(2,4-difluorophenyl)-1H-pyrazol-4-yl]ethyl}pyrrolo[2,1-f][1,2,4]triazin-4-amine (Preparation 11) and 5-(4,4,5,5-tetramethyl-1,3,2-dioxaborolan-2-yl)-2-(trifluoromethyl)pyrimidine following the procedure described in Example 84, except dioxane/$H_2O$ was used as the reaction solvent. LCMS m/z=487.1 [MH]+; RT [HPLC Method A]=1.867 min.

Example 86: 7-{1-[1-(2,4-Difluorophenyl)-1H-pyrazol-4-yl]propyl}-5-[2-(trifluoromethyl)pyrimidin-5-yl]pyrrolo[2,1-f][1,2,4]triazin-4-amine

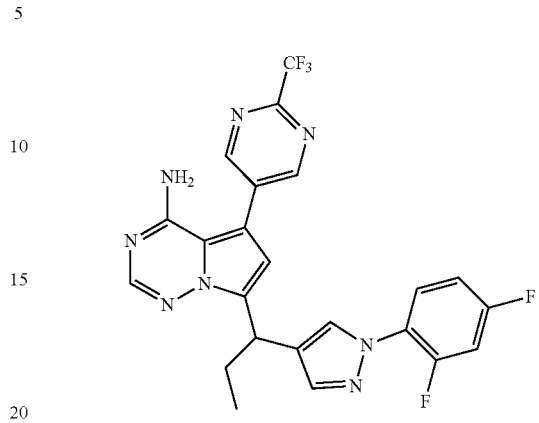

The title compound was obtained as a light yellow solid (1.5 g, 5%) from 5-bromo-7-{1-[1-(2,4-difluorophenyl)-1H-pyrazol-4-yl]propyl}pyrrolo[2,1-f][1,2,4]triazin-4-amine (Preparation 13) and 5-(4,4,5,5-tetramethyl-1,3,2-dioxaborolan-2-yl)-2-(trifluoromethyl)pyrimidine following the procedure described in Preparation 84, except dioxane/$H_2O$ was used as the reaction solvent. LCMS m/z=501.1 [MH]+; RT [HPLC Method A]=1.912 min.

Examples 87 and 88: -{1-[1-(2-Fluorophenyl)-1H-pyrazol-4-yl]propyl}-3-[2-(trifluoromethyl)pyrimidin-5-yl]-1H-pyrazolo[3,4-d]pyrimidin-4-amine, Enantiomer 1 and 2

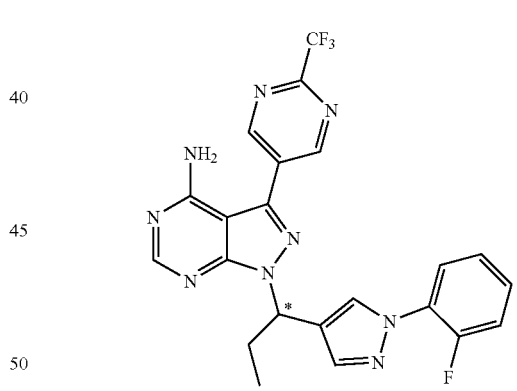

1-{1-[1-(2-Fluorophenyl)-1H-pyrazol-4-yl]propyl}-3-[2-(trifluoromethyl)pyrimidin-5-yl]-1H-pyrazolo[3,4-d]pyrimidin-4-amine (Example 91, 0.17 g) was purified using HPLC Method E5, to afford Example 87, enantiomer 1 (52.7 mg). $^1$HNMR (400 MHz, DMSO-$d_6$): 0.81 (t, 3H), 2.24-2.30 (m, 1H), 2.41-2.50 (m, 1H), 6.01 (m, 1H), 7.31-7.43 (m, 5H), 7.73 (m, 1H), 7.89 (s, 1H), 8.28 (s, 1H), 8.35 (s, 1H), 9.29 (s, 2H). LCMS m/z=484.2 [MH]+; RT [HPLC Method C14]=4.799 min.

Further elution provided Example 88, enantiomer 2 (47.6 mg). $^1$HNMR (400 MHz, DMSO-$d_6$): 0.81 (t, 3H), 2.24-2.30 (m, 1H), 2.41-2.50 (m, 1H), 6.01 (m, 1H), 7.31-7.43 (m, 5H), 7.73 (m, 1H), 7.89 (s, 1H), 8.28 (s, 1H), 8.35 (s, 1H), 9.29 (s, 2H). LCMS m/z=484.2 [MH]+; RT [HPLC Method $C_{14}$]=6.068 min.

Examples 89 and 90: 1-{1-[1-(2-Fluorophenyl)-1H-1,2,3-triazol-4-yl]propyl}-3-[2-(trifluoromethyl)pyrimidin-5-yl]-1H-pyrazolo[3,4-d]pyrimidin-4-amine, Enantiomer 1 and 2

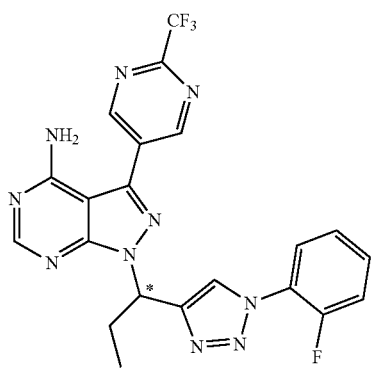 [SMILES: CCC(c1cn(-c2ccccc2F)nn1)n1nc(-c2cnc(C(F)(F)F)nc2)c2c(N)ncnc21]

1-{1-[1-(2-fluorophenyl)-1H-1,2,3-triazol-4-yl]propyl}-3-[2-(trifluoromethyl)pyrimidin-5-yl]-1H-pyrazolo[3,4-d]pyrimidin-4-amine (Example 92, 1.6 g) was purified using HPLC Method C23A to afford Example 89, enantiomer 1 (504 mg). $^1$HNMR (400 MHz, DMSO-d$_6$): 0.85 (t, 3H), 2.43-2.50 (m, 2H), 6.19 (m, 1H), 7.35-7.45 (m, 3H), 7.55-7.65 (m, 2H), 7.80 (m, 1H), 8.36 (s, 1H), 8.66 (s, 1H), 9.28 (s, 2H). LCMS m/z=485.1 [MH]$^+$; RT [HPLC Method C5]=2.437 min.

Further elution provided Example 90, enantiomer 2 (508 mg). $^1$HNMR (400 MHz, DMSO-d$_6$): 0.85 (t, 3H), 2.43-2.50 (m, 2H), 6.19 (m, 1H), 7.35-7.45 (m, 3H), 7.55-7.65 (m, 2H), 7.80 (m, 1H), 8.36 (s, 1H), 8.66 (s, 1H), 9.28 (s, 2H). LCMS m/z=485.1 [MH]$^+$; RT [HPLC Method C5]=3.489 min.

Example 91: 1-{1-[1-(2-Fluorophenyl)-1H-pyrazol-4-yl]propyl}-3-[2-(trifluoromethyl)pyrimidin-5-yl]-1H-pyrazolo[3,4-d]pyrimidin-4-amine

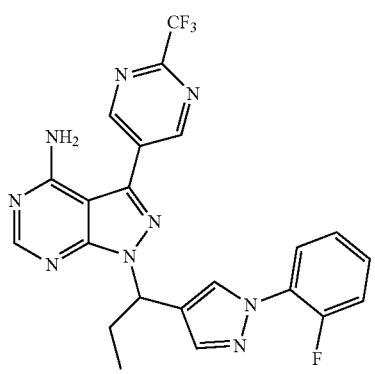 [SMILES: CCC(c1cnn(-c2ccccc2F)c1)n1nc(-c2cnc(C(F)(F)F)nc2)c2c(N)ncnc21]

To a solution of 1-{1-[1-(2-fluorophenyl)-1H-pyrazol-4-yl]propyl}-3-iodo-1H-pyrazolo[3,4-d]pyrimidin-4-amine (Preparation 58, 0.3 g, 0.45 mmol) in DMF (25 mL) was added 5-(4,4,5,5-tetramethyl-1,3,2-dioxaborolan-2-yl)-2-(trifluoromethyl)pyrimidine (355 mg, 0.90 mmol) and Na$_2$CO$_3$ solution (7 mL). Pd(PPh$_3$)$_4$ (52 mg, 0.045 mmol) was added and the reaction stirred at 100° C. for 18 hrs. The cooled mixture was partitioned between EtOAc and water and the layers separated. The organic layer was washed with brine, dried and evaporated in vacuo. The crude product was purified by column chromatography on silica gel eluting with DCM:MeOH (95:5) to afford the title compound (170 mg, 78%). LCMS m/z=484.1 [MH]$^+$

Example 92: 1-{[1-(2-Fluorophenyl)-1H-1,2,3-triazol-4-yl]propyl}-3-[2-(trifluoromethyl)pyrimidin-5-yl]-1H-pyrazolo[3,4-d]pyrimidin-4-amine

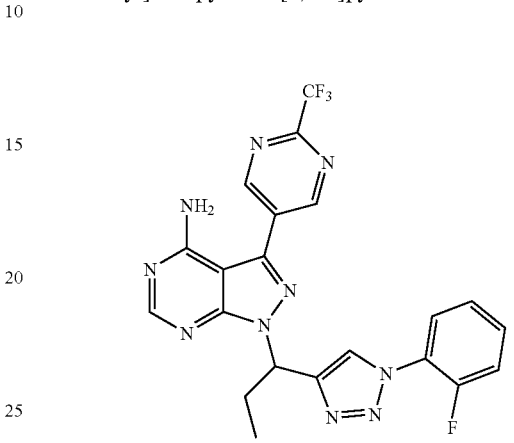

A stirred solution of 1-{[1-(2-fluorophenyl)-1H-1,2,3-triazol-4-yl]propyl}-3-iodo-1H-pyrazolo[3,4-d]pyrimidin-4-amine (Preparation 59, 3 g, 6.46 mmol) in dioxan/H$_2$O (100 mL/25 mL) was added 2-(trifluoromethyl)pyrimidin-5-ylboronic acid (1.86 g, 9.69 mmol), K$_2$CO$_3$ (2.67 g, 19.38 mmol) and Pd(dppf)Cl$_2$ (236 mg, 0.323 mmol) under N2 and the reaction stirred at 90° C. for 2 hrs. The cooled mixture was filtered, the filtrate concentrated under reduced pressure and the residue diluted with water and extracted with EtOAc (3×100 mL). The combined organic extracts were concentrated in vacuo and purified by prep HPLC to give the title compound as a yellow solid (1.6 g, 51%). $^1$HNMR (400 MHz, DMSO-d$_6$): 0.85 (t, 3H), 2.44 (m, 2H), 6.18 (m, 1H), 7.40 (m, 3H), 7.59 (m, 2H), 7.77 (m, 1H), 8.35 (s, 1H), 8.65 9s, 1H), 9.27 (s, 2H). LCMS m/z=484.7 [MH]$^+$

Example 93: 5-(4-Chlorophenyl)-7-{[1-(2-fluorophenyl)-1H-1,2,3-triazol-4-yl]methyl}imidazo[5,1-f][1,2,4]triazin-4-amine trifluoroacetate

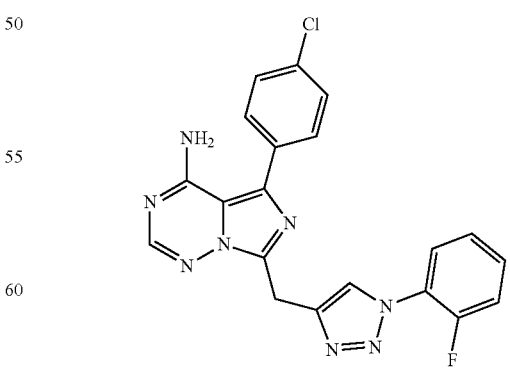

To a solution of triazole (62.2 mg, 0.90 mmol) in MeCN (5 mL) at 0° C. was added POCl$_3$ (0.033 mL, 0.36 mmol). Et$_3$N (0.126 mL, 0.90 mmol) was added drop wise over 20 min, the solution allowed to warm to rt and stirred for 30 min. 5-(4-Chlorophenyl)-7-{[1-(2-fluorophenyl)-1H-1,2,3-triazol-4-yl]methyl}imidazo[5,1-f][1,2,4]triazin-4-ol (Preparation 63, 38 mg, 0.09 mmol) was added portion wise, the solution diluted with DCM (2 mL), then stirred at 70° C. for 18 hrs. 0.5 M NH$_3$ in dioxane (7 mL) and NH$_4$OH (1 mL) were added and the reaction stirred under microwave irradiation for 1 hr at 120° C. The mixture was cooled, the resulting precipitate filtered off and the filtrate evaporated under reduced pressure. The residue was purified by using HPLC Method G1 to afford the title compound as a solid (12.1 mg, 32%). LCMS m/z=421.2 [MH]$^+$ The following examples were prepared by analogy with the routes previously described.

Example 94

1-[1-(1-phenyl-1H-1,2,3-triazol-4-yl)propyl]-3-[2-(trifluoromethyl)pyrimidin-5-yl]-1H-pyrazolo[3,4-d]pyrimidin-4-amine, enantiomer 1; Separated using HPLC Method C30; $^1$HNMR (400 MHz, CDCl$_3$): 0.98 (t, 3H), 2.50-2.63 (m, 2H), 5.82 (br s, 2H), 6.33 (m, 1H), 7.45-7.52 (m, 3H), 7.69 (m, 2H), 8.08 (s, 1H), 8.50 (s, 1H), 9.28 (s, 2H). LCMS m/z=467.1 [MH]$^+$; RT [HPLC Method C10]=3.125 min.

Example 95

1-[1-(1-phenyl-1H-1,2,3-triazol-4-yl)propyl]-3-[2-(trifluoromethyl)pyrimidin-5-yl]-1H-pyrazolo[3,4-d]pyrimidin-4-amine, enantiomer 2; Separated using HPLC Method C30; $^1$HNMR (400 MHz, MeOD-d$_4$): 0.95 (t, 3H), 2.51-2.67 (m, 2H), 6.27 (m, 1H), 7.48 (m, 2H), 7.52 (m, 3H), 8.39 (s, 1H), 8.66 (s, 1H), 9.31 (s, 2H). LCMS m/z=467.2 [MH]$^+$; RT [HPLC Method C10]=2.244 min.

Example 96

4-amino-5-(2-(difluoromethyl)pyrimidin-5-yl)-7-(1-(1-(2-fluorophenyl)-1H-pyrazol-4-yl)ethyl)pyrrolo[1,2-f][1,2,4]triazine-6-carbonitrile, enantiomer 1; Separated using SFC Method F1; $^1$HNMR (400 MHz, DMSO-d$_6$): 1.82 (d, 3H), 5.02 (q, 1H), 7.07 (t, 1H), 7.31-7.48 (m, 3H), 7.73-7.77 (m, 2H), 8.15-8.16 (m, 2H), 9.05 (s, 2H); LCMS m/z=476.2 [MH]$^+$; RT [SFC Method F2]=6.049 min.

Example 97

4-amino-5-(2-(difluoromethyl)pyrimidin-5-yl)-7-(1-(1-(2-fluorophenyl)-1H-pyrazol-4-yl)ethyl)pyrrolo[1,2-f][1,2,4]triazine-6-carbonitrile, enantiomer 2; Separated using SFC Method F1; $^1$HNMR (400 MHz, DMSO-d$_6$): 1.82 (d, 3H), 5.02 (q, 1H), 7.07 (t, 1H), 7.31-7.48 (m, 3H), 7.73-7.77 (m, 2H), 8.15-8.16 (m, 2H), 9.05 (s, 2H); LCMS m/z=476.2 [MH]$^+$; RT [SFC Method F2]=6.599 min.

Example 98

7-(1-(1-(2,5-difluorophenyl)-1H-1,2,3-triazol-4-yl)ethyl)-5-(2-(trifluoromethyl)pyrimidin-5-yl)pyrrolo[1,2-f][1,2,4]triazin-4-amine, enantiomer 1; Separated using HPLC Method C24A; $^1$HNMR (400 MHz, DMSO-d$_6$): 1.55 (d, 3H), 4.76 (q, 1H), 6.68 (s, 1H), 7.04 (br s, 2H), 7.26 (m, 1H), 7.42 (m, 1H), 7.59 (m, 1H), 7.83 (s, 1H), 8.27 (d, 1H), 8.83 (s, 2H); LCMS m/z=488.0 [MH]$^+$; RT [HPLC Method C1]=4.359 min.

Example 99

1-(1-(1-(2,4-difluorophenyl)-1H-1,2,3-triazol-4-yl)propyl)-3-(2-(trifluoromethyl)pyrimidin-5-yl)-1H-pyrazolo[3,4-d]pyrimidin-4-amine, enantiomer 1; Separated using HPLC Method B2; $^1$HNMR (400 MHz, DMSO-d$_6$): 0.85 (t, 3H), 2.45 (m, 2H), 6.18 (m, 1H), 7.34 (m, 1H), 7.48 (br s, 2H), 7.68 (m, 1H), 7.87 (m, 1H), 8.36 (s, 1H), 8.65 (s, 1H), 9.28 (s, 2H); LCMS m/z=503.2 [MH]$^+$; RT [HPLC Method C10]=3.734 min.

Ussinq Chamber Electrophysiology Assay of CFTR Potentiation in CF Bronchial Epithelial Cells Primary cystic fibrosis human bronchial epithelial (CF hBE) cells were expanded and cultured according to published methods (Neuberger et al., Ch. 4 of Cystic Fibrosis, Methods in Molecular Biology vol. 741, pp. 39-54 (2011)). Well-differentiated cells (>30 days at air/liquid interface) on Snapwell filters (Corning Costar, cat. no. 3801) were mounted in Ussing chambers (Physiologic Instruments, Inc., San Diego, Calif.). F508del/F508del cultures were assayed at 27° C. and G551D/F508del cells were assayed at 35° C. HEPES buffered physiological saline (composition (in mM): 137 NaCl, 4 KCl, 1 MgCl2, 1.8 CaCl2), 10 HEPES Na) was used in both apical and basolateral chambers. Chambers were bubbled with air to promote mixing and the voltage was clamped to zero. Amiloride (30 uM), forskolin (10 uM), test compound (4 increasing concentrations), and CFTRinh-172 (20 uM) were added sequentially with 20-25 minutes between additions. Short-circuit currents were acquired and analyzed using LabScribe2. Test compound responses were scaled relative to responses for DMSO (0%) and the maximal response of a positive control potentiator (100%).

FRT Ion Flux Assay of F508del CFTR Potentiation

Fischer rat thyroid (FRT) cell lines stably expressing recombinant F508del V470 CFTR and halide-sensitive yellow fluorescent protein (Pedemonte et al., J. Clin. Invest. 115(9) 2564-71 (2005)) were seeded at 25,000 cells/well in 50 uL/well of culture medium into black-walled, clear bottom tissue-culture-treated 384-well plates (Corning, cat. no. 3712). After one day, the cells were pre-incubated at 27° C./5% CO$_2$ for 16-24 hours. The cells were then washed with dPBS and treated with forskolin (20 uM) and test compound for 30 min by addition of 20 uL of compound dilution buffer (dPBS containing forskolin and test compound). Plates were loaded into FLIPR384 fluorescence imaging plate reader (Molecular Devices). After an initial fluorescence reading, iodide buffer (25 uL) (composition (in mM): 137 NaI, 1.5 K$_2$PO$_4$, 8.1 NaH$_2$PO$_4$, 2.7 KCl, 0.5 MgCl$_2$, 1 CaCl$_2$)) was added and a second fluorescence reading was made after approximately 21 seconds. Data treatment involved division of the second fluorescence reading by the initial fluorescence reading, then scaling of the resulting normalized endpoint fluorescence with respect to the responses for DMSO (0%) and a positive control potentiator (100%).

| Example Number | Compound Name | CF hBE EC$_{50}$ (nM) | FRT EC$_{50}$ (nM) |
|---|---|---|---|
| 1 | 4-amino-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile, enantiomer 1 | 51.09 | 46.78 |

-continued

| Example Number | Compound Name | CF hBE EC$_{50}$ (nM) | FRT EC$_{50}$ (nM) |
|---|---|---|---|
| 2 | 4-amino-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile, enantiomer 2 | 11.20 | 9.14 |
| 3 | 4-amino-7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile, enantiomer 1 | 14.57 | 10.60 |
| 4 | 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 1 | 20.52 | 35.76 |
| 5 | 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 2 | 3.02 | 2.13 |
| 6 | 4-amino-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 1 | 5.48 | 5.05 |
| 7 | 4-amino-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 2 | 33.47 | 45.17 |
| 8 | 4-amino-7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 2 | 12.96 | 17.21 |
| 9 | 4-amino-7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile, enantiomer 2 | 28.37 | 41.22 |
| 10 | 4-amino-7-{1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile, enantiomer 1 | 48.00 | 95.87 |
| 11 | 4-amino-7-{1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile, enantiomer 2 | 6.96 | 4.17 |
| 12 | 4-amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile, enantiomer 1 | 4.00 | 12.52 |
| 13 | 4-amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile, enantiomer 2 | 0.42 | 0.62 |
| 14 | 4-amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile, enantiomer 1 | 2.00 | 6.59 |
| 15 | 4-amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile, enantiomer 2 | 0.20 | 0.56 |
| 16 | 4-amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile, enantiomer 1 | 0.42 | 0.56 |
| 17 | 4-amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile, enantiomer 2 | 3.00 | 13.35 |
| 18 | 4-amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile, enantiomer 1 | 1.67 | 3.10 |
| 19 | 4-amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile, enantiomer 2 | 5.00 | 13.85 |
| 20 | 4-amino-7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazine-6-carbonitrile, enantiomer 1 | 8.94 | 30.02 |

-continued

| Example Number | Compound Name | CF hBE EC$_{50}$ (nM) | FRT EC$_{50}$ (nM) |
|---|---|---|---|
| 21 | 4-amino-7-{(1R)-1-[1-(2,4-difluorophenyl)-1H-pyrazol-4-yl]ethyl}-5-[2-(trifluoromethyl)pyrimidin-5-yl]pyrrolo[2,1-f][1,2,4]triazine-6-carbonitrile, enantiomer 2 | 0.66 | 3.13 |
| 22 | 4-amino-7-{[1-(2-fluorophenyl)-1H-1,2,3-triazol-4-yl]methyl}-5-[2-(trifluoromethyl)pyrimidin-5-yl]pyrrolo[2,1-f][1,2,4]triazine-6-carbonitrile | 27.09 | 23.30 |
| 23 | 4-amino-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile | N.D. | N.D. |
| 24 | 4-amino-7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazine-6-carbonitrile | 20.90 | 28.68 |
| 25 | 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile | 7.86 | N.D. |
| 26 | 4-amino-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazine-6-carbonitrile | N.D. | N.D. |
| 27 | 4-amino-7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile | N.D. | N.D. |
| 28 | 4-amino-7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazine-6-carbonitrile | N.D. | N.D. |
| 29 | 4-amino-7-{1-[1-(propan-2-yl)-1H-pyrazol-4-yl]propyl}-5-[2-(trifluoromethyl)pyrimidin-5-yl]pyrrolo[2,1-f][1,2,4]triazine-6-carbonitrile | N.D. | N.D. |
| 30 | 4-amino-7-{[1-(2-fluorophenyl)-1H-pyrazol-4-yl]methyl}-5-[2-(trifluoromethyl)pyrimidin-5-yl]pyrrolo[2,1-f][1,2,4]triazine-6-carbonitrile | 0.86 | 0.57 |
| 31 | 4-amino-5-[2-(difluoromethyl)pyrimidin-5-yl]-7-{[1-(2-fluorophenyl)-1H-pyrazol-4-yl]methyl}pyrrolo[2,1-f][1,2,4]triazine-6-carbonitrile | 1.05 | 0.41 |
| 32 | 4-amino-7-{1-[1-(2-fluorophenyl)-1H-pyrazol-4-yl]ethyl}-5-[2-(trifluoromethyl)pyrimidin-5-yl]pyrrolo[2,1-f][1,2,4]triazine-6-carbonitrile | N.D. | N.D. |
| 33 | 4-amino-7-{1-[1-(2-fluorophenyl)-1H-pyrazol-4-yl]propyl}-5-[2-(trifluoromethyl)pyrimidin-5-yl]pyrrolo[2,1-f][1,2,4]triazine-6-carbonitrile | N.D. | N.D. |
| 34 | 4-amino-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazine-6-carbonitrile | N.D. | N.D. |
| 35 | 4-amino-7-{[3-(2-fluorophenyl)-1,2-oxazol-5-yl]methyl}-5-[2-(trifluoromethyl)pyrimidin-5-yl]pyrrolo[2,1-f][1,2,4]triazine-6-carbonitrile | 4.00 | 4.65 |
| 36 | 4-amino-7-{1-[3-(2-fluorophenyl)-1,2-oxazol-5-yl]ethyl}-5-[2-(trifluoromethyl)pyrimidin-5-yl]pyrrolo[2,1-f][1,2,4]triazine-6-carbonitrile | N.D. | N.D. |
| 37 | 6-bromo-7-{[1-(2-fluorophenyl)-1H-1,2,3-triazol-4-yl]methyl}-5-[2-(trifluoromethyl)pyrimidin-5-yl]pyrrolo[2,1-f][1,2,4]triazin-4-amine | N.D. | N.D. |
| 38 | 6-bromo-7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine | N.D. | N.D. |
| 39 | 6-bromo-7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine | N.D. | N.D. |
| 40 | 6-bromo-7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 41 | 6-bromo-7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 42 | 6-bromo-7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 43 | 6-bromo-7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 44 | 6-bromo-7-{[1-(2-fluorophenyl)-1H-pyrazol-4-yl]methyl}-5-[2-(trifluoromethyl)pyrimidin-5-yl]pyrrolo[2,1-f][1,2,4]triazin-4-amine | N.D. | N.D. |

-continued

| Example Number | Compound Name | CF hBE EC$_{50}$ (nM) | FRT EC$_{50}$ (nM) |
|---|---|---|---|
| 45 | 6-bromo-5-[2-(difluoromethyl)pyrimidin-5-yl]-7-{[1-(2-fluorophenyl)-1H-pyrazol-4-yl]methyl}pyrrolo[2,1-f][1,2,4]triazin-4-amine | N.D. | N.D. |
| 46 | 6-bromo-7-{1-[1-(2-fluorophenyl)-1H-pyrazol-4-yl]ethyl}-5-[2-(trifluoromethyl)pyrimidin-5-yl]pyrrolo[2,1-f][1,2,4]triazin-4-amine | N.D. | N.D. |
| 47 | 6-bromo-7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazin-4-amine | N.D. | N.D. |
| 48 | 6-bromo-7-{1-[1-(2-fluorophenyl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 49 | 6-bromo-7-{1-[1-(2,4-difluorophenyl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 50 | 6-bromo-7-{1-[1-(propan-2-yl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 51 | 6-bromo-7-{[3-(2-fluorophenyl)-1,2-oxazol-5-yl]methyl}-5-[2-(trifluoromethyl)pyrimidin-5-yl]pyrrolo[2,1-f][1,2,4]triazin-4-amine | N.D. | N.D. |
| 52 | 6-bromo-7-{1-[3-(2-fluorophenyl)-1,2-oxazol-5-yl]ethyl}-5-[2-(trifluoromethyl)pyrimidin-5-yl]pyrrolo[2,1-f][1,2,4]triazin-4-amine | N.D. | N.D. |
| 53 | 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine, enantiomer 1 | 171.00 | 76.40 |
| 54 | 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine, enantiomer 2 | 6.48 | 7.40 |
| 55 | 7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine, enantiomer 1 | 225.22 | 266.27 |
| 56 | 7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine, enantiomer 2 | 7.48 | 8.76 |
| 57 | 7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 1 | 2.00 | 1.88 |
| 58 | 7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 2 | 36.65 | 91.23 |
| 59 | 7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 1 | 114.71 | 249.27 |
| 60 | 7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 2 | 2.00 | 3.36 |
| 61 | 7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 1 | 73.67 | 253.12 |
| 62 | 7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 2 | 9.95 | 17.64 |
| 63 | 7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 1 | 19.34 | 29.55 |
| 64 | 7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine, enantiomer 2 | 177.00 | 478.84 |

-continued

| Example Number | Compound Name | CF hBE EC$_{50}$ (nM) | FRT EC$_{50}$ (nM) |
|---|---|---|---|
| 65 | 7-{1-[1-(2-fluorophenyl)-1H-1,2,3-triazol-4-yl]propyl}-5-(4-methoxypyrimidin-5-yl)pyrrolo[2,1-f][1,2,4]triazin-4-amine, enantiomer 1 | 10.38 | 13.96 |
| 66 | 7-{1-[1-(2-fluorophenyl)-1H-1,2,3-triazol-4-yl]propyl}-5-(4-methoxypyrimidin-5-yl)pyrrolo[2,1-f][1,2,4]triazin-4-amine, enantiomer 2 | 123.00 | 523.73 |
| 67 | 1-{4-amino-5-[2-(trifluoromethyl)pyrimidin-5-yl]pyrrolo[2,1-f][1,2,4]triazin-7-yl}-1-[1-(2-fluorophenyl)-1H-1,2,3-triazol-4-yl]ethanol, enantiomer 1 | 147.00 | 50.51 |
| 68 | 1-{4-amino-5-[2-(trifluoromethyl)pyrimidin-5-yl]pyrrolo[2,1-f][1,2,4]triazin-7-yl}-1-[1-(2-fluorophenyl)-1H-1,2,3-triazol-4-yl]ethanol, enantiomer 2 | N.D. | 2308.17 |
| 69 | 7-{1-[1-(2-fluorophenyl)-1H-1,2,3-triazol-4-yl]ethyl}-5-[2-(trifluoromethyl)pyrimidin-5-yl]pyrrolo[2,1-f][1,2,4]triazin-4-amine | N.D. | N.D. |
| 70 | 7-{1-[1-(2,4-difluorophenyl)-1H-1,2,3-triazol-4-yl]ethyl}-5-[2-(trifluoromethyl)pyrimidin-5-yl]pyrrolo[2,1-f][1,2,4]triazin-4-amine | N.D. | N.D. |
| 71 | 7-{1-[1-(2,5-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 72 | 7-{1-[1-(3,4-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 73 | 1-{4-amino-5-[2-(trifluoromethyl)pyrimidin-5-yl]pyrrolo[2,1-f][1,2,4]triazin-7-yl}-1-[1-(2-fluorophenyl)-1H-1,2,3-triazol-4-yl]ethanol | N.D. | N.D. |
| 74 | 7-{1-[1-(propan-2-yl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 75 | 7-{[1-(2-fluorophenyl)-1H-pyrazol-4-yl]methyl}-5-[2-(trifluoromethyl)pyrimidin-5-yl]pyrrolo[2,1-f][1,2,4]triazin-4-amine | N.D. | N.D. |
| 76 | 5-[2-(difluoromethyl)pyrimidin-5-yl]-7-{[1-(2-fluorophenyl)-1H-pyrazol-4-yl]methyl}pyrrolo[2,1-f][1,2,4]triazin-4-amine | N.D. | N.D. |
| 77 | 7-{1-[1-(2-fluorophenyl)-1H-pyrazol-4-yl]ethyl}-5-[2-(trifluoromethyl)pyrimidin-5-yl]pyrrolo[2,1-f][1,2,4]triazin-4-amine | N.D. | N.D. |
| 78 | 7-{1-[1-(2-fluorophenyl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 79 | 7-{1-[3-(2-fluorophenyl)-1,2-oxazol-5-yl]ethyl}-5-[2-(trifluoromethyl)pyrimidin-5-yl]pyrrolo[2,1-f][1,2,4]triazin-4-amine | N.D. | N.D. |
| 80 | 7-{[3-(2-fluorophenyl)-1,2-oxazol-5-yl]methyl}-5-[2-(trifluoromethyl)pyrimidin-5-yl]pyrrolo[2,1-f][1,2,4]triazin-4-amine | N.D. | N.D. |
| 81 | 7-{[1-(2-fluorophenyl)-1H-1,2,3-triazol-4-yl]methyl}-5-[2-(trifluoromethyl)pyrimidin-5-yl]pyrrolo[2,1-f][1,2,4]triazin-4-amine | N.D. | N.D. |
| 82 | 7-{1-[1-(2-fluorophenyl)-1H-1,2,3-triazol-4-yl]propyl}-5-[2-(trifluoromethyl)pyrimidin-5-yl]pyrrolo[2,1-f][1,2,4]triazin-4-amine | 4.93 | 5.83 |
| 83 | 7-{1-[1-(2-fluorophenyl)-1H-1,2,3-triazol-4-yl]propyl}-5-(4-methoxypyrimidin-5-yl)pyrrolo[2,1-f][1,2,4]triazin-4-amine | 16.00 | 18.36 |
| 84 | 7-{1-[1-(2,4-difluorophenyl)-1H-1,2,3-triazol-4-yl]propyl}-5-[2-(trifluoromethyl)pyrimidin-5-yl]pyrrolo[2,1-f][1,2,4]triazin-4-amine | N.D. | N.D. |
| 85 | 7-{1-[1-(2,4-difluorophenyl)-1H-pyrazol-4-yl]ethyl}-5-[2-(trifluoromethyl)pyrimidin-5-yl]pyrrolo[2,1-f][1,2,4]triazin-4-amine | N.D. | N.D. |
| 86 | 7-{1-[1-(2,4-difluorophenyl)-1H-pyrazol-4-yl]propyl}-5-[2-(trifluoromethyl)pyrimidin-5-yl]pyrrolo[2,1-f][1,2,4]triazin-4-amine | N.D. | N.D. |
| 87 | 1-{1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine, enantiomer 1 | 1.53 | 4.76 |

-continued

| Example Number | Compound Name | CF hBE EC$_{50}$ (nM) | FRT EC$_{50}$ (nM) |
|---|---|---|---|
| 88 | 1-{1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine, enantiomer 2 | 30.98 | 78.82 |
| 89 | 1-{1-[1-(2-fluorophenyl)-1H-1,2,3-triazol-4-yl]propyl}-3-[2-(trifluoromethyl)pyrimidin-5-yl]-1H-pyrazolo[3,4-d]pyrimidin-4-amine, enantiomer 1 | 189.00 | 219.33 |
| 90 | 1-{1-[1-(2-fluorophenyl)-1H-1,2,3-triazol-4-yl]propyl}-3-[2-(trifluoromethyl)pyrimidin-5-yl]-1H-pyrazolo[3,4-d]pyrimidin-4-amine, enantiomer 2 | 31.51 | 31.84 |
| 91 | 1-{1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine | N.D. | N.D. |
| 92 | 1-{1-[1-(2-fluorophenyl)-1H-1,2,3-triazol-4-yl]propyl}-3-[2-(trifluoromethyl)pyrimidin-5-yl]-1H-pyrazolo[3,4-d]pyrimidin-4-amine | N.D. | N.D. |
| 93 | 5-(4-chlorophenyl)-7-{[1-(2-fluorophenyl)-1H-1,2,3-triazol-4-yl]methyl}imidazo[5,1-f][1,2,4]triazin-4-amine | 115.60 | 54.42 |
| 94 | 1-[1-(1-phenyl-1H-1,2,3-triazol-4-yl)propyl]-3-[2-(trifluoromethyl)pyrimidin-5-yl]-1H-pyrazolo[3,4-d]pyrimidin-4-amine, enantiomer 1 | 74.37 | 50.30 |
| 95 | 1-[1-(1-phenyl-1H-1,2,3-triazol-4-yl)propyl]-3-[2-(trifluoromethyl)pyrimidin-5-yl]-1H-pyrazolo[3,4-d]pyrimidin-4-amine, enantiomer 2 | 188.00 | 349.21 |
| 96 | 4-amino-5-[2-(difluoromethyl)pyrimidin-5-yl]-7-{1-[1-(2-fluorophenyl)-1H-pyrazol-4-yl]ethyl}pyrrolo[2,1-f][1,2,4]triazine-6-carbonitrile, enantiomer 1 | 0.40 | N.D. |
| 97 | 4-amino-5-[2-(difluoromethyl)pyrimidin-5-yl]-7-{1-[1-(2-fluorophenyl)-1H-pyrazol-4-yl]ethyl}pyrrolo[2,1-f][1,2,4]triazine-6-carbonitrile, enantiomer 2 | 3.87 | N.D. |
| 98 | 7-{1-[1-(2,5-difluorophenyl)-1H-1,2,3-triazol-4-yl]ethyl}-5-[2-(trifluoromethyl)pyrimidin-5-yl]pyrrolo[2,1-f][1,2,4]triazin-4-amine, enantiomer 1 | 19.81 | 25.97 |
| 99 | 1-{1-[1-(2,4-difluorophenyl)-1H-1,2,3-triazol-4-yl]propyl}-3-[2-(trifluoromethyl)pyrimidin-5-yl]-1H-pyrazolo[3,4-d]pyrimidin-4-amine, enantiomer 1 | 29.17 | 37.19 |

N.D. means not determined

The invention claimed is:

1. A compound of Formula I

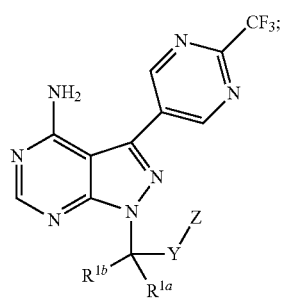

or a pharmaceutically acceptable salt thereof; wherein

Y is a five membered heteroaryl comprising one to four heteroatoms each of which is independently selected from the group consisting of N, O and S(O)$_n$; wherein the heteroaryl is optionally substituted with one to three substituents each of which is independently selected from the group consisting of halo, $C_1$-$C_6$ alkyl and $C_1$-$C_6$ haloalkyl;

Z is phenyl, optionally substituted with one to three halo;

$R^{1a}$ and $R^{1b}$ are each independently selected from the group consisting of —H, —OH, halo, $C_1$-$C_6$ alkyl optionally substituted with one to three substituents each of which is independently selected from the group consisting of halo, —OH, $C_1$-$C_3$ alkoxy, $C_3$-$C_7$ cycloalkyl and a four to seven membered heterocycloalkyl comprising one to three heteroatoms each of which is independently selected from the group consisting of N, O and S(O)$_n$, $C_3$-$C_7$ cycloalkyl optionally substituted with one to three substituents each of which is independently selected from the group consisting of —OH, halo and $C_1$-$C_6$ alkyl, and four to seven membered heterocycloalkyl comprising one to three heteroatoms each of which is independently selected from the group consisting of N, O and S(O)$_n$; and wherein the four to seven membered heterocycloalkyl is optionally substituted with one to three substituents each of which is independently selected from the group consisting of —OH, halo and $C_1$-$C_6$ alkyl;

or $R^{1a}$ and $R^{1b}$ taken together with the carbon to which they are attached form a $C_3$-$C_7$ cycloalkyl or a four to seven membered heterocycloalkyl comprising one to three heteroatoms each of which is independently selected from the group consisting of N, O and S(O)$_n$; and wherein the $C_3$-$C_7$ cycloalkyl or four to seven membered heterocycloalkyl are optionally substituted with one to three substituents each of which is independently selected from the group consisting of —OH, halo and $C_1$-$C_6$ alkyl; and n at each occurrence is independently 0, 1 or 2.

2. The compound of claim 1 wherein one of $R^{1a}$ and $R^{1b}$ is $C_1$-$C_6$ alkyl and the other is —H; or a pharmaceutically acceptable salt thereof.

3. The compound of claim 2 wherein the moiety Y—Z is selected from the group consisting of

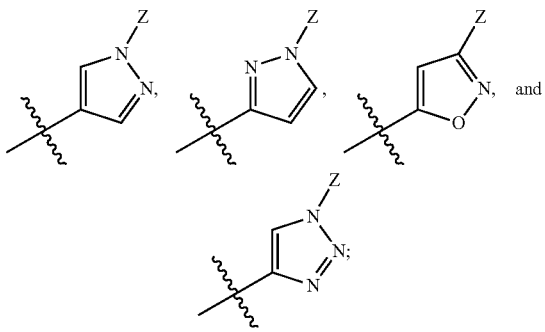

or a pharmaceutically acceptable salt thereof.

4. The compound of claim 3 wherein Z is phenyl optionally substituted with one or two fluoro or chloro; or a pharmaceutically acceptable salt thereof.

5. The compound of claim 1, wherein the compound is selected from the group consisting of
- 1-{(1S)-1-[1-(2-fluorophenyl)-1H-pyrazol-4-yl]propyl}-3-[2-(trifluoromethyl) pyrimidin-5-yl]-1H-pyrazolo[3,4-d]pyrimidin-4-amine;
- 1-{(1R)-1-[1-(2-fluorophenyl)-1H-pyrazol-4-yl]propyl}-3-[2-(trifluoromethyl) pyrimidin-5-yl]-1H-pyrazolo[3,4-d]pyrimidin-4-amine;
- 1-{(1S)-1-[1-(2-fluorophenyl)-1H-1,2,3-triazol-4-yl]propyl}-3-[2-(trifluoromethyl) pyrimidin-5-yl]-1H-pyrazolo[3,4-d]pyrimidin-4-amine; and
- 1-{(1R)-1-[1-(2-fluorophenyl)-1H-1,2,3-triazol-4-yl]propyl}-3-[2-(trifluoromethyl) pyrimidin-5-yl]-1H-pyrazolo[3,4-d]pyrimidin-4-amine;

or a pharmaceutically acceptable salt thereof.

6. The compound of claim 1, wherein the compound is 1-{(1S)-1-[1-(2-fluorophenyl)-1H-pyrazol-4-yl]propyl}-3-[2-(trifluoromethyl)pyrimidin-5-yl]-1H-pyrazolo[3,4-d]pyrimidin-4-amine or a pharmaceutically acceptable salt thereof.

7. A method for treating cystic fibrosis, asthma, bronchiectasis, chronic obstructive pulmonary disease (COPD), constipation, Diabetes mellitus, dry eye disease, pancreatitis, rhinosinusitis, or Sjogren's Syndrome in a patient in need of treatment thereof, the method comprising administering a therapeutically effective amount of a compound according to claim 1, or a pharmaceutically acceptable salt of said compound, to the patient in need of treatment thereof.

8. The method of claim 7, wherein the method is for treating cystic fibrosis.

9. A pharmaceutical composition comprising a therapeutically effective amount of one or more of a compound according to claim 1, or a pharmaceutically acceptable salt thereof together with a pharmaceutically acceptable carrier.

10. The pharmaceutical composition of claim 9, further comprising one or more additional therapeutic agents.

11. The pharmaceutical composition of claim 10, wherein the one or more additional therapeutic agents are independently selected from the group consisting of a CFTR potentiator, a CFTR corrector, an epithelial sodium channel (ENaC) inhibitor, a CFTR amplifier, a CFTR stabilizer, a read-through agent, an oligonucleotide patch, an autophagy inducer, and a proteostasis modulator.

12. The pharmaceutical composition of claim 11, wherein the CFTR potentiator at each occurrence is selected from the group consisting of VX-770 (Ivacaftor), GLPG-1837, GLPG-2451, QBW-251, FDL-176, FDL-129, CTP-656, and PTI-P271.

13. The pharmaceutical composition of claim 11, wherein the CFTR corrector at each occurrence is selected from the group consisting of VX-809 (lumacaftor), VX-661 (tezacaftor), VX-983, VX-152, VX-440, VX-659, GLPG-2737, P247-A, GLPG-2222, GLPG-2665, GLPG-2851, FDL-169, and PTI-C1811.

14. The pharmaceutical composition of claim 11, wherein the epithelial sodium channel (ENaC) inhibitor at each occurrence is selected from the group consisting of SPX-101, QBW-276 and VX-371.

15. The pharmaceutical composition of claim 11, wherein the CFTR amplifier at each occurrence is selected from the group consisting of PTI-428 and PTI-130.

16. The pharmaceutical composition of claim 11, wherein the CFTR stabilizer is N-91115 (Cavosonstat).

17. The pharmaceutical composition of claim 11, wherein the read-through agent is ataluren.

18. The pharmaceutical composition of claim 11, wherein the oligonucleotide patch is QR-010.

19. The pharmaceutical composition of claim 11, wherein the autophagy inducer at each occurrence is selected from the group consisting of CX-4945 and the combination of cysteamine and epigallocatechin gallate (EGCG).

* * * * *